(12) United States Patent
Ptacin et al.

(10) Patent No.: US 11,834,689 B2
(45) Date of Patent: Dec. 5, 2023

(54) INCORPORATION OF UNNATURAL NUCLEOTIDES AND METHODS THEREOF

(71) Applicants: SYNTHORX, INC., La Jolla, CA (US); THE SCRIPPS RESEARCH INSTITUTE, La Jolla, CA (US)

(72) Inventors: Jerod Ptacin, La Jolla, CA (US); Carolina Caffaro, La Jolla, CA (US); Hans Aerni, La Jolla, CA (US); Yorke Zhang, La Jolla, CA (US); Emil C. Fischer, La Jolla, CA (US); Aaron W. Feldman, La Jolla, CA (US); Vivian T. Dien, La Jolla, CA (US); Floyd E. Romesberg, La Jolla, CA (US)

(73) Assignees: THE SCRIPPS RESEARCH INSTITUTE, La Jolla, CA (US); SYNTHORX, INC., La Jolla, CA (US)

( * ) Notice: Subject to any disclaimer, the term of this patent is extended or adjusted under 35 U.S.C. 154(b) by 182 days.

(21) Appl. No.: 17/196,151

(22) Filed: Mar. 9, 2021

(65) Prior Publication Data
US 2021/0222147 A1 Jul. 22, 2021

Related U.S. Application Data

(63) Continuation of application No. 16/629,255, filed as application No. PCT/US2018/041509 on Jul. 10, 2018, now abandoned.

(60) Provisional application No. 62/531,325, filed on Jul. 11, 2017.

(51) Int. Cl.
| | | |
|---|---|---|
| *C12N 9/00* | (2006.01) | |
| *C12P 21/02* | (2006.01) | |
| *C12N 15/113* | (2010.01) | |
| *C12N 15/90* | (2006.01) | |

(52) U.S. Cl.
CPC ............. *C12N 9/93* (2013.01); *C12N 15/113* (2013.01); *C12N 15/90* (2013.01); *C12P 21/02* (2013.01); *C12Y 601/01026* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. et al. | |
| 4,469,863 A | 9/1984 | Ts et al. | |
| 4,476,301 A | 10/1984 | Imbach et al. | |
| 4,587,044 A | 5/1986 | Miller et al. | |
| 4,605,735 A | 8/1986 | Miyoshi et al. | |
| 4,667,025 A | 5/1987 | Miyoshi et al. | |
| 4,683,195 A | 7/1987 | Mullis et al. | |
| 4,683,202 A | 7/1987 | Mullis | |
| 4,762,779 A | 8/1988 | Snitman | |
| 4,766,106 A | 8/1988 | Katre et al. | |
| 4,789,737 A | 12/1988 | Miyoshi et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,845,205 A | 7/1989 | Huynh et al. | |
| 4,849,513 A | 7/1989 | Smith et al. | |
| 4,876,335 A | 10/1989 | Yamane et al. | |
| 4,902,502 A | 2/1990 | Nitecki et al. | |
| 4,904,582 A | 2/1990 | Tullis | |
| 4,910,300 A | 3/1990 | Urdea et al. | |
| 4,931,544 A | 6/1990 | Katre et al. | |
| 4,948,882 A | 8/1990 | Ruth | |
| 4,958,013 A | 9/1990 | Letsinger | |
| 4,965,188 A | 10/1990 | Mullis et al. | |
| 4,981,957 A | 1/1991 | Lebleu et al. | |
| 5,015,733 A | 5/1991 | Smith et al. | |
| 5,023,243 A | 6/1991 | Tullis | |
| 5,034,506 A | 7/1991 | Summerton et al. | |
| 5,082,830 A | 1/1992 | Brakel et al. | |
| 5,089,261 A | 2/1992 | Nitecki et al. | |
| 5,093,232 A | 3/1992 | Urdea et al. | |
| 5,109,124 A | 4/1992 | Ramachandran et al. | |
| 5,112,963 A | 5/1992 | Pieles et al. | |
| 5,118,800 A | 6/1992 | Smith et al. | |
| 5,118,802 A | 6/1992 | Smith et al. | |
| 5,130,302 A | 7/1992 | Spielvogel et al. | |
| 5,134,066 A | 7/1992 | Rogers et al. | |
| 5,138,045 A | 8/1992 | Cook et al. | |
| 5,166,315 A | 11/1992 | Summerton et al. | |
| 5,175,273 A | 12/1992 | Bischofberger et al. | |
| 5,177,196 A | 1/1993 | Meyer, Jr. et al. | |
| 5,185,444 A | 2/1993 | Summerton et al. | |
| 5,188,897 A | 2/1993 | Suhadolnik et al. | |
| 5,206,344 A | 4/1993 | Katre et al. | |
| 5,214,134 A | 5/1993 | Weis et al. | |

(Continued)

FOREIGN PATENT DOCUMENTS

| | | |
|---|---|---|
| EP | 0154316 B1 | 9/1989 |
| EP | 0614907 A1 | 9/1994 |

(Continued)

OTHER PUBLICATIONS

Malyshev and Romesberg, "The Expanded Genetic Alphabet", Angewandte Chemie International Edition, vol. 54, Issue 41, pp. 11930-11944 (Year: 2015).*
Manandhar et al.,"Genetic Code Expansion: Inception, Development, Commercialization", Journal of the American Chemical Society, 143: 4859-4878 (Year: 2021).*
Cervettini et al.,"Rapid discovery and evolution of orthogonal aminoacyl-tRNA synthetase-tRNA pairs", Nature Biotechnology, vol. 38, pp. 989-999 (Year: 2020).*
Oehm, Stefan. Adaptation of *E. coli* towards Tryptophan analog usage. Approved Dissertation (2016).
Acimovic et al. Molecular Evolution of the Equilibrative Nucleoside Transporter Family: Identification of Novel Family Members in Prokaryotes and Eukaryotes. Mol Biol Evol 12:2199-2210 (2002).

(Continued)

*Primary Examiner* — Anand U Desai
(74) *Attorney, Agent, or Firm* — McNeill Baur PLLC

(57) ABSTRACT

Disclosed herein are methods, compositions and kits for the synthesis of proteins which comprises unnatural amino acids that utilize a mutant tRNA.

25 Claims, 25 Drawing Sheets

(56) References Cited

U.S. PATENT DOCUMENTS

| | | |
|---|---|---|
| 5,214,136 A | 5/1993 | Lin et al. |
| 5,216,141 A | 6/1993 | Benner |
| 5,218,105 A | 6/1993 | Cook et al. |
| 5,229,109 A | 7/1993 | Grimm et al. |
| 5,232,841 A | 8/1993 | Hashimoto et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,273 A | 12/1993 | Buckholz |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,370,995 A | 12/1994 | Hennecke et al. |
| 5,371,241 A | 12/1994 | Brush |
| 5,389,529 A | 2/1995 | Panayotatos et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,719 A | 11/1995 | Meng et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,612,199 A | 3/1997 | Western et al. |
| 5,614,185 A | 3/1997 | Koths et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,643,564 A | 7/1997 | Hamaguchi et al. |
| 5,645,985 A | 7/1997 | Froehler et al. |
| 5,646,265 A | 7/1997 | McGee |
| 5,648,247 A | 7/1997 | Picataggio et al. |
| 5,656,493 A | 8/1997 | Mullis et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,712,114 A | 1/1998 | Mankovich et al. |
| 5,714,331 A | 2/1998 | Buchardt et al. |
| 5,719,262 A | 2/1998 | Buchardt et al. |
| 5,747,646 A | 5/1998 | Hakimi et al. |
| 5,750,692 A | 5/1998 | Cook et al. |
| 5,763,588 A | 6/1998 | Matteucci et al. |
| 5,830,653 A | 11/1998 | Froehler et al. |
| 5,834,594 A | 11/1998 | Hakimi et al. |
| 5,846,818 A | 12/1998 | Robinson et al. |
| 5,888,732 A | 3/1999 | Hartley et al. |
| 5,932,474 A | 8/1999 | Tsien et al. |
| 6,005,096 A | 12/1999 | Matteucci et al. |
| 6,008,378 A | 12/1999 | Tsien et al. |
| 6,010,871 A | 1/2000 | Takahara et al. |
| 6,013,526 A | 1/2000 | Takahara et al. |
| 6,054,271 A | 4/2000 | Tsien et al. |
| 6,124,090 A | 9/2000 | Rose et al. |
| 6,143,557 A | 11/2000 | Hartley et al. |
| 6,171,861 B1 | 1/2001 | Hartley et al. |
| 6,261,797 B1 | 7/2001 | Sorge et al. |
| 6,268,490 B1 | 7/2001 | Imanishi et al. |
| 6,270,969 B1 | 8/2001 | Hartley et al. |
| 6,277,608 B1 | 8/2001 | Hartley et al. |
| 6,288,302 B1 | 9/2001 | Yu et al. |
| 6,294,323 B1 | 9/2001 | Ullman et al. |
| 6,365,375 B1 | 4/2002 | Dietmaier et al. |
| 6,391,544 B1 | 5/2002 | Salituro et al. |
| 6,451,569 B1 | 9/2002 | Tsien et al. |
| 6,525,191 B1 | 2/2003 | Ramasamy |
| 6,670,461 B1 | 12/2003 | Wengel et al. |
| 6,720,140 B1 | 4/2004 | Hartley et al. |
| 6,770,748 B2 | 8/2004 | Imanishi et al. |
| 6,794,499 B2 | 9/2004 | Wengel et al. |
| 6,906,170 B1 | 6/2005 | Lider et al. |

(56) References Cited

U.S. PATENT DOCUMENTS

| | | |
|---|---|---|
| 6,955,807 B1 | 10/2005 | Shanafelt et al. |
| 7,034,133 B2 | 4/2006 | Wengel et al. |
| 7,045,337 B2 | 5/2006 | Schultz et al. |
| 7,053,207 B2 | 5/2006 | Wengel |
| 7,105,653 B2 | 9/2006 | Shanafelt et al. |
| 7,393,632 B2 | 7/2008 | Cheo et al. |
| 7,399,845 B2 | 7/2008 | Seth et al. |
| 7,427,672 B2 | 9/2008 | Imanishi et al. |
| 7,625,717 B2 | 12/2009 | Chin et al. |
| 7,670,823 B1 | 3/2010 | Hartley et al. |
| 7,741,457 B2 | 6/2010 | Seth et al. |
| 7,744,861 B2 | 6/2010 | Zhao et al. |
| 7,803,777 B2 | 9/2010 | Defrees |
| 8,252,743 B2 | 8/2012 | Guyon et al. |
| 8,273,833 B2 | 9/2012 | Bentley et al. |
| 8,420,792 B2 | 4/2013 | Tian et al. |
| 8,501,805 B2 | 8/2013 | Seth et al. |
| 8,546,556 B2 | 10/2013 | Seth et al. |
| 8,557,776 B2 | 10/2013 | Lehmann et al. |
| 8,609,383 B2 | 12/2013 | Young et al. |
| 9,089,614 B2 | 7/2015 | Lin et al. |
| 9,682,934 B2 | 6/2017 | Stafford et al. |
| 9,840,493 B2 | 12/2017 | Yang et al. |
| 9,938,516 B2 | 4/2018 | Zimmerman et al. |
| 9,988,619 B2 | 6/2018 | Zimmerman et al. |
| 10,513,706 B2 | 12/2019 | Romesberg et al. |
| 10,626,138 B2 | 4/2020 | Romesberg et al. |
| 10,696,719 B2 | 6/2020 | Romesberg et al. |
| 10,696,720 B2 | 6/2020 | Romesberg et al. |
| 2002/0001804 A1 | 1/2002 | Mitchell et al. |
| 2002/0007051 A1 | 1/2002 | Cheo et al. |
| 2003/0083373 A1 | 5/2003 | Tsien et al. |
| 2004/0171570 A1 | 9/2004 | Allerson et al. |
| 2005/0112590 A1 | 5/2005 | Boom et al. |
| 2005/0118623 A1 | 6/2005 | Belousov et al. |
| 2005/0130923 A1 | 6/2005 | Bhat et al. |
| 2006/0035254 A1 | 2/2006 | Manoharan et al. |
| 2006/0074035 A1 | 4/2006 | Hong et al. |
| 2006/0084136 A1 | 4/2006 | Kudlicki et al. |
| 2006/0263771 A1 | 11/2006 | Hirao et al. |
| 2007/0287831 A1 | 12/2007 | Seth et al. |
| 2008/0039618 A1 | 2/2008 | Allerson et al. |
| 2008/0300163 A1 | 12/2008 | Cho et al. |
| 2009/0155844 A1 | 6/2009 | Yokoyama et al. |
| 2010/0323364 A1 | 12/2010 | Sekine et al. |
| 2012/0022013 A1 | 1/2012 | Sinclair et al. |
| 2012/0077252 A1 | 3/2012 | Picataggio et al. |
| 2012/0244112 A1 | 9/2012 | Ast et al. |
| 2013/0183761 A1 | 7/2013 | Chin et al. |
| 2013/0333068 A1 | 12/2013 | Coffin |
| 2014/0068797 A1 | 3/2014 | Doudna et al. |
| 2014/0255345 A1 | 9/2014 | Grabstein et al. |
| 2014/0273226 A1 | 9/2014 | Wu |
| 2014/0314864 A1 | 10/2014 | Cheng et al. |
| 2014/0315245 A1 | 10/2014 | Yam et al. |
| 2014/0328791 A1 | 11/2014 | Bossard et al. |
| 2017/0044229 A1 | 2/2017 | Garcia et al. |
| 2017/0260137 A1 | 9/2017 | Stafford et al. |
| 2017/0283469 A1 | 10/2017 | Thanos et al. |
| 2017/0369871 A1 | 12/2017 | Ptacin et al. |
| 2018/0051065 A1 | 2/2018 | Yin |
| 2018/0086734 A1 | 3/2018 | Yang et al. |
| 2019/0218257 A1 | 7/2019 | Romesberg et al. |
| 2019/0376054 A1 | 12/2019 | Ptacin et al. |
| 2020/0017540 A1 | 1/2020 | Romesberg et al. |
| 2020/0024597 A1 | 1/2020 | Ptacin et al. |
| 2020/0040027 A1 | 2/2020 | Romesberg et al. |
| 2020/0095591 A1 | 3/2020 | Romesberg et al. |
| 2020/0131555 A1 | 4/2020 | Ptacin et al. |
| 2020/0224234 A1 | 7/2020 | Romesberg et al. |
| 2020/0277342 A1 | 9/2020 | Romesberg et al. |
| 2020/0318122 A1 | 10/2020 | Romesberg et al. |
| 2020/0377877 A1 | 12/2020 | Romesberg et al. |
| 2020/0392550 A1 | 12/2020 | Romesberg et al. |
| 2022/0228148 A1 | 7/2022 | Romesberg et al. |
| 2022/0243244 A1 | 8/2022 | Romesberg et al. |

FOREIGN PATENT DOCUMENTS

| | | |
|---|---|---|
| EP | 0629633 A2 | 12/1994 |
| EP | 0811385 B1 | 8/2003 |
| EP | 2130835 A1 | 12/2009 |
| EP | 2581450 B1 | 8/2018 |
| JP | 2007510401 A | 4/2007 |
| WO | WO-9213869 A1 | 8/1992 |
| WO | WO-9422890 A1 | 10/1994 |
| WO | WO-9735869 A1 | 10/1997 |
| WO | WO-9914226 A2 | 3/1999 |
| WO | WO-9921013 A1 | 4/1999 |
| WO | WO-9962923 A2 | 12/1999 |
| WO | WO-0023456 A1 | 4/2000 |
| WO | WO-0074724 A2 | 12/2000 |
| WO | WO-0105801 A1 | 1/2001 |
| WO | WO-0132887 A1 | 5/2001 |
| WO | WO-0236626 A1 | 5/2002 |
| WO | WO-02062816 A1 | 8/2002 |
| WO | WO-02070533 A2 | 9/2002 |
| WO | WO-03031464 A2 | 4/2003 |
| WO | WO-03055898 A1 | 7/2003 |
| WO | WO-03070918 A2 | 8/2003 |
| WO | WO-2004007713 A1 | 1/2004 |
| WO | WO-2004060300 A2 | 7/2004 |
| WO | WO-2004099231 A2 | 11/2004 |
| WO | WO-2004106356 A1 | 12/2004 |
| WO | WO-2005007121 A2 | 1/2005 |
| WO | WO-2005021570 A1 | 3/2005 |
| WO | WO-2005026187 A1 | 3/2005 |
| WO | WO-2005045015 A2 | 5/2005 |
| WO | WO-2005092928 A1 | 10/2005 |
| WO | WO-2006049297 A1 | 5/2006 |
| WO | WO-2006081510 A2 | 8/2006 |
| WO | WO-2006082184 A2 | 8/2006 |
| WO | WO-2007015557 A1 | 2/2007 |
| WO | WO-2007066737 A2 | 6/2007 |
| WO | WO-2007085485 A2 | 8/2007 |
| WO | WO-2007090071 A2 | 8/2007 |
| WO | WO-2007093599 A1 | 8/2007 |
| WO | WO-2007134181 A2 | 11/2007 |
| WO | WO-2008067825 A1 | 6/2008 |
| WO | WO-2008101157 A1 | 8/2008 |
| WO | WO-2008106186 A2 | 9/2008 |
| WO | WO-2008150729 A2 | 12/2008 |
| WO | WO-2008154401 A2 | 12/2008 |
| WO | WO-2009006478 A2 | 1/2009 |
| WO | WO-2009038195 A1 | 3/2009 |
| WO | WO-2009123216 A1 | 10/2009 |
| WO | WO-2009155102 A2 | 12/2009 |
| WO | WO-2010023670 A2 | 3/2010 |
| WO | WO-2010085495 A1 | 7/2010 |
| WO | WO-2011043385 A1 | 4/2011 |
| WO | WO-2011053065 A2 | 5/2011 |
| WO | WO-2011139699 A2 | 11/2011 |
| WO | WO-2012038706 A1 | 3/2012 |
| WO | WO-2012065086 A1 | 5/2012 |
| WO | WO-2014160025 A2 | 10/2014 |
| WO | WO-2015021432 A1 | 2/2015 |
| WO | WO-2015038426 A1 | 3/2015 |
| WO | WO-2015086795 A1 | 6/2015 |
| WO | WO-2015157555 A2 | 10/2015 |
| WO | WO-2016025385 A1 | 2/2016 |
| WO | WO-2016073433 A1 | 5/2016 |
| WO | WO-2016094867 A1 | 6/2016 |
| WO | WO-2016115168 | 7/2016 |
| WO | WO-2016115168 A1 | 7/2016 |
| WO | WO-2017106767 A1 | 6/2017 |
| WO | WO-2017112825 A2 | 6/2017 |
| WO | WO-2017223528 A1 | 12/2017 |
| WO | WO-2019014262 A1 | 1/2019 |
| WO | WO-2019014267 A1 | 1/2019 |
| WO | WO-2019028419 A1 | 2/2019 |
| WO | WO-2019028425 A1 | 2/2019 |

(56) References Cited

FOREIGN PATENT DOCUMENTS

| | | |
|---|---|---|
| WO | WO-2019133883 A1 | 7/2019 |
| WO | WO-2021067313 A1 | 4/2021 |
| WO | WO-2022087475 A1 | 4/2022 |

OTHER PUBLICATIONS

Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).
Agris. Decoding the genome: a modified view. Nucleic Acids Res 32:223-238 (2004).
Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).
Allen et al. Roles of DNA polymerase I in leading and lagging-strand replication defined by a high-resolution mutation footprint of ColE1 plasmid replication. Nucleic Acids Res. 39:7020-7033 (2011).
Alpert et al. ABRF 2003: Precipitation of Large, High-Abundance Proteins from Serum With Organic Solvents. Poster No. P111-W (10 pgs) (2003).
Ambrogelly et al. Pyrrolysine is not hardwired for cotranslational insertion at UAG condons. PNAS 104(9):3141-3146 (2007).
Amiri et al. Deep origin of plastid/parasite ATP/ADP translocases. J. Mol. Evol. 56:137-150 (2003).
Arenas-Ramirez et al. Improved cancer immunotherapy by a CD25-mimobody conferring selectivity to human interleukin-2. Sci Transl Med 8:367ra166 (Nov. 30, 2016). 13 pages.
Arie et al. Phylogenetic identification of n-alkane assimilating *Candida* yeasts based on nucleotide divergence in the 59 end of LSU rDNA gene. J Gen Appl Microbiol. 46(5):257-262 (2000).
Asagarasu et al. Design and synthesis of piperazinylpyridine derivatives as novel 5-HT1A agonists/5-HT3 antagonists for the treatment of irritable bowel syndrome (IBS). Chem. Pharm. Bull. (Tokyo)57:34-42 (2009).
Ast et al. Diatom plastids depend on nucleotide import from the cytosol. PNAS USA 106:3621-3626 (2009).
Audia et al. Study of the five Rickettsia prowazekii proteins annotated as ATP/ADP translocases (Tlc): Only Tlc1 transports ATP/ADP, while Tlc4 and T1c5 transport other ribonucleotides. J. Bacteriol. 188:6261-6268 (2006).
Baba et al. Construction of *Escherichia coli* K-12 in-frame, single-gene knockout mutants: the Keio collection. Mol Syst Biol 2006. 0008 (2006).
Beigelman et al. Synthesis of 5'-C-Methyl-D-allo- & L-Talo-ribonucleoside 3'-O-Phosphoramidites & Their Incorporation into Hammerhead Ribozymes. Nucleosides and Nucleotides 14(3-5):901-905 (1995).
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28(15):2911-2914 (2000).
Betz et al. KlenTaq polymerase replicates unnatural base pairs by inducing a Watson-Crick geometry. Nat Chem Biol 8:612-614 (2012).
Betz et al. Structural insights into DNA replication without hydrogen bonds. J Am Chem Soc 135:18637-18643 (2013).

Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bohringer et al. Synthesis of 5'-deoxy-5'-methylphosphonate linked thymidine oligonucleotides. Tet Lett 34:2723-2726 (1993).
Bordo et al. Suggestions for "safe" residue substitutions in site-directed mutagenesis. J Mol Biol 217:721-729 (1991).
Boyman et al. Selective Stimulation of T Cell subsets with Antibody-Cytokine Immune Complexes. Science 311:1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Braasch et al. Locked nucleic acid (LNA): fine-tuning the recognition of DNA and RNA. Chem Bio 8:1-7 (2001).
Branca. Rekindling cancer vaccines. Nat Biotechnol 34(10):1019-1025 (2016).
Brauns et al. Studies on Lignin and Related Compounds: XII. Methanol Lignin. Canadian Journal of Research 13b(1):28-34 (1935).
Cameron et al. Tunable protein degradation in bacteria. Nature Biotechnology 32:1276-1281 (2014).
Cann et al. A heterodimeric DNA polymerase: Evidence that members of Euryarchaeota possess a distinct DNA polymerase. PNAS USA 95:14250 (1998).
Cantrell. Vectors for the expression of recombinant proteins in *E. coli*. Methods Mol Biol. 235:257-75 (2003).
Capone et al. Amber, ochre and opal suppressor tRNA genes derived from a human serine tRNA gene. EMBO J 4(1): 213-221 (1985).
Cariello et al. Fidelity of Thermococcus litoralis DNA polymerase (VentTM) in PCR determined by denaturing gradient gel electrophoresis Nucl Acid Res 19:4193-4198 (1991).
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. Modeling the receptor pharmacology, pharmacokinetics, and pharmacodynamics of NKTR-214, a kinetically-controlled interleukin-2 (IL2) receptor agonist for cancer immunotherapy. PLoS One 12(7):e0179431 (2017).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).
Chastgner et al. Lack of intermediate-affinity interleukin-2 receptor in mice leads to dependence on interkeukin-2 receptor α,β and γ chain expression forT cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. Selective chemical labeling of proteins. Org. Biomol. Chem. 14:5417 (2016).
Chen et al. The expanding world of DNA and RNA. Curr Opin Chem Biol 34:80-87 (2016).

(56) References Cited

OTHER PUBLICATIONS

Chien et al. Deoxyribonucleic acid polymerase from the extreme thermophile Thermus aquaticus. J Bacteriol 127:1550-1557 (1976).
Cleary et al. Production of complex nucleic acid libraries using highly parallel in situ oligonucleotide synthesis. Nat Methods 1(3):241-248 (2004).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
Dahl et al. Discovery and validation of a series of aryl sulfonamides as selective inhibitors of tissue-nonspecific alkaline phosphatase (TNAP). J Med Chem 52(21):6919-6925 (2009).
Database UniParc [Online] May 31, 2010 (May 31, 2010), Database accession No. UPI0001D42ADE(2 pgs).
Datsenko et al. One-step inactivation of chromosomal genes in *Escherichia coli* K-12 using PCR products. PNAS USA 97(12):6640-6645 (2000).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Deuschle et al. Promoters of *Escherichia coli*: a hierarchy of in vivo strength indicates alternate structures. EMBO J 5:2987-2994 (1986).
Dhami et al. Systematic exploration of a class of hydrophobic unnatural base pairs yields multiple new candidates for the expansion of the genetic alphabet. Nucleic Acids Res 42:10235-10244 (2014).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Doudna et al. Genome editing. The new frontier of genome engineering with CRISPR-Cas9. Science 346:1258096 (2014).
Dranoff. Cytokines in cancer pathogenesis and cancer therapy. Nature Reviews Cancer 4:11-22 (2004).
Dufour. THOR-707, an engineered not-alpha IL-2, for the treatment of solid tumors induces strong immunological responses in vivo. CSCO Immunotherapy Seminar Mar. 22-23, 2019 Shanghi, China (12 pgs).
Dumas et al. Designing logical codon reassignment—Expanding the chemistry in biology. Chem Sci 6:50-69 (2015).
Dupradeau et al. Differential solvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbiol Rev 52(3):354-374 (1988).
Egholm et al. PNA hybridizes to complementary oligonucleotides obeying the Watson-Crick hydrogen-bonding rules. Nature 365(6446):566-568 (1993).

El Yacoubi et al. Biosynthesis and function of posttranscriptional modifications of transfer RNAs. Annu Rev Genet 46:69-95 (2012).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Engleerg-Kukla et al. Chapter 60: Suppression of Termination Codons. *Escherichia coli* and *Salmonella* Cellular and Molecular Biology (pp. 909-921) (1996).
Engler et al. A one pot, one step, precision cloning method with high throughput capability. PLoS One 3:e3647 (2008).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Fidanza et al. Functionalization of oligonucleotides by the incorporation of thio-specific reporter groups. In Protocols for Oligonucleotide Conjugates. Protocols for Oligonucleotide Conjugates: Synthesis and Analytical Techniques 26:121-143 (1994).
Fidanza et al. Site-specific labeling of DNA sequences containing phosphorothioate diesters. JACS 114(14):5509-5517 (2002).
Fisher et al. Chlamydia trachomatis Transports NAD via the Npt1 ATP/ADP Translocase. Journal of Bacteriology 195(15):3381-3386 (2013).
Floros et al. Anticancer Cytokines: Biology and Clinical Effects of Interferon-α2, Interleukin (IL)-2, IL-15, IL-21, and IL-12. Semin Oncol 42(4):539-548 (2015).
Fluman et al. mRNA-programmed translation pauses in the targeting of *E. coli* membrane proteins. eLife 2014; 3:e03440.
Fourrey et al. Photo Rearrangement of Phenyl Selenide Derivatives Access to Selenium Substituted C Nucleosides. Tetrahedron Letters 21:455-458 (1980).
Friedhoff et al. Quantitative polymerase chain reaction with oligodeoxynucleotide ligation assay/enzyme-linked immunosorbent assay detection. Anal Biochem 215(1):9-16 (1993).
Fu et al. Improving CRISPR-Cas nuclease specificity using truncated guide RNAs. Nat Biotechnol 32:279-284 (2014).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).

(56) References Cited

OTHER PUBLICATIONS

Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gibson et al. Enzymatic assembly of DNA molecules up to several hundred kilobases. Nat Methods. 6(5):343-5 (2009).
Gietz et al. Improved method for high efficiency transformation of intact yeast cells. Nucleic Acids Res 20:1425 (1992).
Gillies et al. A Low-Toxicity IL-2-based Immunocytokine Retains Antitumor Activity Despite its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Gong et al. Recent advances in bioorthogonal reactions for site-specific protein labeling and engineering. Tetrahedron Letters 56:2123-2131 (2015).
Goodman. Error-prone repair DNA polymerases in prokaryotes and eukaryotes. Annu. Rev. Biochem. 71:17-50 (2002).
Goodman et al. Causes and effects of N-terminal codon bias in bacterial genes. Science 342:475-479 (2013).
Guatelli et al. Isothermal, in vitro amplification of nucleic acids by a multienzyme reaction modeled after retroviral replication. PNAS USA 87(5):1874-1878 (1990).
Guo et al. Directed evolution of an enhanced and highly efficient FokI cleavage domain for zinc finger nucleases. J Mot Biol 400:96-107 (2010).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma.Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Horvath et al. CRISPR/Cas, the Immune System of Bacteria and Archaea. Science 327:167-170 (2010).
Hsu et al. Development and applications of CRISPR-Cas9 for genome engineering. Cell 157(6):1262-78 (2014).
Hu et al. The Generation of Low Toxicity lnterleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Imran et al. Influence of architecture of high molecular weight linear and branched polyglycerolspolyglycerols on their biocompatibility and biodistribution. Biomaterials 33:9135-9147 (2012).
Insight-Esprit Study Group et al. Interleukin-2 Therapy in Patients with HIV Infection. N Engl J Med. 361(16):1548-59 (2009).
Ishizuka et al. Site-specific functionalization of RNA molecules by an unnatural base pair transcription system via click chemistry. Chem. Comm. 48:10835-10837 (2012).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).

(56) References Cited

OTHER PUBLICATIONS

Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Khlebnikov et al. Effect of lacY expression on homogeneity of induction from the P(tac) and P(trc) promoters by natural and synthetic inducers. Biotechnol Prog 18:672-674 (2002).
Kim et al. Stability and polymerase recognition of pyridine nucleobase analogues: role of minor-groove H-bond acceptors. Angew Chem Int Ed Engl 45(46):7809-12 (2006).
Kimoto et al. Chemical Biology of Nucleic Acids: Fundamentals and Clinical Applications (eds A. Volker Erdmann, T. Wojciech Markiewicz, & Jan Barciszewski) pp. 131-148 (Springer Berlin Heidelberg, 2014).
Kimoto et al. Generation of high-affinity DNA aptamers using an expanded genetic alphabet. Nat. Biotech. 31(5):453-458 (2013).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Knab et al. Nucleotide parasitism by Simkania negevensis (Chlamydiac). J. Bacteriol. 193:225-235 (2011).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kranaster et al. Increased single-nucleotide discrimination in allele-specific polymerase chain reactions through primer probes bearing nucleobase and 2'-deoxyribose modifications. Chem Eur J 13(21):6115-6122 (2007).
Krieg et al. Improved IL-2 immunotherapy by selective stimulation of IL-2 receptors on lymphocytes and endothelial cells. PNAS USA 107(26):11906-11911 (Jun. 29, 2010).
Kroschwitz. The Concise Encyclopedia of Polymer Science and Engineering. (pp. 858-859) (1990).
Kubelka et al. Synthesis of 2,6-disubstituted pyridin-3-yl C-2'-deoxyribonucleosides through chemoselective transformations of bromo-chloropyridine C-nucleosides. Org. Biomol. Chem. 11:4702-4718 (2013).
Kuhlman et al. Site-specific chromosomal integration of large synthetic constructs. Nucleic Acids Res 38:e92 (2010).
Kumar et al. The First Analogues of LNA (Locked Nucleic Acids): Phosphorothioate LNA and 2'-Thio-LNA. Bioorg Med Chem Lett 8:2219-2222 (1998).
Kutyavin. Use of base-modified duplex-stabilizing deoxynucleoside 5'-triphosphates to enhance the hybridization properties of primers and probes in detection polymerase chain reaction. Biochemistry 47(51):13666-13673 (2008).
Kwoh et al. Transcription-based amplification system and detection of amplified human immunodeficiency virus type 1 with a bead-based sandwich hybridization format. PNAS USA 86:1173-1177 (1989).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lazear et al. Targeting of IL-2 to cytotoxic lymphocytes as an improved method of cytokine-driven immunotherapy. Oncoimmunology 6(2):e1265721 (2017).
Lecomte et al. Selective Inactivation of the 3' to 5' exonuclease activity of *Escherichia coli* DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).

(56) References Cited

OTHER PUBLICATIONS

Li et al. Synthesis of linear polyether polyol derivatives as new materials for bioconjugation. Bioconjugate ChemChem 20:780-789 (2009).
Liu et al. Adding new chemistries to the genetic code. Annu Rev Biochem 79:413-444 (2010).
Lizardi et al. Exponential amplification of recombinant-RNA hybridization probes. Nature Biotechnology 6:1197-1202 (1988).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Immunostimulatory Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Lyon et al. Self-hydrolyzing maleimides improve the stability and pharmacological properties of antibody-drug conjugates. Nat. Biotechnol. 32(10):1059-1062 (2014).
Mali et al. RNA-Guided Human Genome Engineering via Cas9. Science 339:823-826 (2013).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Marraffini et al. CRISPR interference: RNA-directed adaptive immunity in bacteria and archaea. Nat Rev Genet. 11(3):181-90 (2010).
Marshall et al., A link between integral membrane protein expression and simulated integration efficiency. Cell Reports 16(8): 2169-2177 (2016).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc.122:10714-10715 (2000).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Meyers et al. Optimal alignments in linear space. CABIOS 4:11-17 (1989).
Micklefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Milla et al. THOR-707: An engineered IL-2 for the treatment of solid tumors with superior preclinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).

(56) References Cited

OTHER PUBLICATIONS

Montero et al. Nucleosides de synthese XVI: Sur une synthese selective de divers ribofuranosyl-1-purines. Journal of Heterocyclic Chemistry 15(6):929-935 (1978) (English Abstract).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51:263 (1986).
Mutalik, et al., Precise and reliable gene expression via standard transcription and translation initiation elements. Nature Methods 10:354-360 (2013).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91(1):360-364 (1994).
Napolitano et al. Emergent rules for codon choice elucidated by editing rare argine codons in *Escherichia coli*. PNAS 113(38):E5588-5597 (2016).
Nawrot et al. A novel class of DNA analogs bearing 5'-C-phosphonothymidine units: synthesis and physicochemical and biochemical properties. Oligonucleotides16(1):68-82 (2006).
Needleman et al. A general method applicable to the search for similarities in the amino acid sequence of two proteins. J. Mol. Biol. 48:443-453 (1970).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al. N3'→P5' Oligodeoxyribonucleotide Phosphoramidates: A New Method of Synthesis Based on a Phosphoramidite Amine-Exchange Reaction. J Org Chem 62:7278-7287 (1997).
Nelson et al. Simultaneous detection of multiple nucleic acid targets in a homogeneous format. Biochemistry. Jun. 25, 1996;35(25):8429-38.
Neumann et al. Encoding multiple unnatural amino acids via evolution of a quadruplet-decoding ribosome Nature 464(7287):441-444 (2010).
New et al. The thieno[3,2-c]pyridine and furo[3,2-c]pyridine rings: new pharmacophores with potential antipsychotic activity. J. Med. Chem. 32:1147-1156 (1989).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nicolini et al. The FAP-IL2v Immunocytokine is a Versatile Combination Partner for Cancer Immunotherapy. Poster (SITC 2018).
Nielsen et al. Sequence-selective recognition of DNA by strand displacement with a thymine-substituted polyamide. Science 254:1497-1500 (1991).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Ostrov et al. Design, synthesis, and testing toward a 57-codon genome. Science 353(6301): 819-822 (2016).
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Parrish et al. Functional anatomy of a dsRNA trigger: differential requirement for the two trigger strands in RNA interference. Mol Cell 6(5):1077-1087 (2000).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2014/050423 International Search Report and Written Opinion dated Nov. 24, 2014.
PCT/US2015/025175 International Search Report and Written Opinion dated Oct. 13, 2015.
PCT/US2016/013095 International Search Report and Written Opinion dated Apr. 27, 2016.
PCT/US2016/067353 International Search Report and Written Opinion dated May 5, 2017.
PCT/US2017/039133 International Search Report and Written Opinion dated Sep. 20, 2017.
PCT/US2018/041503 International Search Report and Written Opinion dated Nov. 7, 2018.
PCT/US2018/041509 International Search Report and Written Opinion dated Sep. 27, 2018.
PCT/US2018/045257 International Search Report and Written Opinion dated Nov. 21, 2018.
PCT/US2018/45257 Invitation to Pay Additional Fees dated Sep. 25, 2018.
PCT/US2018/45265 International Search Report and Written Opinion dated Nov. 30, 2018.
PCT/US2018/45265 Invitation to Pay Additional Fees dated Sep. 25, 2018.
Peyrottes et al. Oligodeoxynucleoside phosphoramidates (P-NH2): synthesis and thermal stability of duplexes with DNA and RNA targets. Nucleic Acids Res 24:1841-1848 (1996).
Pfannenstiel et al. A Novel, Individualized Xenograft Model of Cancer Immunotherapy and Tumor Growth Inhibition by ALKS 4230. Poster #P351 (SITC 2017).
Piccirilli et al. A C-nucleotide base pair: methylpseudouridine-directed incorporation of formycin triphosphate into RNA catalyzed by T7 RNA polymerase. Biochemistry 30(42):10350-10356 (1991).
Piccirilli et al. Enzymatic incorporation of a new base pair into DNA and RNA extends the genetic alphabet. Nature 343:33-37 (1990).
Pieper et al. NKTR-214 in combination with radiation produces a potent in situ vaccine in the syngeneic B78 melanoma model. Poster (STIC 2018).

(56) References Cited

OTHER PUBLICATIONS

Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).

Quan et al. Circular polymerase extension cloning for high-throughput cloning of complex and combinatorial DNA libraries. Nat Protoc 6(2):242-251 (2011).

Rath et al. The CRISPR-Cas immune system: biology, mechanisms and applications. Biochimie 117:119-128 (2015).

Roessler et al. Cooperative interactions between the interleukin 2 receptor α and β chains later the interleukin 2-binding affinity of the receptor subunits. PNAS USA 91:3344-3347 (1994).

Romesberg et al. Development of a universal nucleobase and modified nucleobases for expanding the genetic code. Curr Prot Nucleic Acid Chem Chapter 1:Unit 1.5 (2002).

Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).

Sabri et al. Knock-in/Knock-out (KIKO) vectors for rapid integration of large DNA sequences, including whole metabolic pathways, onto the *Escherichia coli* chromosome at well-characterised loci. Microb Cell Fact 12:60 (2013).

Saha et al. 5'-Methyl-DNA—A New Oligonucleotide Analog: Synthesis and Biochemical Properties J Org Chem 60:788-789 (1995).

Saison-Behmoaras et al. Short modified antisense oligonucleotides directed against Ha-ras point mutation induce selective cleavage of the mRNA and inhibit T24 cells proliferation. EMBO J. 10:1111-1118 (1991).

Sakaguchi et al. Immunologic self-tolerance maintained by activated T cells expressing IL-2 receptor alpha-chains (CD25). Breakdown of a single mechanism of self-tolerance causes various autoimmune diseases. J Immunol 155(3):1151-64 1995).

Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).

Sauer. Site-specific recombination: developments and applications. Curr Opin Biotechnol 5(5):521-527 (1994).

Schlegel et al. De-convoluting the genetic adaptations of *E. coli* C41 (DE3) in real time reveals how alleviating protein production stress improves yields. Cell Rep 10:1758-1766 (2015).

Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).

Schneider et al. NIH Image to ImageJ: 25 years of image analysis. Nat Methods 9:671-675 (2012).

Schultz et al. Oligo-2'-fluoro-2'-deoxynucleotide N3'→P5' phosphoramidates: synthesis and properties. Nucleic Acids Res 24:2966-2973 (1996).

Seo et al. Improved High-Efficiency Organic Solar Cells via Incorporation of a Conjugated Polyelectrolyte Interlayer. JACS 133:8416-8419 (2011).

Seo et al. Major groove derivatization of an unnatural base pair. Chembiochem 10(14):2394-2400 (2009).

Seo et al. Optimization of an unnatural base pair toward natural-like replication. J Am Chem Soc 131:3246-3252 (2009).

Seo et al. Site-specific labeling of DNA and RNA using an efficiently replicated and transcribed class of unnatural base pairs. J Am Chem Soc 133:19878-19888 (2011).

Seo et al. Transcription of an Expanded Genetic Alphabet. JACS 131(14):5046-5047 (2009).

Shaloiko et al. Effective non-viral leader for cap-independent translation in a eukaryotic cell-free system. Biotechnology and Bioengineering 88(6):730-739 (2004).

Sharma et al. NKTR-214 enhances anti-tumor T cell immune responses induced by checkpoint blockade or vaccination. Poster (SITC 2017).

Shea et al. Synthesis, hybridization properties and antiviral activity of lipid-oligodeoxynucleotide conjugates. Nucl. Acids Res 18:3777-3783 (1990).

Shimizu et al. Cell-free translation systems for protein engineering. FEBS J 273:4133-4140 (2006).

Siegel et al. Interleukin-2 Toxicity. J Clin Oncol 9(4):694-704 (1991).

Sierzputowska-Gracz et al. Chemistry and structure of modified uridines in the anticodon, wobble position of transfer RNA are determined by thiolation. J Am Chem Soc 109:7171-7177 (1987).

Sikorski et al. A system of shuttle vectors and yeast host strains designed for efficient manipulation of DNA in *Saccharomyces cerevisiae*. Genetics 122:19-27 (1989).

Sim et al. IL2 Variant Circumvents ICOS+ Regulatory T-cell Expansion and Promotes NK Cell Activation. Cancer Immunol Res. 4(11):983-995 (Nov. 2016).

Singh et al. LNA (locked nucleic acids): synthesis and high-affinity nucleic acid recognition. Chem Commun 4:455-456 (1998).

Singh et al. Synthesis of 2'-amino-LNA: A novel conformationally restricted high-affinity oligonucleotide analogues with a handle. J Bio Chem 63:10035-10039 (1998).

Sivakumar et al. Comparison of Vascular Leak Syndrome in Mice treated with IL21 or IL2. Comparative Medicine 63(1):13-21 (2013).

Southern et al. Transformation of mammalian cells to antibiotic resistance with a bacterial gene under control of the SV40 early region promoter. J Mol Appl Genet 1:327-341 (1982).

Spangler et al. Antibodies to Interleukin-2 Elicit Selective T Cell Subset Potentiation through Distinct Conformational Mechanism. Immunity 42:815-825 (2015).

Srivastava et al. Five- and six-membered conformationally locked 2',4'-carbocyclic ribothymidines: synthesis, structure, and biochemical studies. J Am Chem Soc 129(26):8362-8379 (2007).

Stauber et al. Crystal Structure of the IL-2 signaling complex: Paradigm for a heterotrimeric cytokine receptor. PNAS 103(8):2788-2793 (2006).

Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).

Sugden et al. A vector that replicates as a plasmid and can be efficiently selected in B-lymphoblasts transformed by Epstein-Barr virus. Mol. Cell. Biol. 5:410-413 (1985).

Sun et al. First-in-Human dose Selection of ALKS 4230, an Investigational Immunotherapeutic Agent. Poster 4088 (AACR 2017).

Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).

Svinarchuk et al. Inhibition of HIV proliferation in MT-4 cells by antisense oligonucleotide conjugated to lipophilic groups. Biochimie 75:49-54 (1993).

Switzer et al. Enzymatic recognition of the base pair between isocytidine and isoguanosine. Biochemistry 32(39):10489-10496 (1993).

Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).

Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.

Synthorx, Inc. Commission File No. 001-38756. Form 8-K Current Report Pursuant to Section 13 or 15(d) of the Securities Exchange Act of 1934 dated Apr. 2, 2019 (8 pgs).

Synthorx, Inc. Commission File No. 001-38756. Form 8-K Current Report Pursuant to Section 13 or 15(d) of the Securities Exchange Act of 1934 dated May 31, 2019 (15 pgs).

Synthorx, Inc. Registration No. 333-228355. Amendment No. 1 to Form S-1 Registration Statement Under the Securities Act of 1933 filed Nov. 27, 2018 (355 pgs.).

Tae et al. Efforts toward expansion of the genetic alphabet: replication of DNA with three base pairs. J. Am. Chem. Soc. 123:7439-7440 (2001).

(56) References Cited

OTHER PUBLICATIONS

Takagi et al. Characterization of DNA polymerase from *Pyrococcus* sp. strain KOD1 and its application to PCR. Appl Environ Microbiol 63(11):4504-4510 (1997).
Takai et al. A single uridine modification at the wobble position of an artificial tRNA enhances wobbling in an *Escherichia coli* cell-free translation system. FEBS Lett 447(1):1-4 (1999).
Takeshita et al. High-copy-number and low-copy-number plasmid vectors for lacZ alpha-complementation and chloramphenicol- or kanamycin-resistance selection. Gene 61, 63-74 (1987).
Tapp et al. Homogeneous scoring of single-nucleotide polymorphisms: comparison of the 5'-nuclease TaqMan assay and Molecular Beacon probes. Biotechniques 28(4):732-738 (2000).
The Concise Encyclopedia of Polymer Science and Engineering, Kroschwitz, J.I., Ed., John Wiley & Sons pp. 858-859 (1990).
Tjalsma et al. Signal peptide-dependent protein transport in Bacillus subtilis: a genome-based survey of the secretome. Microbiol Mol Biol Rev 64(3):515-547 (2000).
Tomizawa et al. Initiation of DNA synthesis in *Escherichia coli*. Annu. Rev. Biochem. 48:999-1034 (1979).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 14/910,203 Office Action dated Feb. 5, 2019.
U.S. Appl. No. 14/910,203 Office Action dated Sep. 13, 2018.
U.S. Appl. No. 15/302,874 Office Action dated Jan. 28, 2019.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/312,901 Office Action dated May 1, 2020.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/518,715 Office Action dated Jul. 10, 2020.
U.S. Appl. No. 16/518,715 Office Action dated May 7, 2021.
U.S. Appl. No. 16/530,742, filed Aug. 2, 2019.
U.S. Appl. No. 16/530,742 Office Action dated Apr. 20, 2020.
U.S. Appl. No. 16/530,742 Office Action dated Nov. 12, 2020.
U.S. Appl. No. 16/535,992, filed Aug. 8, 2019.
U.S. Appl. No. 16/546,097, filed Aug. 20, 2019.
U.S. Appl. No. 16/546,097 Office Action dated Feb. 7, 2020.
U.S. Appl. No. 16/546,097 Office Action dated Nov. 21, 2019.
U.S. Appl. No. 16/546,100, filed Aug. 20, 2019.
U.S. Appl. No. 16/546,100 Office Action dated Feb. 7, 2020.
U.S. Appl. No. 16/546,100 Office Action dated Nov. 27, 2019.
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
U.S. Appl. No. 16/900,154, filed Jun. 12, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).

Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fc-mediated depletion of regulatory T-cells. Nat Comm 8:15373 (2017).
Verma. Retroviral vectors for gene transfer. In: Microbiology (Leive L et al., eds., Ann. Soc. Microbiol) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wan et al. Pyrrolysyl-tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. An engineered rare codon device for optimization of metabolic pathways. Scientific Reports 6:20608 (2016).
Wang et al. Biophysical and biochemical properties of oligodeoxynucleotides containing 4'-C- and 5'-C-substituted thymidines. Bioorg Med Chem Lett 9:885-890 (1999).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with its α, β, and γc Receptors. Science 310:1159-63 (2005).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).

(56) References Cited

OTHER PUBLICATIONS

Wu et al. Synthesis of Site-Specific Radiolabeled Antibodies for Radioimmunotherapy via Genetic Code Expansion. Bioconjugate Chem. 27:2460-2468 (2016).

Wurm et. al. Squaric acid mediated synthesis and biological activity of a library of linear and hyperbranched poly(glycerol)-protein conjugates. Biomacromolecules 13: 1161-1171 (2012).

Xia et al. Directed evolution of novel polymerase activities: mutation of a DNA polymerase into an efficient RNA polymerase. PNAS USA 99(10):6597-602 (2002).

Yamaguchi et al. Role of IL-5 in IL-2-induced eosinophilia. In vivo and in vitro expression of IL-5 mRNA by IL-2. J Immunol 145:873-877 (1990).

Yamashige et al. Highly specific unnatural base pair systems as a third base pair for PCR amplification. Nucleic Acids Res. 40:2793-2806 (2012).

Yan et al. Nucleoside monophosphate kinases: structure, mechanism, and substrate specificity. Adv. Enzymol. Relat. Areas Mol. Biol. 73:103-134 (1999).

Young et al. Beyond the canonical 20 amino acids: expanding the genetic lexicon. J Biol Chem 285:11039-44 (2010).

Yu et al. Polymerase recognition of unnatural base pairs. Angew Chem Int Ed Engl 41(20):3841-4 (2002).

Zalevsky. Jefferies 2016 Global Healthcare Conference. PowerPoint presentation (Nov. 16, 2016).

Zhang et al. A semisynthetic organism engineered for the stable expansion of the genetic alphabet. PNAS USA 114(6):1317-1322 (2017).

Zhang et al. A Semi-Synthetic Organism that Stores and Retrieves Increased Genetic Information. Nature 551(7682):644-647 (2017).

Zhang et al. Evolution of functional six-nucleotide DNA. J Am Chem Soc 137:6734-6737 (2015).

Zhang et al. Semisynthetic Organisms with Expanded Genetic Codes. Biochemistry 57:2177-2178 (20180.

Zhang et al. Studies of nucleoside transporters using novel autofluorescent nucleoside probes. Biochemistry 45(4):1087-1098 (2006).

Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).

Zon. Chapter 8: Oligonucleotide Phosphorothioates in Protocols for Oligonucleotides and Analogs, Synthesis and Properties. Humana Press (pp. 165-190) (1993).

Co-pending U.S. Appl. No. 17/881,471, inventors Romesberg; Floyd E. et al., filed Aug. 2, 2022.

Co-pending U.S. Appl. No. 18/112,952, inventors Romesberg; Floyd E. et al., filed Feb. 22, 2023.

Gan et al. Translation system engineering in *Escherichia coli* enhances non-canonical amino acid incorporation into proteins. Biotechnol Bioeng 114(5):1074-1086 (2017).

\* cited by examiner

INCORPORATION OF UNNATURAL NUCLEOTIDES AND METHODS THEREOF

CROSS-REFERENCE

This application is a continuation of U.S. application Ser. No. 16/629,255, filed Jan. 7, 2020, which is the U.S. National Phase entry of International Application No. PCT/US2018/041509, filed Jul. 10, 2018, which claims the benefit of U.S. Provisional Application No. 62/531,325 filed on Jul. 11, 2017, each of which is incorporated herein by reference in its entirety.

STATEMENT AS TO FEDERALLY SPONSORED RESEARCH

This invention was made with the support of the United States government under Contract number GM060005 and GM118178 to F.E.R. by National Institutes of Health and Contract number NSF/DGE-1346837 to A.W.F. by National Science Foundation Graduate Research Fellowships.

BACKGROUND OF THE INVENTION

Oligonucleotides and their applications have revolutionized biotechnology. However, the oligonucleotides including both DNA and RNA each includes only the four natural nucleotides of adenosine (A), guanosine (G), cytosine (C), thymine (T) for DNA, and the four natural nucleotides of adenosine (A), guanosine (G), cytosine (C), and uridine (U) for RNA, and which significantly restricts the potential functions and applications of the oligonucleotides.

The ability to sequence-specifically synthesize/amplify oligonucleotides (DNA or RNA) with polymerases, for example by PCR or isothermal amplification systems (e.g., transcription with T7 RNA polymerase), has revolutionized biotechnology. In addition to all of the potential applications in nanotechnology, this has enabled a diverse range of new technologies such as the in vitro evolution via SELEX (Systematic Evolution of Ligands by Exponential Enrichment) of RNA and DNA aptamers and enzymes. See, for example, Oliphant A R, Brandt C J & Struhl K (1989), Defining the sequence specificity of DNA-binding proteins by selecting binding sites from random-sequence oligonucleotides: analysis of yeast GCN4 proteins, *Mol. Cell Biol.*, 9:2944-2949; Tuerk C & Gold L (1990), Systematic evolution of ligands by exponential enrichment: RNA ligands to bacteriophage T4 DNA polymerase, *Science*, 249:505-510; Ellington A D & Szostak J W (1990), In vitro selection of RNA molecules that bind specific ligands, *Nature*, 346:818-822.

In some aspects, these applications are restricted by the limited chemical/physical diversity present in the natural genetic alphabet (the four natural nucleotides A, C, G, and T in DNA, and the four natural nucleotides A, C, G, and U in RNA). Disclosed herein is an additional method of generating nucleic acids that contains an expanded genetic alphabet.

SUMMARY OF THE INVENTION

Disclosed herein, in certain embodiments, are methods of producing a protein containing an unnatural amino acid, the method comprising: preparing a mutant tRNA wherein the mutant tRNA comprises a mutant anticodon sequence selected from Table 1 or 2; preparing a mutant mRNA wherein the mutant mRNA comprises a mutant codon sequence selected from Table 1 or 2; and synthesizing the protein containing an unnatural amino acid utilizing the mutant tRNA and the mutant mRNA. In some instances, the protein is synthesized in a cell-free translation system. In some instances, the protein is synthesized in a cell (semi-synthetic organism or SSO). In some instances, the semi-synthetic organism comprises a microorganism. In some instances, the semi-synthetic organism comprises a bacterium. In some instances, the semi-synthetic organism comprises an *Escherichia coli*. In some instances, the mutant anticodon of the mutant tRNA pairs with a mutant codon selected from Tables 1-3. In some instances, the unnatural amino acid comprises at least one unnatural nucleotide. In some instances, the unnatural nucleotide comprises an unnatural nucleobase. In some instances, the unnatural base of the unnatural nucleotide is selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-aminoadenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido [3',2':4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some instances, the unnatural nucleotide is selected from the group consisting of (only nucleobase portion shown, ribose and phosphate backbone omitted for clarity)

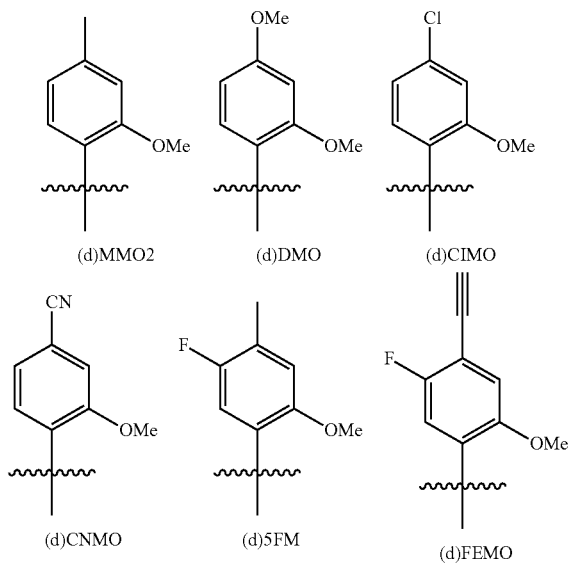

In some instances, the unnatural nucleotide is selected from the group consisting of (only nucleobase portion shown, ribose and phosphate backbone omitted for clarity)

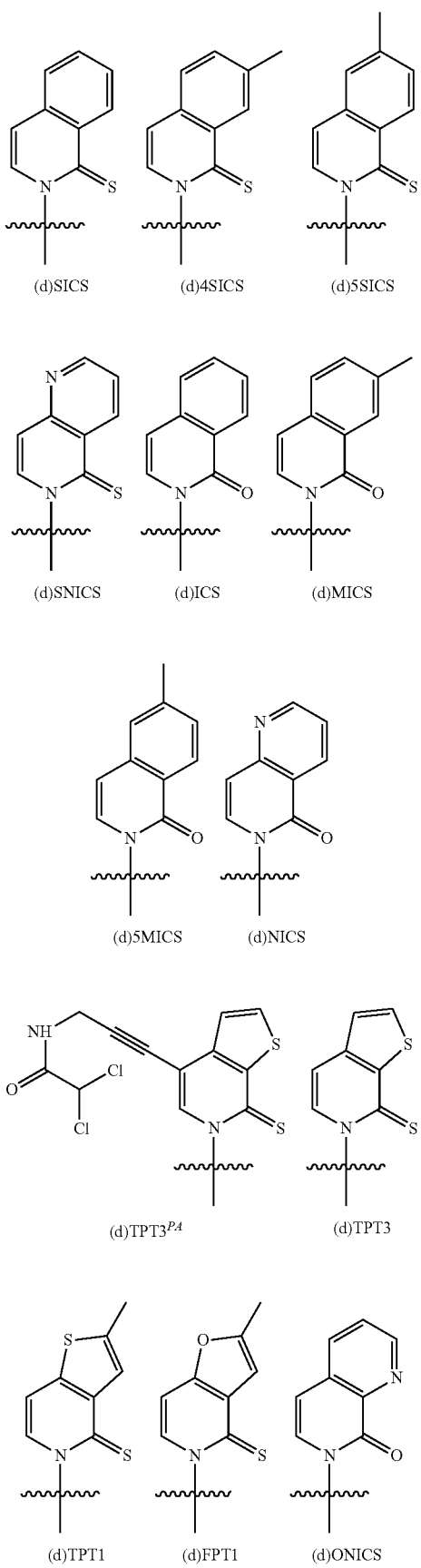

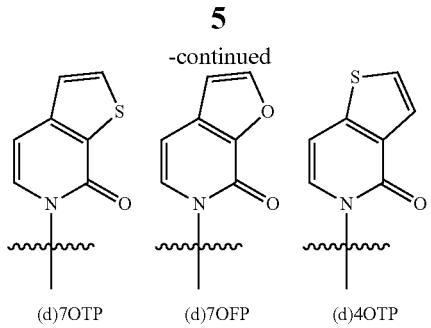

-continued (d)7OTP  (d)7OFP  (d)4OTP

In some instances, the unnatural nucleotide further comprises an unnatural sugar moiety. In some instances, the unnatural sugar moiety of the unnatural nucleotide is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some instances, the mutant anticodon or the mutant codon further comprises an unnatural backbone. In some instances, the mutant anticodon and the mutant codon further comprises an unnatural backbone. In some instances, the unnatural nucleotides are recognized by a DNA polymerase, an RNA polymerase, or a reverse transcriptase. In some instances, an unnatural nucleotide is incorporated by the RNA polymerase into the mRNA during transcription to generate a mutant mRNA containing a mutant codon. In some instances, an unnatural nucleotide is incorporated by the RNA polymerase into the tRNA during transcription to generate a mutant tRNA containing a mutant anticodon. In some instances, an unnatural nucleotide is incorporated by the RNA polymerase into the mRNA during transcription to generate a mutant mRNA. In some instances, an unnatural nucleotide is incorporated by the RNA polymerase into the tRNA during transcription to generate a mutant tRNA. In some instances, the mutant tRNA is charged with an unnatural amino acid residue. In some instances, a protein containing an unnatural amino acid is generated during translation utilizing the mutant tRNA and the mutant mRNA.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

Figure 1A:
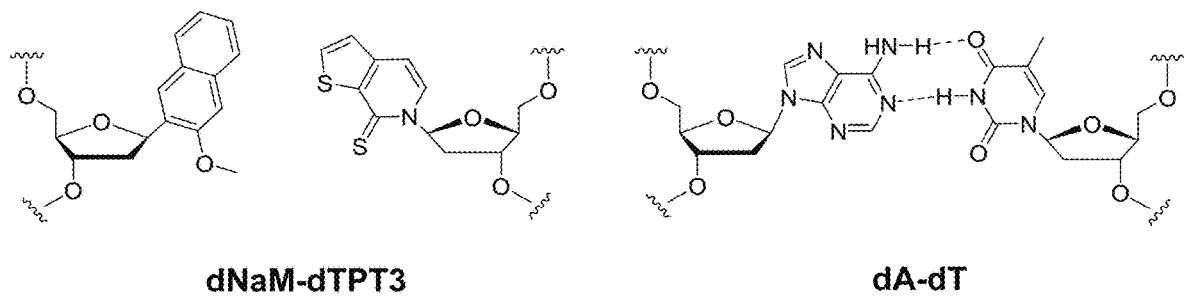
FIG. 1A illustrates the chemical structure of the dNaM-dTPT3 UBP and a natural dA-dT base pair.

Table 5|UBP retention. Retention of the UBP(s) in plasmids with the indicated position-151 codons of sfGFP and anticodons of the indicated tRNAs were determined for a time point prior to sfGFP induction and at the end of induction, as described in Methods. The reported values are the mean UBP retention over the course of the induction (calculated from the retentions at these two time points) ±95% CI, n=4 cultures, each propagated from an individual colony, except for values indicated with an asterisk, for which n=3. n/a, not applicable (because the relevant sequence is natural or absent). All plasmids were isolated from cultures grown in the presence of 20 mM PrK or 5 mMpAzF (except for Ser decoding experiments). SerRS indicates charging with the endogenous *E. coli* synthetase. Minus sign denotes the absence of PylRS in cells with tRNA$^{Pyl}$ or the absence of an ectopically expressed tRNA. Retentions in rows indicated with § correspond to cultures from which sfGFP was also purified and analyzed by LC-MS/MS and/or western blot of TAMRA-conjugated sfGFP (see FIG. 1F (Ser), FIG. 2D (PrK), and FIG. 3B (pAzF)); rows with an asterisk correspond to the cultures analyzed in FIGS. 7A-D. Despite the fact that all four unnatural triphosphates enter the cell through the same transporter and thus competitively inhibit one another's import, no differences in UBP retention were observed with the presence (+) or absence (−) of NaMTP and/or TPT3TP in the media. These data, and the requirement of both unnatural ribotriphosphates for high levels of sfGFP expression with high-fidelity PrK incorporation (FIGS. 7A-D), collectively demonstrate that the expression level of the PtNTT2 transporter in YZ3 imports the requisite levels of unnatural triphosphates necessary to sustain UBP replication and transcription.

Table 6|Yields of sfGFP protein expressed in Ser, Prk and pAzF incorporation experiments. Yields were calculated from the total amount of protein purified and the volume of culture used for purification (see Methods). Data are mean±s.d. (n=4 sfGFP samples, each purified from a culture propagated from an individual colony) and were determined from the same cultures analyzed in FIG. 1F (for SerRS) and FIG. 2D (for PylRS), as well as the cultures corresponding to the (+) pAzF samples in FIG. 3A (for pAzFRS). Yields of purified sfGFP are comparable to the mean total fluorescence (not normalized to OD$_{600}$) of the cultures from which they were purified. Fluorescence values correspond to the time point at which cells were collected for sfGFP purification; see FIG. 1C (Ser), FIG. 2B (PrK), and FIG. 3A (pAzF).

DETAILED DESCRIPTION OF THE INVENTION

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

Overview

The information of life is encoded by a four letter genetic alphabet, which is made possible by the selective formation of two base pairs: (d)G-(d)C and (d)A-dT/U. A third, unnatural base pair (UBP) formed between two synthetic nucleotides expands this system, thereby increasing the potential for information storage, and has profound academic and practical implications. Of the wide variety of synthetic nucleotide analogs that have been reported, several pair stably with one another within an otherwise natural DNA duplex, but are not recognized by polymerases, and indicating that the forces governing stable pairing in duplex DNA are not the same as those governing polymerase-mediated replication. As a result, different approaches have been taken to develop replicable UBPs, for example, UBPs that are designed to interact via complementary hydrogen bonding (H-bonding) patterns not employed by the natural nucleotides. Although the natural base pairs form via H-bonding, there is no reason to assume a priori that H-bonding is the only force sufficient to underlie the storage (or retrieval) of genetic information. For example, it has been demonstrated that the Klenow fragment of *E. coli* DNA polymerase I (Kf) pairs dA with the unnatural nucleotide dF, whose difluorotoluene nucleobase is a shape mimic of thymine that is incapable of significant H-bonding. This supports a "geometrical selection" mechanism of DNA replication and suggests that forces other than H-bonding also contribute to replication.

The development of UBPs that are replicated, transcribed, and translated into protein in vitro provide insights into the forces underlying the storage and retrieval of natural information, and also enable wide ranging applications in chemical and synthetic biology. However, the ultimate goal of many efforts to develop UBPs is their in vivo use as the foundation of a semi-synthetic organism (SSO)—an organism that stably stores and retrieves increased (un-natural or synthetic, meaning man made) information. Moreover, such an SSO has revolutionary practical applications, including for human health. Most notably, an SSO revolutionizes the growing field of protein therapeutics. However, compared to traditional small molecule therapeutics, protein therapeutics are severely limited in their molecular properties due to the finite chemical diversity available with the twenty natural amino acids.

We recently reported the creation of an *E. coli* SSO that by virtue of a nucleoside triphosphate transporter from *Phaeodactylum tricornutum* (PtNTT2), imports the requisite unnatural triphosphates from the media and then uses them to replicate a plasmid containing the UBP dNaM-dTPT3. We have since shown that DNA containing the UBP may be transcribed in the SSO by T7 RNA polymerase, and that when an unnatural nucleotide is incorporated into the codon of an mRNA, different tRNAs charged with ncAAs and containing the cognate unnatural nucleotide in their anticodon, can efficiently and selectively decode the unnatural codon. Because the UBP may be combined at different positions of different codons, this suggests that the UBP may be used to encode proteins with multiple, different ncAAs.

Disclosed herein in certain embodiments are methods, compositions, and kits for the synthesis of proteins which comprises unnatural amino acids that utilizes a mutant tRNA. In some instances, the protein is synthesized in a cell-free translation system. In some instances, the protein is synthesized in a cell or semi-synthetic organism (SSO). In some instances, the semi-synthetic organism comprises a microorganism. In some instances, the semi-synthetic organism comprises a bacterium. In some instances, the semi-synthetic organism comprises an *Escherichia coli*. In some instances, the mutant tRNA contains a mutant anticodon sequence. In some instances, the mutant anticodon sequence is an anticodon sequence illustrated in Table 1. In some instances, the mutant anticodon sequence is an anticodon sequence illustrated in Table 2. In some instances, the mutant anticodon sequence is an anticodon sequence illustrated in Table 3.

TABLE 1

| | | |
|---|---|---|
| GGY | GYG | YGG |
| GAY | GYA | YGA |
| GCY | GYC | YGC |
| GUY | GYU | YGU |
| CAY | CYA | YCA |
| CGY | CYG | YCG |
| CUY | CYU | YCU |
| CCY | CYC | YCC |
| AAY | AYA | YAA |
| AGY | AYG | YAG |
| ACY | AYC | YAC |
| AUY | AYU | YAU |
| UUY | UYU | YUU |
| UAY | UYA | YUA |
| UGY | UYG | YUG |
| UCY | UYC | YUC |
| GYY | YGY | YYG |
| CYY | YCY | YYC |
| AYY | YAY | YYA |
| UYY | YUY | YYU |
| YYY | | |

TABLE 2

| | | |
|---|---|---|
| GGX | GXG | XGG |
| GAX | GXA | XGA |
| GCX | GXC | XGC |
| GUX | GXU | XGU |
| CAX | CXA | XCA |
| CGX | CXG | XCG |
| CUX | CXU | XCU |
| CCX | CXC | XCC |
| AAX | AXA | XAA |
| AGX | AXG | XAG |
| ACX | AXC | XAC |
| AUX | AXU | XAU |
| UUX | UXU | XUU |
| UAX | UXA | XUA |
| UGX | UXG | XUG |
| UCX | UXC | XUC |
| GXX | XGX | XXG |
| CXX | XCX | XXC |
| AXX | XAX | XXA |
| UXX | XUX | XXU |
| XXX | | |

TABLE 3

| | | |
|---|---|---|
| GXY | GYX | XYG |
| YXG | XGY | YGX |
| AXY | AYX | XYA |
| YXA | XAY | YAX |
| CXY | CYX | XYC |
| YXC | XCY | YCX |
| UXY | UYX | XYU |
| YXU | XUY | YUX |
| XYY | XXY | YXX |
| YXX | YXY | XYX |

In some instances, the mutant anticodon of the mutant tRNA pairs with a mutant codon. In some embodiments, the mutant codon is a mutant codon illustrated in Table 1. In some embodiments, the mutant codon is a mutant codon illustrated in Table 2. In some embodiments, the mutant codon is a mutant codon illustrated in Table 3.

In some embodiments, the Y and X illustrated in Table 1, Table 2, and Table 3 represent unnatural bases of the unnatural nucleotide. In some embodiments, the unnatural base is selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; $N_4$-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, $N_6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-$N_6$-isopentenyladenine, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

In some instances, the unnatural nucleotide is selected from the group consisting of (only nucleobase portion shown, ribose and phosphate backbone omitted for clarity)

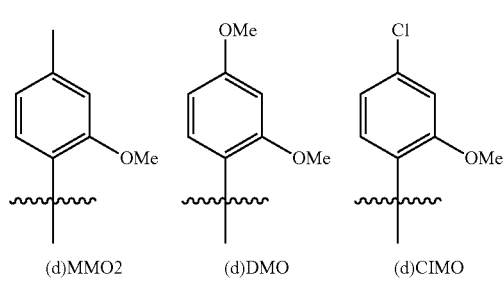

In some instances, the unnatural nucleotide is selected from the group consisting of (only nucleobase portion shown, ribose and phosphate backbone omitted for clarity)

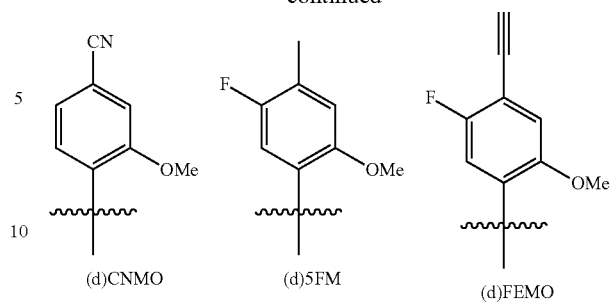

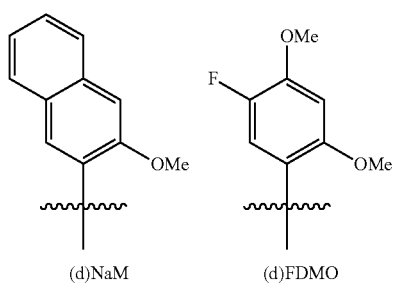

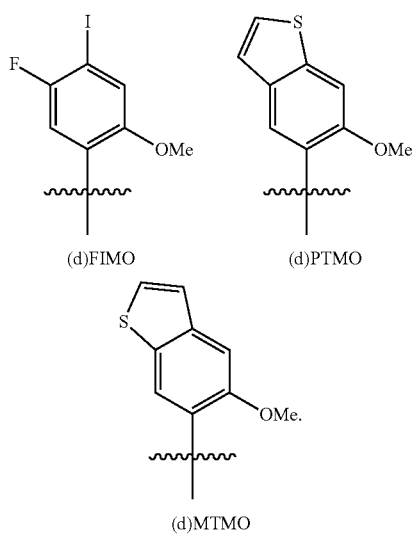

In some instances, the unnatural nucleotide is selected from the group consisting of (only nucleobase portion shown, ribose and phosphate backbone omitted for clarity)

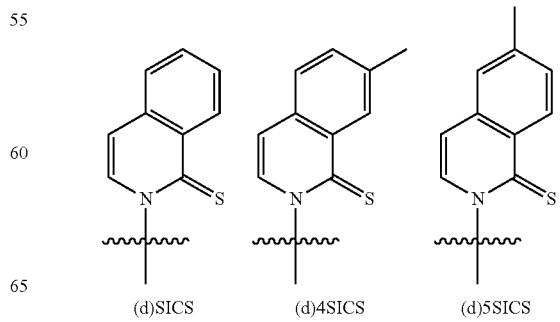

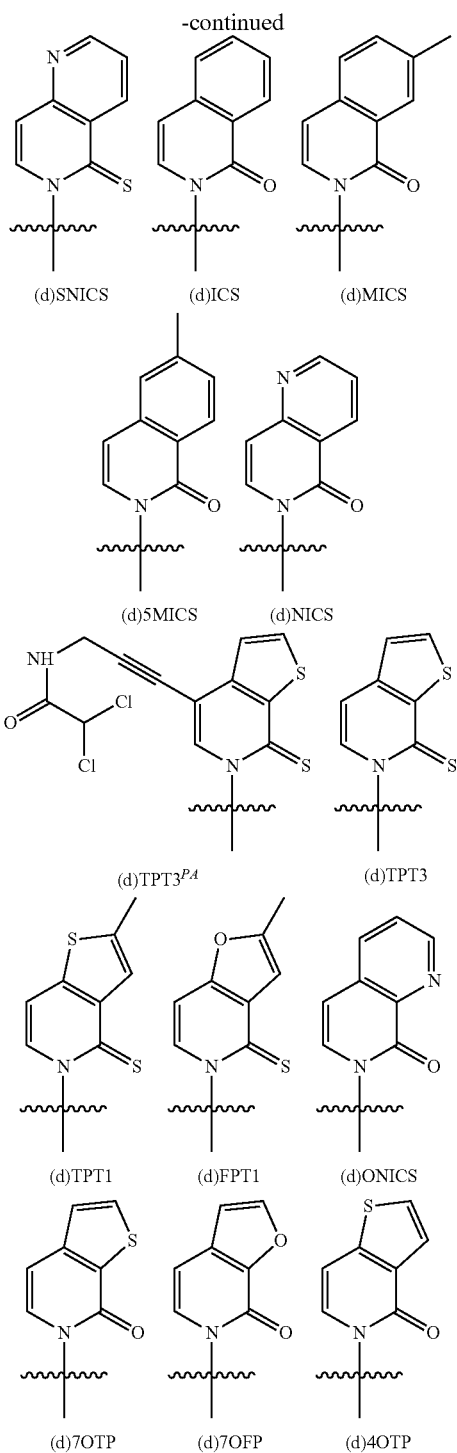

O]mCH₃, —O(CH₂)nOCH₃, —O(CH₂)n NH₂, —O(CH₂)n CH₃, —O(CH₂)n —ONH₂, and —O(CH₂)nON[(CH₂)n CH₃)]2, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some instances, the mutant anticodon or the mutant codon further comprises an unnatural backbone. In some instances, the mutant anticodon further comprises an unnatural backbone. In some instances, the mutant codon further comprises an unnatural backbone. In some instances, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

In some instances, the unnatural nucleotides are recognized by a polymerase. In some instances, the polymerase is a DNA polymerase, an RNA polymerase, or a reverse transcriptase. In some instances, the polymerase comprises Φ29, B103, GA-1, PZA, Φ15, BS32, M2Y, Nf, Gl, Cp-1, PRD1, PZE, SFS, Cp-5, Cp-7, PR4, PR5, PR722, L17, ThermoSequenase®, 9° Nm™ Terminator™ DNA polymerase, Tne, Tma, TfI, Tth, Tli, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some instances, the polymerase is DNA polymerase 1-Klenow fragment, Vent polymerase, Phusion® DNA polymerase, KOD DNA polymerase, Taq polymerase, T7 DNA polymerase, T7 RNA polymerase, Terminator™ DNA polymerase, POLB polymerase, SP6 RNA polymerase, *E. coli* DNA polymerase I, *E. coli* DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

In some instances, an unnatural nucleotide is incorporated by the polymerase into the mRNA during transcription to generate a mutant mRNA containing a mutant codon. In some instances, an unnatural nucleotide is incorporated by the polymerase into the mRNA during transcription to generate a mutant mRNA.

In some instances, an unnatural nucleotide is incorporated by the polymerase into the tRNA during transcription to generate a mutant tRNA containing a mutant anticodon. In some instances, an unnatural nucleotide is incorporated by the polymerase into the tRNA during transcription to generate a mutant tRNA.

In some instances, the mutant tRNA represents an unnatural amino acid residue. In some instances, an unnatural In some instances, the unnatural nucleotide further comprises an unnatural sugar moiety. In some instances, the unnatural sugar moiety is selected from the group consisting of a modification at the 2' position: OH; substituted lower alkyl, alkaryl, aralkyl, O-alkaryl or O-aralkyl, SH, SCH₃, OCN, Cl, Br, CN, CF₃, OCF₃, SOCH₃, SO₂ CH₃, ONO₂, NO₂, N₃, NH₂F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH₃, 2'-O(CH₂)₂OCH₃ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, —O[(CH₂)n amino acid residue is a non-natural amino acid such as those described in Liu C. C., Schultz, P. G. *Annu. Rev. Biochem.* 2010, 79, 413.

In some instances, a protein containing an unnatural amino acid is generated during translation utilizing the mutant tRNA and the mutant mRNA. In some instances, the protein containing an unnatural amino acid is generated under a cell free translation system. In some instances, the protein is synthesized in a cell or semi-synthetic organism (SSO). In some instances, the semi-synthetic organism comprises a microorganism. In some instances, the semi-synthetic organism comprises a bacterium. In some instances, the semi-synthetic organism comprises an *Escherichia coli*.

Nucleic Acids

A nucleic acid (e.g., also referred to herein as target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). Nucleic acids can comprise nucleotides, nucleosides, or polynucleotides. Nucleic acids can comprise natural and unnatural nucleic acids. A nucleic acid can also comprise unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phage, autonomously replicating sequence (ARS), centromere, artificial chromosome, yeast artificial chromosome (e.g., YAC) or other nucleic acid able to replicate or be replicated. An unnatural nucleic acid can be a nucleic acid analogue.

Unnatural Nucleic Acids

A nucleotide analog, or unnatural nucleotide, comprises a nucleotide which contains some type of modification to either the base, sugar, or phosphate moieties. A modification can comprise a chemical modification. Modifications may be, for example, of the 3'OH or 5'OH group, of the backbone, of the sugar component, or of the nucleotide base. Modifications may include addition of non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect a modified backbone comprises a backbone other than a phosphodiester backbone. In one aspect a modified sugar comprises a sugar other than deoxyribose (in modified DNA) or other than ribose (modified RNA). In one aspect a modified base comprises a base other than adenine, guanine, cytosine or thymine (in modified DNA) or a base other than adenine, guanine, cytosine or uracil (in modified RNA).

The nucleic acid may comprise at least one modified base. Modifications to the base moiety would include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes but is not limited to uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and O-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH¼) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232;

5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al. (2001) Bioorg. Med. Chem. 9:807-813; The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; and Sanghvi, Y. S., Chapter 15, Antisense Research and Applications, Crooke, S. T. and Lebleu, B., Eds., CRC Press, 1993, 273-288. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993.

Unnatural nucleic acids comprising various heterocyclic bases and various sugar moieties (and sugar analogs) are available in the art, and the nucleic acid can include one or several heterocyclic bases other than the principal five base components of naturally-occurring nucleic acids. For example, the heterocyclic base may include uracil-5-yl, cytosin-5-yl, adenin-7-yl, adenin-8-yl, guanin-7-yl, guanin-8-yl, 4-aminopyrrolo[2.3-d] pyrimidin-5-yl, 2-amino-4-oxopyrolo [2, 3-d] pyrimidin-5-yl, 2-amino-4-oxopyrrolo [2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Unnatural nucleic acids can include 2',3'-dideoxy-2',3'-didehydro-nucleosides (PCT/US2002/006460), 5'-substituted DNA and RNA derivatives (PCT/US2011/033961; Saha et al, J. Org Chem., 1995, 60, 788-789; Wang et al, Bioorganic & Medicinal Chemistry Letters, 1999, 9, 885-890; and Mikhailov et al, Nucleosides & Nucleotides, 1991, 10(1-3), 339-343; Leonid et al, 1995, 14(3-5), 901-905; and Eppacher et al, Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al, Nucleosides Nucleotides & Nucleic Acids, 2004, 23 (1 & 2), 317-337).

Unnatural nucleic acids can include modifications at the 5'-position and the 2'-position of the sugar ring (PCT/US94/02993), such as 5'-$CH_2$ substituted 2'-O-protected nucleosides (Wu et al., Helvetica Chimica Acta, 2000, 83, 1127-1143 and Wu et al. Bioconjugate Chem. 1999, 10, 921-924). Unnatural nucleic acids can include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al, Synlett, 1997, 1287-1290). Unnatural nucleic acids can include 2'-substituted 5'-$CH_2$ (or O) modified nucleosides (PCT/US92/01020). Unnatural nucleic acids can include 5'methylenephosphonate DNA and RNA monomers, and dimers (Bohringer et al, Tet. Lett., 1993, 34, 2723-2726; Collingwood et al, Synlett, 1995, 7, 703-705; and Hutter et al, Helvetica Chimica Acta, 2002, 85, 2777-2806). Unnatural nucleic acids can include 5'-phosphonate monomers having a 2'-substitution (US 2006/0074035) and other modified 5'-phosphonate monomers (WO 97/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and or 6' position (Chen et al, Phosphorus, Sulfur and Silicon, 2002, 777, 1783-1786; Jung et al, Bioorg. Med. Chem., 2000, 8, 2501-2509, Gallier et al, Eur. J. Org. Chem., 2007, 925-933 and Hampton et al, J. Med. Chem., 1976, 19(8), 1029-1033). Unnatural nucleic acids can include 5'-phosphonate deoxyribonucleoside monomers and dimers having a 5'-phosphate group (Nawrot et al, Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al, Synlett, 2001, 4, 467-472; Kappler et al, J. Med. Chem., 1986, 29, 1030-1038 and J. Med. Chem., 1982, 25, 1179-1184; Vrudhula et al, J. Med. Chem., 1987, 30, 888-894; Hampton et al, J. Med. Chem., 1976, 19, 1371-1377; Geze et al, J. Am. Chem. Soc, 1983, 105(26), 7638-7640 and Hampton et al, J. Am. Chem. Soc, 1973, 95(13), 4404-4414)

Unnatural nucleic acids can also include modifications of the sugar moiety. Nucleic acids of the invention can optionally contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R=H, $C_1$-$C_{12}$ alkyl or a protecting group); and combinations thereof. Examples of chemically modified sugars can be found in WO 2008/101157, US 2005/0130923, and WO 2007/134181.

A modified nucleic acid may comprise modified sugars or sugar analogs. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include, 2'-O-methyl-uridine and 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[($CH_2$)$_n$ O]$_m$ $CH_3$, —O($CH_2$)$_n$ $OCH_3$, —O($CH_2$)$_n$ $NH_2$, —O($CH_2$)$_n$ $CH_3$, —O($CH_2$)$_n$—$ONH_2$, and —O($CH_2$)$_n$ON[($CH_2$)$_n$ $CH_3$)J$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety, which detail and describe a range of base modifications. Each of these patents is herein incorporated by reference.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—C $C_{10}$ alkyl, $OCF_3$, O($CH_2$)$_2$$SCH_3$, O($CH_2$)$_2$—O—N ($R_m$)($R_n$), and O—$CH_2$—C(=O)—N($R_m$)($R_n$), where each $R_m$ and $R_n$ is, independently, H or substituted or unsubstituted $C_1$-$C_{10}$ alkyl.

In certain embodiments, nucleic acids of the present invention include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845, issued on Jul. 15, 2008); 4'-C(CH$_3$)(CH$_3$)—O-2' and analogs thereof, (see WO2009/006478, WO2008/150729, US2004/0171570, U.S. Pat. No. 7,427,672, Chattopadhyaya, et al, J. Org. Chem., 2 09, 74, 118-134), and WO 2008/154401, published on Dec. 8, 2008). Also see, for example: Singh et al., Chem. Commun., 1998, 4, 455-456; Koshkin et al, Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al, J. Am. Chem. Soc, 129(26) 8362-8379 (Jul. 4, 2007); Elayadi et al, Curr. Opinion Invens. Drugs, 2001, 2, 558-561; Braasch et al, Chem. Biol, 2001, 8, 1-7; Oram et al, Curr. Opinion Mol Ther., 2001, 3, 239-243; U.S. Pat. Nos. 7,053,207, 6,268,490, 6,770,748, 6,794,499, 7,034,133, 6,525,191, 6,670,461, and 7,399,845; International applications WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT US2008/066154, and PCT US2008/068922, PCT/DK98/00393; and U.S. Pat. Nos. 4,849,513; 5,015,733; 5,118,800; and 5,118,802.

In certain embodiments, nucleic acids can comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—CH$_2$—N(CH$_3$)—O—CH$_2$—), thiodiester (—O—C(O)—S—), thionocarbamate (—O— C(O)(NH)—S—); siloxane (—O—Si(H)2-O—); and N,N*-dimethylhydrazine (—CH$_2$—N(CH$_3$)—N(CH$_3$)—). In certain embodiments, inter nucleic acids linkages having a chiral atom can be prepared a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

A phosphorous derivative (or modified phosphate group) can be attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al. (1996) Nucleic Acids Res. 24: 1841-1848; Chaturvedi et al. (1996) Nucleic Acids Res. 24:2318-2323; and Schultz et al. (1996) Nucleic Acids Res. 24:2966-2973; Matteucci (1997) "Oligonucleotide Analogs: an Overview" in Oligonucleotides as Therapeutic Agents, (DJ. Chadwick and G. Cardew, ed.) John Wiley and Sons, New York, N.Y.; (Zon (1993) "Oligonucleoside Phosphorothioates" in Protocols for Oligonucleotides and Analogs, Synthesis and Properties (Agrawal, ed.) Humana Press, pp. 165-190); (Miller et al. (1971) JACS 93:6657-6665); (Jager et al. (1988) Biochem. 27:7247-7246), (Nelson et al. (1997) JOC 62:7278-7287) (U.S. Pat. No. 5,453,496); Micklefield, J. 2001, Current Medicinal Chemistry 8: 1157-1179.

Backbone modification may comprise replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene(methylimino) linkages; formacetal and thioformacetal linkages; backbones containing sulfonyl groups; morpholino oligos; peptide nucleic acids (PNA); and positively charged deoxyribonucleic guanidine (DNG) oligos, Micklefield, J. 2001, Current Medicinal Chemistry 8: 1157-1179. A modified nucleic acid may comprise a chimeric or mixed backbone comprising one or more modifications, e.g. a combination of phosphate linkages such as a combination of phosphodiester and phosphorothioate linkages.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500). Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Polymerase

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

In some instances, disclosed herein includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3 to 5' exonuclease proofreading activity or where a 3 to 5' exonuclease proofreading activity has been disabled, e.g. through mutation. Examples of DNA polymerases include polA, polB (see e.g. Parrel & Loeb, Nature Struc Biol 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In a related aspect, the invention provides methods of making a modified polymerase that include structurally modeling a parental polymerase, e.g., a DNA polymerase, identifying one or more complex stability or nucleotide interaction feature affecting complex stability or nucleotide access or binding in the active site or a complementarity feature for a nucleotide analog at the active site, and mutating the parental polymerase to include or remove these features. For example, the polymerase can be mutated to improve steric access of the unnatural nucleotide to the active site or to improve charge-charge or hydrophobic interactions between the unnatural nucleotide and the polymerase. The methods also include determining whether the resulting modified polymerase displays an increased incorporation of a nucleotide or unnatural nucleotide into a growing nucleic acid copy as compared to the parental polymerase.

Polymerases can be characterized according to their rate of dissociation from nucleic acids. In some embodiments, a polymerase has a relatively low dissociation rate for one or more natural and unnatural nucleic acids. In some embodiments, a polymerase has a relatively high dissociation rate for one or more natural and unnatural nucleic acids. The dissociation rate is an activity of a polymerase that can be adjusted to tune reaction rates in methods set forth herein.

Polymerases can be characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of $(k_{cat}/K_m)$ for the natural and unnatural nucleic acid and $(k_{cat}/K_m)$ for the incorrect natural and unnatural nucleic acid; where $k_{cat}$ and $K_m$ are Michaelis-Menten parameters in steady state enzyme kinetics (Fersht, A. R. (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1 \times 10^6$, with or without a proofreading activity.

Polymerases from native sources or variants thereof can be screened using an assay that detects incorporation of an unnatural nucleic acid having a particular structure. In one example, polymerases can be screened for the ability to incorporate an unnatural nucleic acid or UBP; e.g., d5SICSTP, dNaMTP, or d5SICSTP-dNaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., dTPT3, dNaM analog, or dTPT3-dNaM UBP into nucleic acids. In some embodiments, such an assay is an in vitro assay, e.g., using a recombinant polymerase variant. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, Gl, Cp-1, PRD1, PZE, SFS, Cp-5, Cp-7, PR4, PR5, PR722, or L17 polymerase.

Nucleic acid polymerases generally useful in the invention include DNA polymerases, RNA polymerases, reverse transcriptases, and mutant or altered forms thereof. DNA polymerases and their properties are described in detail in, among other places, DNA Replication 2$^{nd}$ edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), Thermus thermophilus (Tth) DNA polymerase (Myers and Gelfand 1991, Biochemistry 30:7661), Bacillus stearothermophilus DNA polymerase (Stenesh and McGowan, 1977, Biochim Biophys Acta 475:32), *Thermococcus litoralis* (Tli) DNA polymerase (also referred to as Vent™ DNA polymerase, Cariello et al, 1991, *Polynucleotides Res*, 19: 4193, New England Biolabs), 9° Nm™ DNA polymerase (New England Biolabs), Stoffel fragment, Thermo Sequenase® (Amersham Pharmacia Biotech UK), Terminator™ (New England Biolabs), *Thermotoga maritima* (Tma) DNA polymerase (Diaz and Sabino, 1998 Braz *J Med. Res*, 31:1239), *Thermus aquaticus* (Taq) DNA polymerase (Chien et al, 1976, *J. Bacteriol*, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al, 1981, J Biol. Chem. 256:3112), and archaeal DP1I/DP2 DNA polymerase II (Cann et al, 1998, Proc. Natl. Acad. Sci.

USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, TfI, Tth, TIi, Stoffel fragment, Vent™ and Deep Vent™ DNA polymerase, KOD DNA polymerase, Tgo, JDF-3, and mutants, variants and derivatives thereof. A polymerase that is a 3 exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al, CRC Crit Rev Biochem. 3:289-347(1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase Gardner et al. (2004) "Comparative Kinetics of Nucleotide Analog Incorporation by Vent DNA Polymerase (J. Biol. Chem., 279(12), 11834-11842; Gardner and Jack "Determinants of nucleotide sugar recognition in an archaeon DNA polymerase" Nucleic Acids Research, 27(12) 2545-2553.) Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

In some embodiments, the polymerase comprises Φ29, B103, GA-1, PZA, Φ15, BS32, M2Y, Nf, Gl, Cp-1, PRD1, PZE, SFS, Cp-5, Cp-7, PR4, PR5, PR722, L17, ThermoSequenase®, 9° Nm™, Therminator™ DNA polymerase, Tne, Tma, TfI, Tth, TIi, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, E. coli DNA polymerase I, E. coli DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some embodiments, the polymerase is DNA polymerase 1-Klenow fragment, Vent polymerase, Phusion® DNA polymerase, KOD DNA polymerase, Taq polymerase, T7 DNA polymerase, T7 RNA polymerase, Therminator™ DNA polymerase, POLB polymerase, SP6 RNA polymerase, E. coli DNA polymerase I, E. coli DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Since at least the last common ancestor of all life on earth, genetic information has been stored in a four-letter alphabet that is propagated and retrieved by the formation of two base pairs. The central goal of synthetic biology is to create new life forms and functions, and the most general route to this goal is the creation of semi-synthetic organisms (SSOs) whose DNA harbors two additional letters that form a third, unnatural base pair (UBP). Previously, our efforts to generate such SSOs culminated in the creation of a strain of *Escherichia coli* that by virtue of a nucleoside triphosphate transporter from *Phaeodactylum tricornutum* (PtNTT2), imports the requisite unnatural triphosphates from the media and then uses them to replicate a plasmid containing the UBP dNaM-dTPT3 (FIG. 1A). While the SSO stores increased information, it did not retrieve it, which requires in vivo transcription of the UBP into mRNA and tRNA, aminoacylation of the tRNA with an unnatural amino acid, and finally, efficient participation of the UBP in decoding at the ribosome. Here, we report the in vivo transcription of DNA containing dNaM and dTPT3 into mRNAs with two different unnatural codons and tRNAs with cognate unnatural anticodons, and their efficient decoding at the ribosome to direct the site-specific incorporation of natural or non-canonical amino acids (ncAAs) into superfolder green fluorescent protein (sfGFP). The results demonstrate that interactions other than hydrogen bonding can contribute to every step of information storage and retrieval. The resulting SSO both encodes and retrieves increased information and should serve as a platform for the creation of new life forms and functions.

Figure 1B:
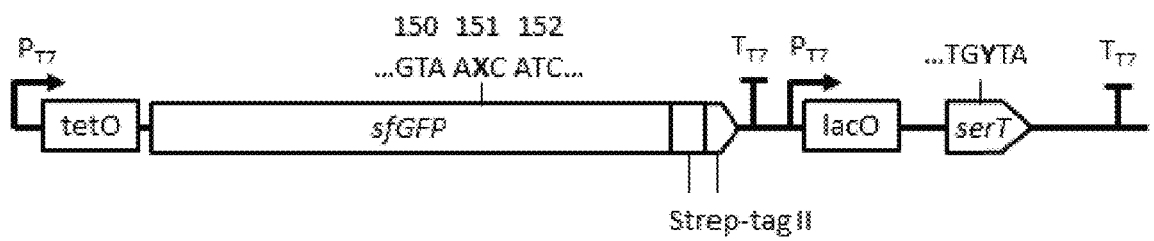
FIG. 1B illustrates the gene cassette used to express sfGFP(AXC)[151] and tRNA(GYT)$^{Ser}$. $P_{T7}$ and $T_{T7}$ denote the T7 RNAP promoter and terminator, respectively. In controls where sfGFP is expressed in the absence of serT, the sequence following the sfGFP T7 terminator is absent.
Figure 4:
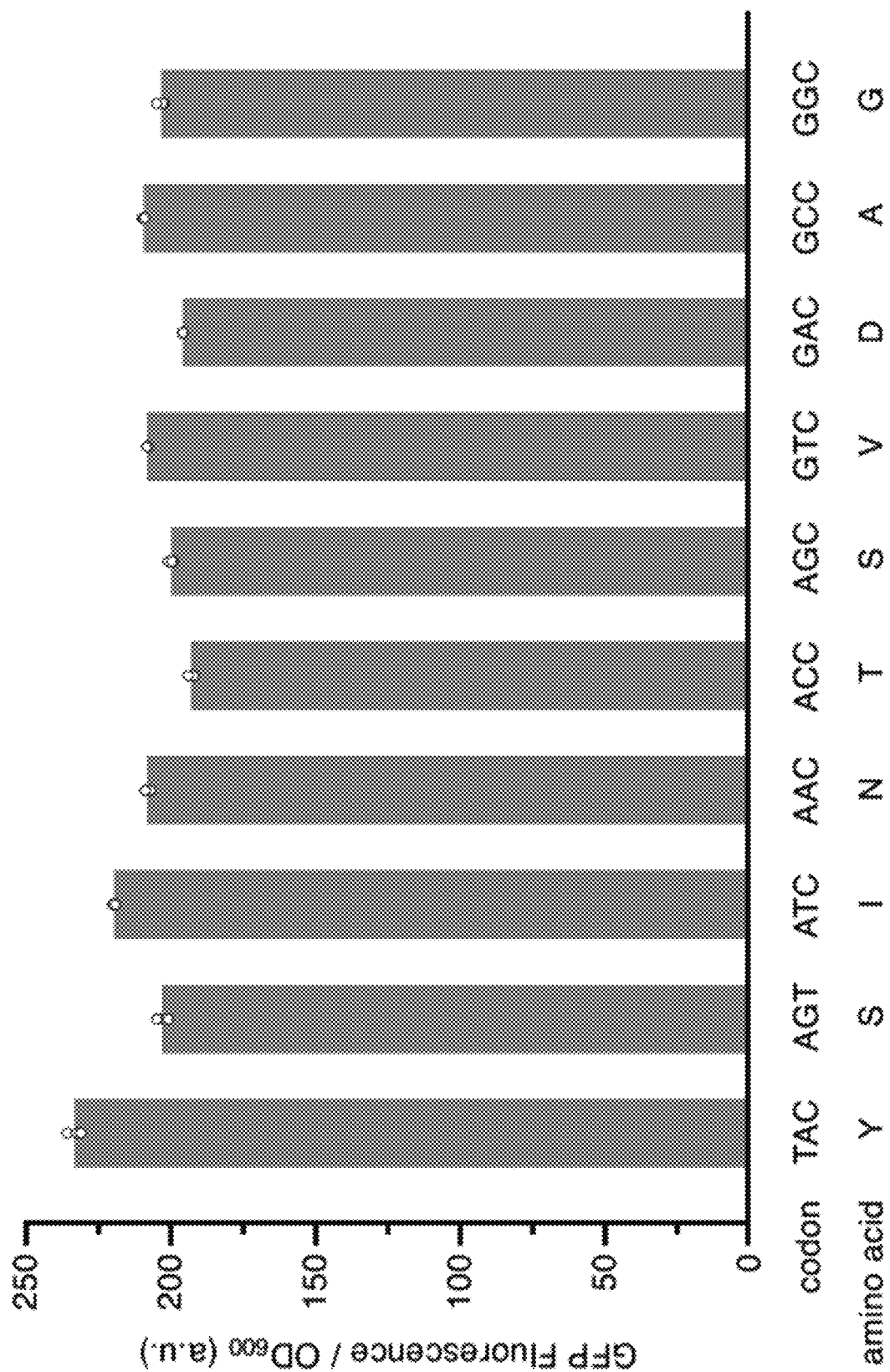
FIG. 4 illustrates fluorescence of cells expressing sfGFP with various codons at position 151. Cells carrying a sfGFP plasmid with the indicated position-151 codons were grown to an OD$_{600}$~0.5 and induced with IPTG and aTc. Fluorescence measurements were taken after 3 h of induction. Data shown as mean with individual data points, n=3 cultures split from a single colony and grown in parallel.

Green fluorescent protein and variants such as sfGFP have served as model systems for the study of ncAA incorporation using the amber suppression system, including at position Y151, which has been shown to tolerate a variety of natural and ncAAs (FIG. 4). To explore the decoding of unnatural codons, we first focused on the incorporation of Ser at position 151 of sfGFP, as *E. coli* serine aminoacyl-tRNA synthetase (SerRS) does not rely on anticodon recognition for tRNA aminoacylation, thus eliminating the potential complications of inefficient charging. SSO strain YZ3 was transformed with a plasmid encoding sfGFP and an *E. coli* tRNA$^{Ser}$ gene (serT), with sfGFP codon 151 (TAC) replaced by the unnatural codon AXC (sfGFP(AXC)$^{151}$; X=NaM), and the anticodon of serT replaced by the unnatural anticodon GYT (tRNA$^{Ser}$ (GYT); Y=TPT3) (FIG. 1B). Transformants were grown in media supplemented with dNaMTP and dTPT3TP, then supplemented further with NaMTP and TPT3TP, as well as isopropyl-β-D-thiogalactoside (IPTG) to induce expression of T7 RNA polymerase (T7 RNAP) and tRNA$^{Ser}$ (GYT). After a brief period of tRNA induction, anhydrotetracycline (aTc) was added to induce expression of sfGFP(AXC)$^{151}$.

Figure 1C:
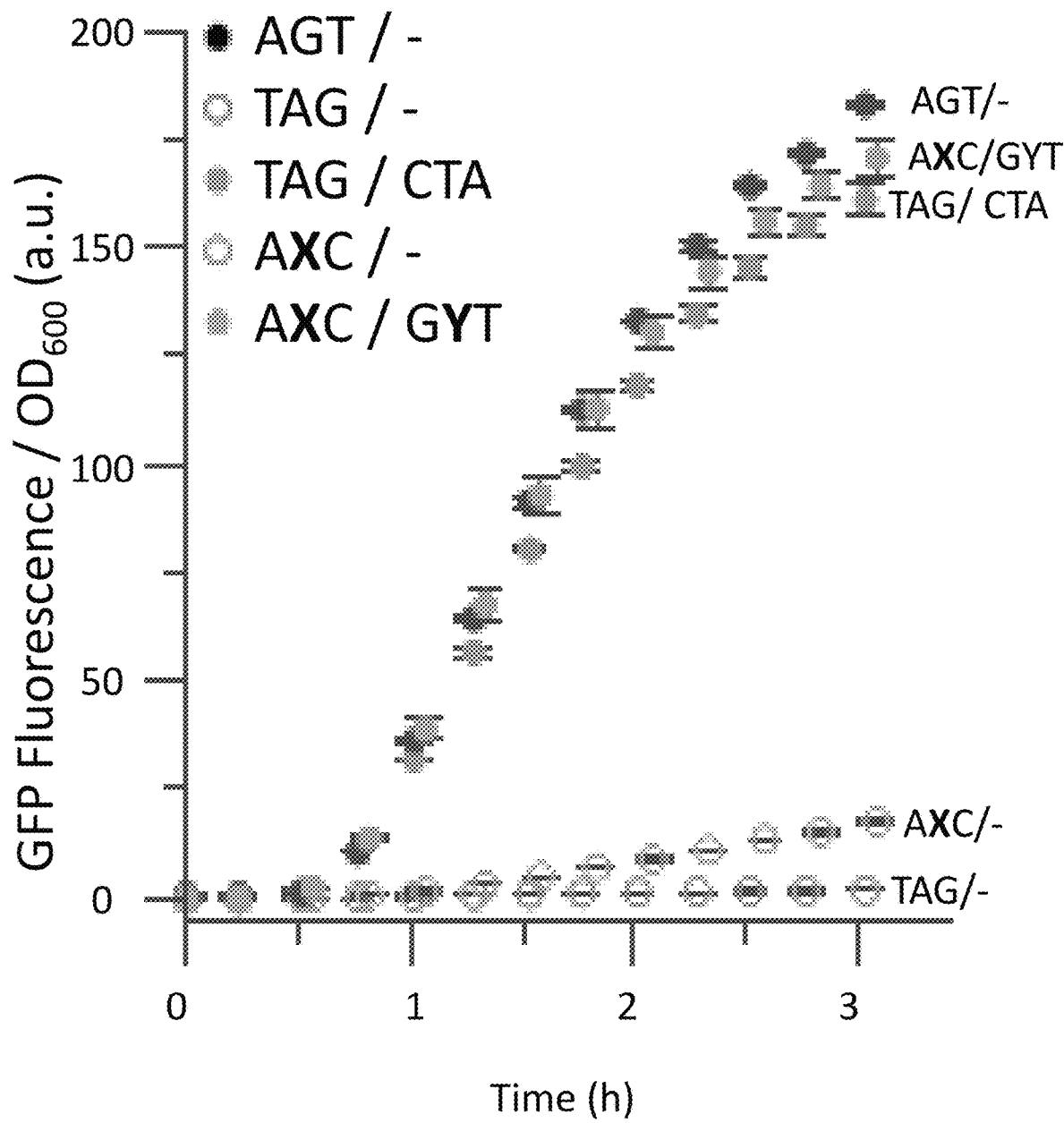
FIG. 1C illustrates a graph of fluorescence of cells expressing sfGFP and tRNA$^{Ser}$ with the indicated position 151-codon and anticodon, respectively. Minus sign denotes the absence of serT in the expression cassette. t=0 corresponds to the addition of IPTG to induce expression of T7 RNAP and tRNA$^{Ser}$ (if present); aTc was added at t=0.5 h to induce expression of sfGFP. AGT, natural Ser codon; TAG, amber stop codon; CTA amber suppressor anticodon. Data shown as mean±s.d., n=4 cultures, each propagated from an individual colony.
Figure 1D:
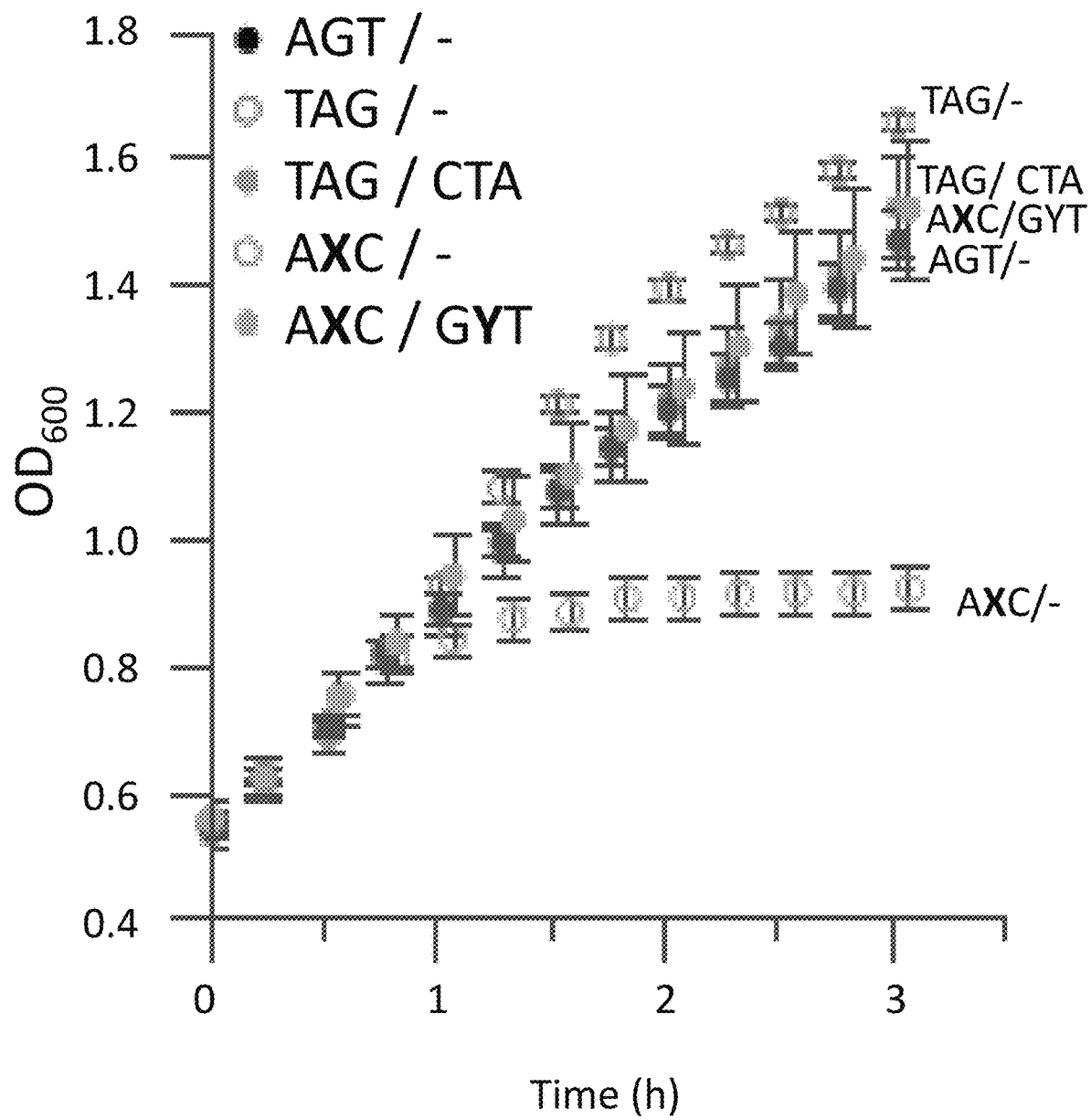
FIG. 1D illustrates a graph of growth of cells expressing sfGFP and tRNA$^{Ser}$ with the indicated position 151-codon and anticodon, respectively. Minus sign denotes the absence of serT in the expression cassette. t=0 corresponds to the addition of IPTG to induce expression of T7 RNAP and tRNA$^{Ser}$ (if present); aTc was added at t=0.5 h to induce expression of sfGFP. AGT, natural Ser codon; TAG, amber stop codon; CTA amber suppressor anticodon. Data shown as mean±s.d., n=4 cultures, each propagated from an individual colony.
Figure 1E:
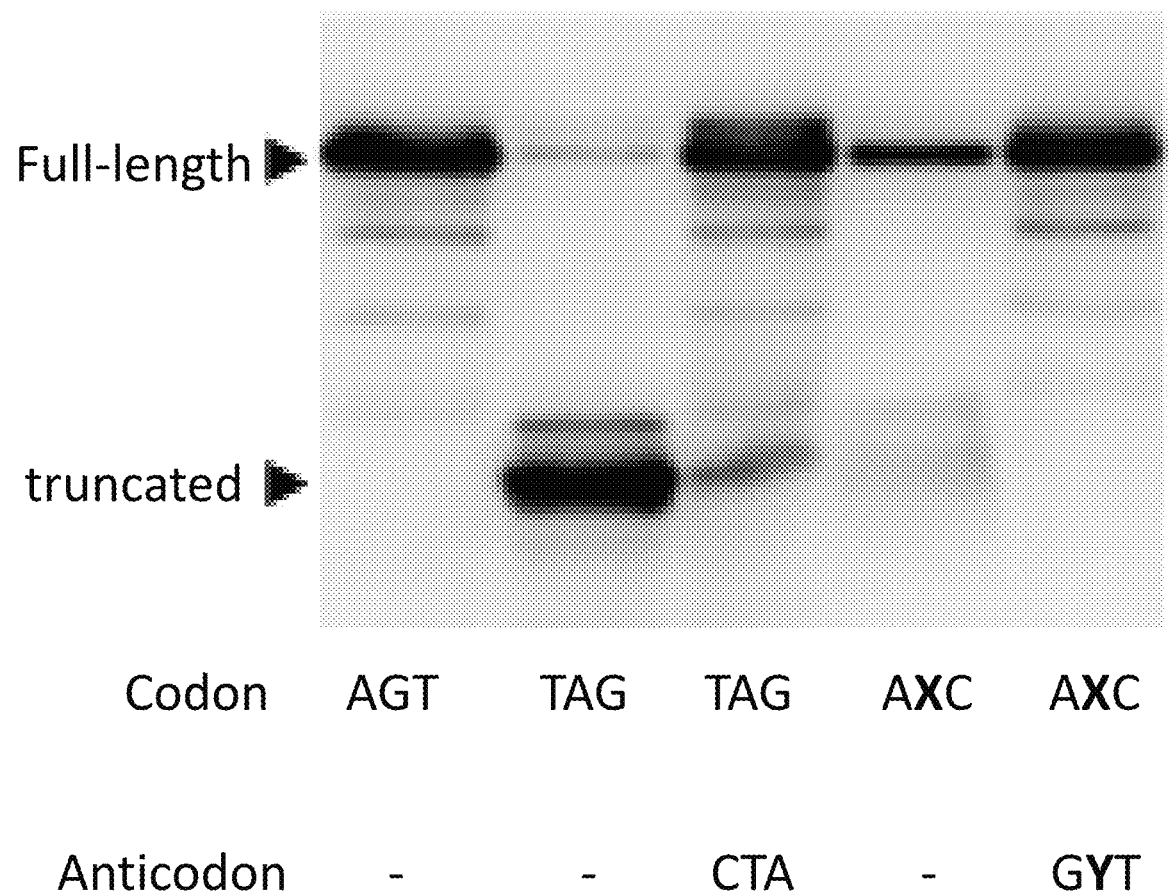
FIG. 1E illustrates a Western blot of lysates (normalized by OD$_{600}$) from cells collected at the last time point shown in FIG. 1C and FIG. 1D, probed with an α-GFP antibody (N-terminal epitope).
Figure 5A:
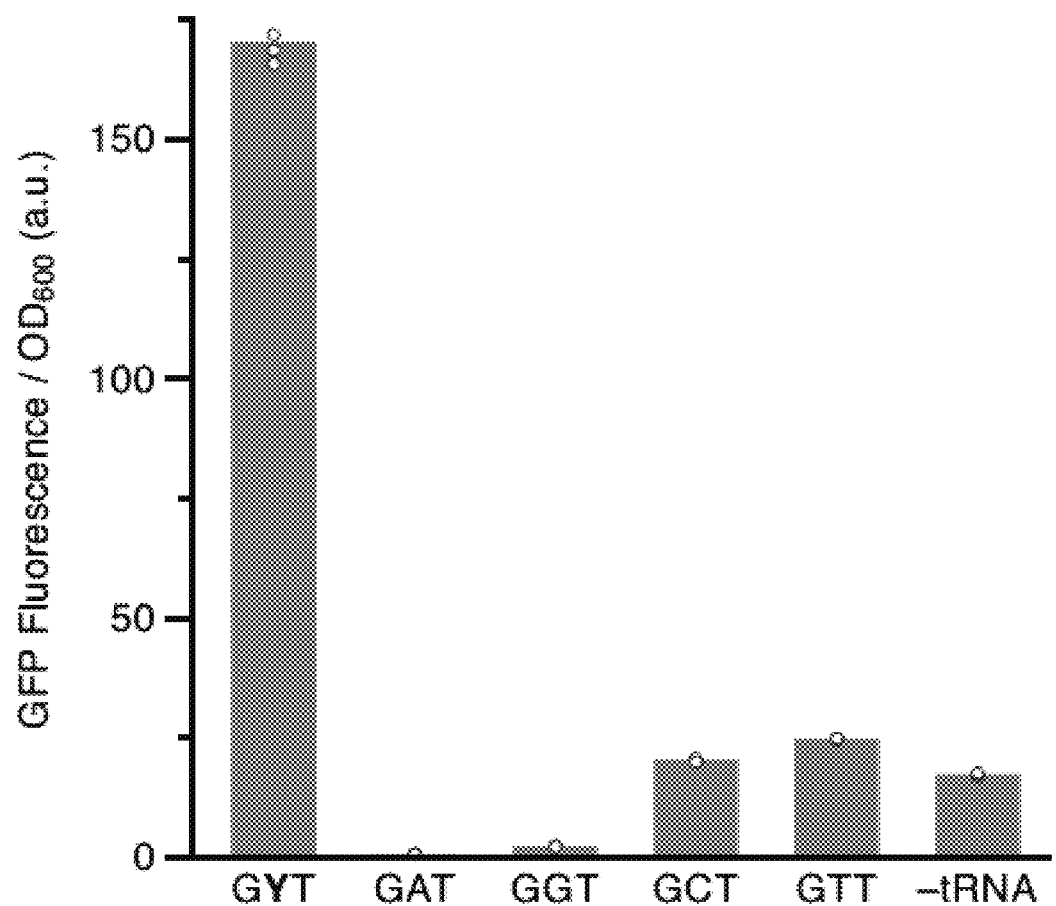
FIG. 5A illustrates decoding of the AXC codon with natural near-cognate anticodons, with a graph of fluorescence of cells expressing sfGFP(AXC)$^{151}$ with or without tRNA$^{Ser}$ with the indicated anticodon. Cells were induced as described in FIG. 1C and FIG. 1D and fluorescence measurements correspond to the last time point shown in FIG. 1C. Values for the GYT anticodon and in the absence of tRNA$^{Ser}$ (−tRNA) correspond to the same values in FIG. 1c,d. Data shown as mean±s.d., n=4 cultures, each propagated from an individual colony.
Figure 5B:
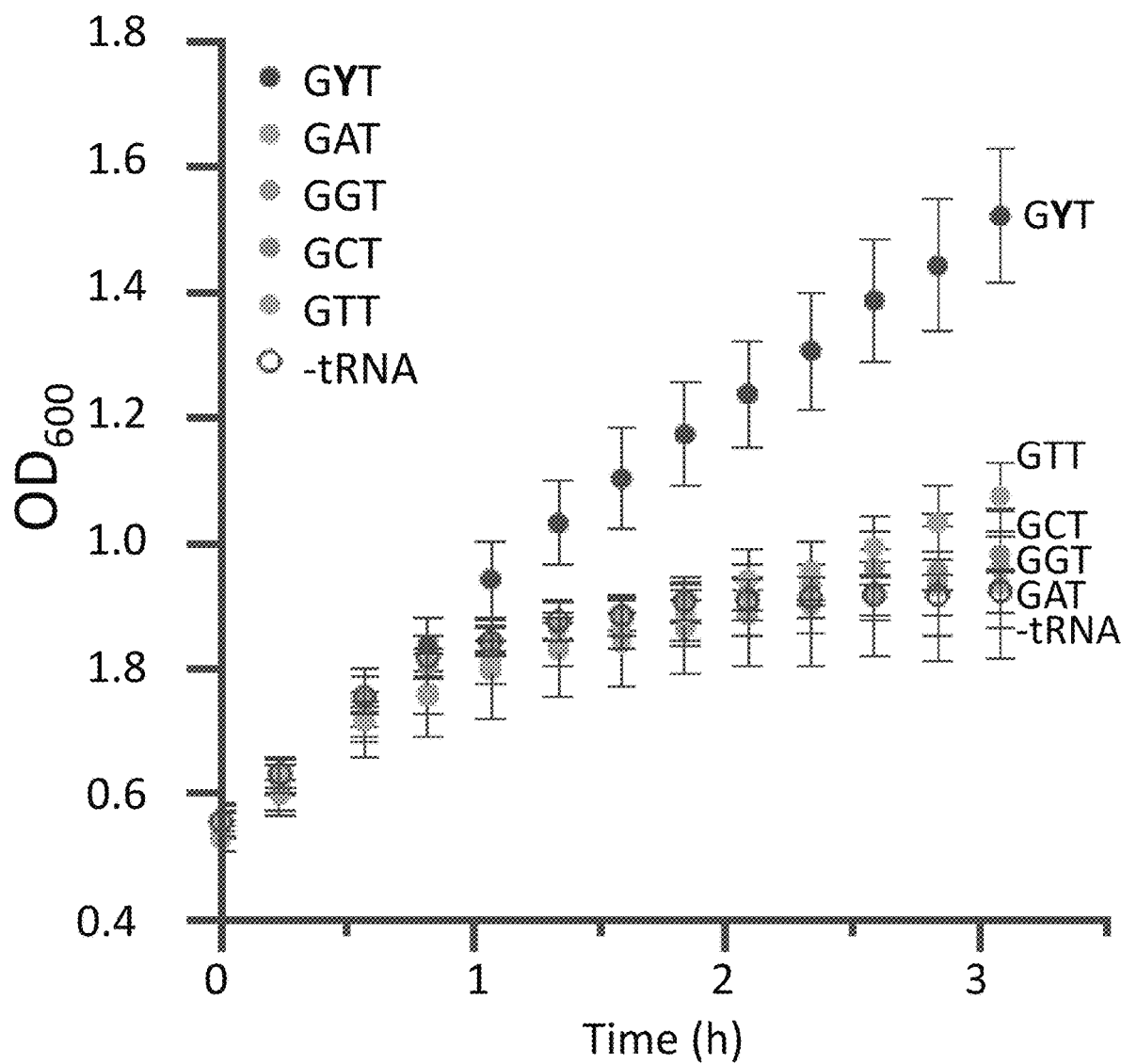
FIG. 5B illustrates decoding of the AXC codon with natural near-cognate anticodons, with a graph of growth of cells expressing sfGFP(AXC)$^{151}$ with or without tRNA$^{Ser}$ with the indicated anticodon. Cells were induced as described in FIG. 1C and FIG. 1D and fluorescence measurements correspond to the last time point shown in FIG. 1C. Values for the GYT anticodon and in the absence of tRNA$^{Ser}$ (−tRNA) correspond to the same values in FIG. 1C and FIG. 1D. Data shown as mean±s.d., n=4 cultures, each propagated from an individual colony.

Following induction, cells transformed with a control plasmid encoding sfGFP(AXC)$^{151}$ but lacking tRNA$^{Ser}$ (GYT) showed dramatically reduced fluorescence compared to cells transformed with a plasmid encoding sfGFP with a natural Ser codon at position 151 (sfGFP(AGT)$^{151}$; FIG. 1C). Moreover, cell growth began to plateau upon induction of sfGFP(AXC)$^{151}$ (FIG. 1D), likely due to the stalling and sequestering of ribosomes. Lysates of these cells were subjected to western blotting with an anti-GFP antibody, which revealed a significant reduction in sfGFP expression and the presence of sfGFP truncated at the position of the unnatural codon (FIG. 1E). In contrast, cells transformed with the plasmid encoding both sfGFP(AXC)[151] and tRNA[Ser] (GYT) exhibited fluorescence that was nearly equal to that of control cells expressing sfGFP(AGT)[151] (FIG. 1C), cell growth did not plateau upon induction of sfGFP (AXC)[151] (FIG. 1D), and western blots of lysates from these cells revealed only full-length sfGFP protein (FIG. 1E). Furthermore, we assessed the ability of all four natural near-cognate tRNAs (tRNA[Ser](GNT); N=G, C, A, or T), expressed in an identical fashion, to decode the AXC codon. In each case, little fluorescence was observed and the growth defect remained (FIGS. 5A and 5B). These data demonstrate that PtNTT2 is able to import both the deoxy- and ribotriphosphates of both unnatural nucleotides, that T7 RNA polymerase is able to transcribe mRNA and tRNA containing the unnatural nucleotides in vivo, and that the ribosome only efficiently decodes the unnatural codon with an unnatural anticodon.

Figure 1F:
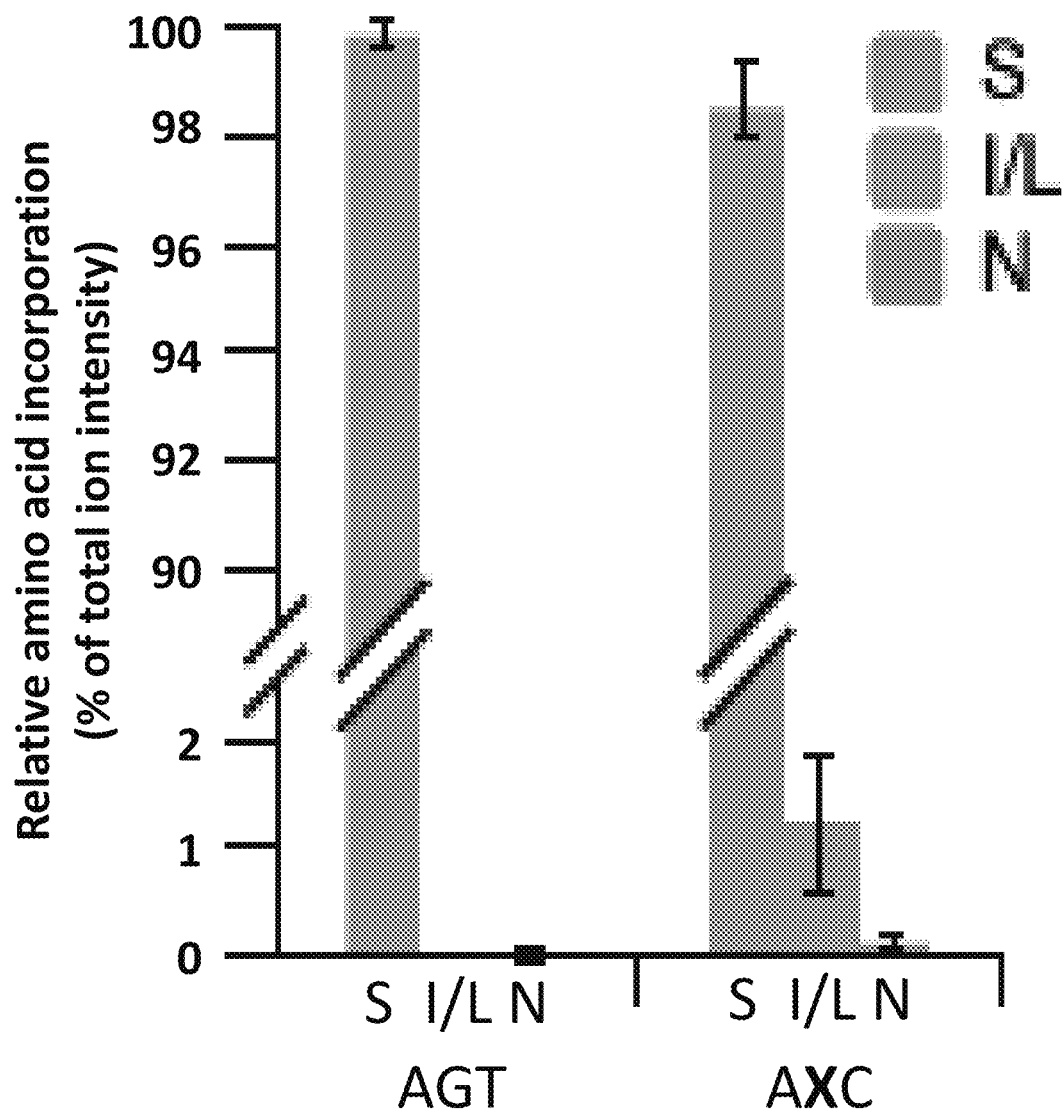
FIG. 1F illustrates a graph of the relative abundance of the amino acids (indicated by their single letter codes in the figure legend) detected at position 151 of sfGFP purified from cells expressing sfGFP(AGT)[151] or sfGFP(AXC)[151] and tRNA$^{Ser}$ (GYT), as determined by LC-MS/MS and precursor ion intensity based quantitation (amino acids detected at <0.1% (on average, for both codons) are not shown; see Methods for details and Table 4 for a complete list of amino acids detected). Data shown as mean with individual data points, n=4 purified sfGFP samples, each from a culture propagated from an individual colony and collected at the last time point shown in FIG. 1C and FIG. 1D.

To assess the fidelity of decoding, we analyzed protein purified from cells expressing both sfGFP(AXC)[151] and tRNA[Ser](GYT) via LC/MS-MS and relative quantitation via peak intensities, which revealed a 98.5±0.7% (95% CI, n=4) incorporation of Ser at position 151, with Ile/Leu being the predominant contaminant (FIG. 1F, Table 4). Given that the retention of the UBP in the sfGFP(AXC)[151] gene was 98±2% (95% CI, n=4) (Table 5) and that X→T is typically the major mutation during replication (which for AXC would result in the Ile codon ATC), we attribute the majority of the protein not containing Ser at position 151 to loss of the UBP during replication and conclude that the fidelity of translation with the unnatural codon is high.

TABLE 4

| Sample | Relative MS1 ion intensities (%) | | | | | | | | | |
|---|---|---|---|---|---|---|---|---|---|---|
| | S | Y | PrK | I/L | N | V | K | G | C | M |
| sfGFP(AGT)[151] | 99.80 | 0.03 | 0.06 | 0.00 | 0.04 | 0.03 | 0.00 | 0.02 | 0.02 | 0.00 |
| sfGFP(AXC)[151]/tRNA[Ser](GYT) | 98.47 | 0.04 | 0.04 | 1.23 | 0.14 | 0.02 | 0.00 | 0.05 | 0.01 | 0.00 |
| sfGFP(TAC)[151] | 0.11 | 99.71 | 0.06 | 0.00 | 0.05 | 0.02 | 0.00 | 0.02 | 0.02 | 0.01 |
| sfGFP(TAG)[151]/tRNA[Pyl](CTA) | 0.06 | 0.04 | 99.53 | 0.00 | 0.04 | 0.01 | 0.29 | 0.01 | 0.01 | 0.00 |
| sfGFP(AXC)[151]/tRNA[Pyl](GYT) | 0.25 | 0.03 | 96.16 | 2.06 | 1.06 | 0.02 | 0.37 | 0.03 | 0.01 | 0.00 |
| sfGFP(GXC)[151]/tRNA[Pyl](GYC) | 0.06 | 0.04 | 97.50 | 0.00 | 0.01 | 1.26 | 0.74 | 0.37 | 0.01 | 0.00 |

| Sample | 95% CI (%) | | | | | | | | | |
|---|---|---|---|---|---|---|---|---|---|---|
| | S | Y | PrK | I/L | N | V | K | G | C | M |
| sfGFP(AGT)[151] | 0.31 | 0.04 | 0.09 | 0.00 | 0.06 | 0.05 | 0.01 | 0.03 | 0.03 | 0.00 |
| sfGFP(AXC)[151]/tRNA[Ser](GYT) | 0.73 | 0.04 | 0.03 | 0.64 | 0.04 | 0.01 | 0.00 | 0.04 | 0.01 | 0.00 |
| sfGFP(TAC)[151] | 0.06 | 0.11 | 0.05 | 0.00 | 0.03 | 0.02 | 0.00 | 0.01 | 0.02 | 0.00 |
| sfGFP(TAG)[151]/tRNA[Pyl](CTA) | 0.03 | 0.02 | 0.11 | 0.00 | 0.02 | 0.02 | 0.03 | 0.01 | 0.01 | 0.00 |
| sfGFP(AXC)[151]/tRNA[Pyl](GYT) | 0.13 | 0.02 | 0.25 | 0.06 | 0.03 | 0.01 | 0.06 | 0.01 | 0.02 | 0.01 |
| sfGFP(GXC)[151]/tRNA[Pyl](GYC) | 0.05 | 0.04 | 0.70 | 0.00 | 0.01 | 0.24 | 0.28 | 0.22 | 0.01 | 0.00 |

TABLE 5

| aaRS | tRNA | NaMTP | TPT3TP | Codon | % UBP Retention sfGFP | Anti. codon | % UBP Retention in tRNA gene |
|---|---|---|---|---|---|---|---|
| SerRS | — | + | + | AXC | 98 ± 0 | — | n/a |
| SerRS§ | Ser | + | + | AXC | 98 ± 2 | GYT | 89 ± 2 |
| SerRS | Ser | + | + | AXC | 94 ± 8 | GAT | n/a |
| SerRS | Ser | + | + | AXC | 94 ± 2 | GGT | n/a |
| SerRS | Ser | + | + | AXC | 95 ± 0 | GCT | n/a |
| SerRS | Ser | + | + | AXC | 95 ± 1 | GTT | n/a |
| — | Pyl | + | + | AXC | 97 ± 1 | GYT | 89 ± 2 |
| PylRS | — | + | + | AXC | 97 ± 1 | — | n/a |
| PylRS | Pyl | + | + | TAC | n/a | GYT | 92 ± 3 |
| PylRS§ | Pyl | + | + | AXC | 96 ± 1 | GYT | 90 ± 2 |
| PylRS* | Pyl | + | + | AXC | 98 ± 0 | GYT | 95 ± 2 |
| PylRS* | Pyl | + | − | AXC | 98 ± 1 | GYT | 96 ± 1 |
| PylRS* | Pyl | − | + | AXC | 98 ± 1 | GYT | 95 ± 1 |
| PylRS* | Pyl | − | − | AXC | 97 ± 1 | GYT | 94 ± 4 |
| — | Pyl | + | + | GXC | 98 ± 1 | GYC | 96 ± 3 |
| PylRS | — | + | + | GXC | 97 ± 3 | — | n/a |
| PylRS | Pyl | + | + | TAC | n/a | GYC | 96 ± 1 |
| PylRS§ | Pyl | + | + | GXC | 97 ± 1 | GYC | 95 ± C |
| PylRS* | Pyl | + | + | GXC | 96 ± 3 | GYC | 97 ± 1 |
| PylRS* | Pyl | + | − | GXC | 96 ± 2 | GYC | 97 ± 1 |
| PylRS* | Pyl | − | + | GXC | 97 ± 2 | GYC | 97 ± 0 |
| PylRS* | Pyl | − | − | GXC | 96 ± 1 | GYC | 97 ± 1 |
| pAzFRS RS§ | pAzF | + | + | AXC | 98 ± 0 | GYT | 90 ± 1 |
| pAzFRS RS | pAzF | + | + | TAC | n/a | GYT | 91 ± 1 |

*Corresponds to the cultures analyzed in FIGS. 7A-7D.

Figure 2A:
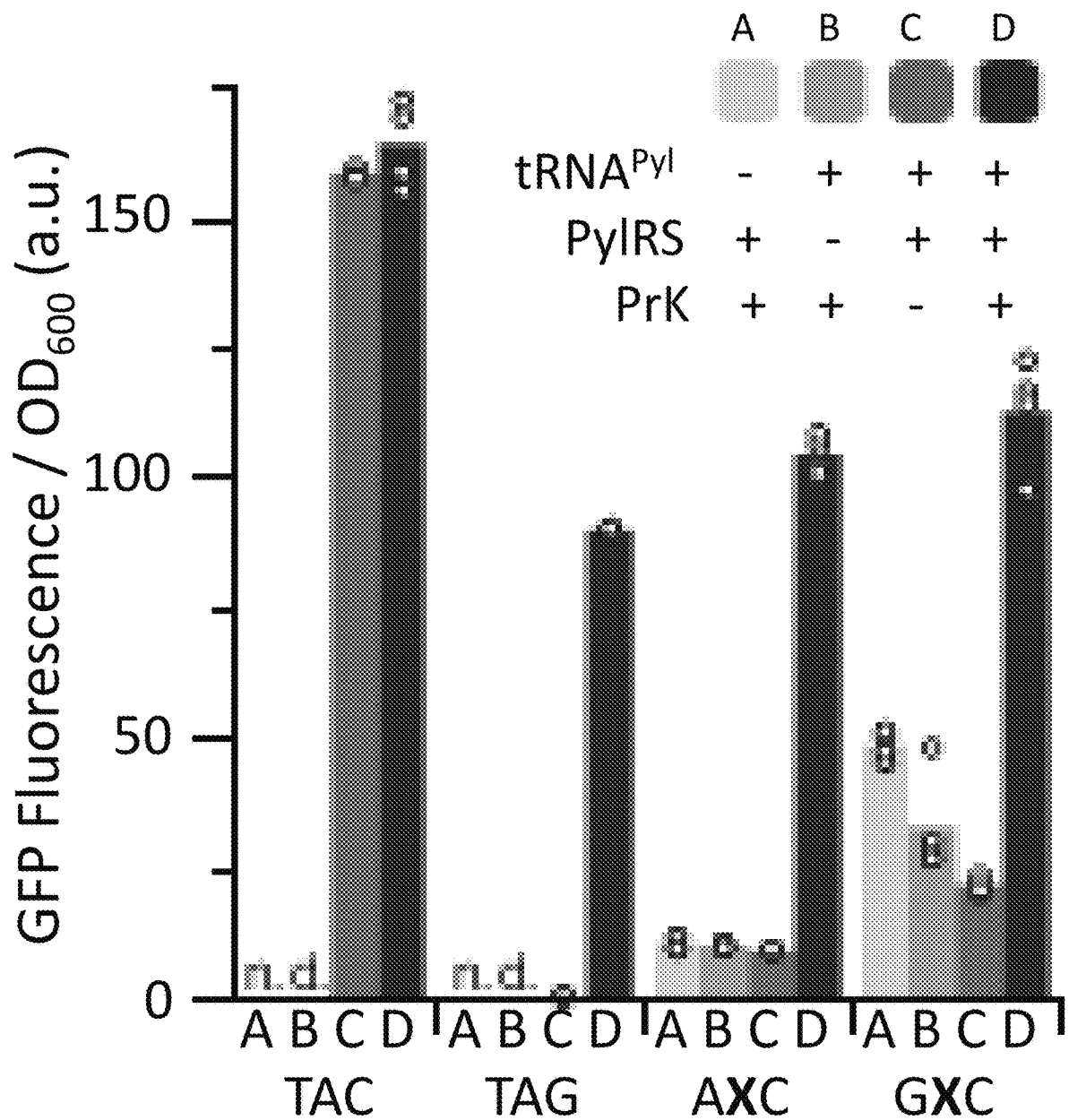
FIG. 2A illustrates a graph of fluorescence of cells expressing sfGFP with the indicated position 151-codon, in the presence (+) or absence (−) of a tRNA$^{Pyl}$ with a cognate anticodon, PylRS, or 20 mM PrK (N$^6$-[(2-propynyloxy)carbonyl]-L-lysine) in the media. Fluorescence was determined at the last time point shown in FIG. 2B. Asterisk denotes the absence of tRNA$^{Pyl}$ in cells expressing sfGFP (TAC)[151]. TAC, natural Tyr codon; TAG, amber stop codon; n.d., not determined. Data shown as mean with individual data points, each propagated from an individual colony.
Figure 2B:
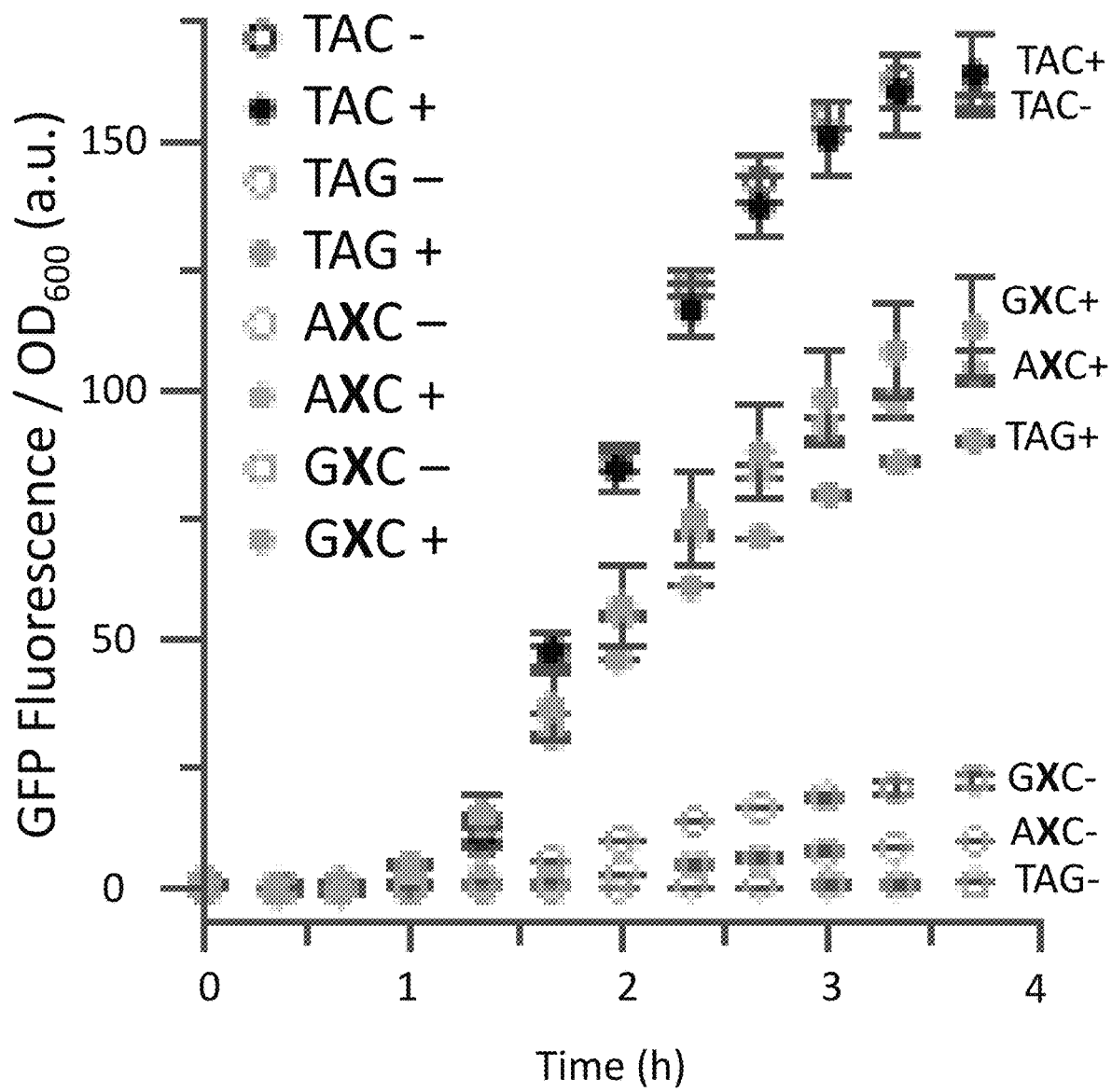
FIG. 2B illustrates a timecourse analysis of a subset of the data shown in FIG. 2A. Plus and minus signs denote the presence or absence, respectively, of 20 mM PrK in the media. t=0 corresponds to the addition of IPTG to induce expression of PylRS, T7 RNAP, and tRNA$^{Pyl}$; aTc was added at t=1 h to induce expression of sfGFP. Data shown as mean±s.d., n=4 cultures, each propagated from an individual colony.
Figure 6A:
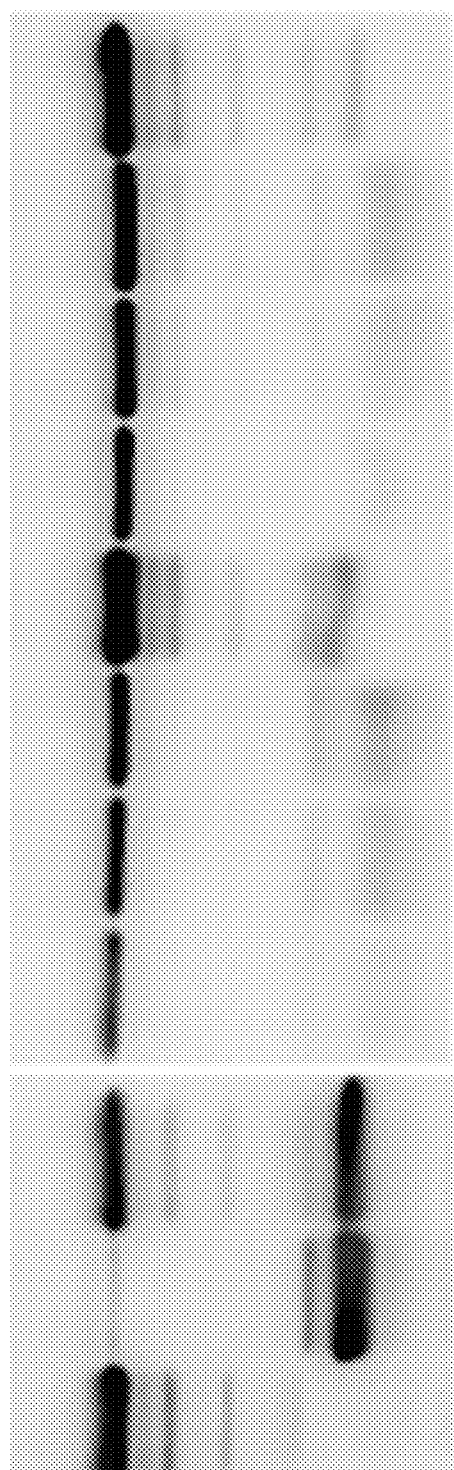
FIG. 6A illustrates Western blots and growth of cells decoding AXC and GXC codons with tRNA$^{Pyl}$. Western blot of lysates (normalized by OD$_{600}$) from cells expressing sfGFP with the indicated position 151-codon, in the presence (+) or absence (−) of a tRNA$^{Pyl}$ with a cognate anticodon, PylRS, or 20 mM PrK in the media. Blots were probed with an α-GFP antibody (N-terminal epitope). Cells were induced and collected at an equivalent time point as described in FIG. 2B.
Figure 6B:
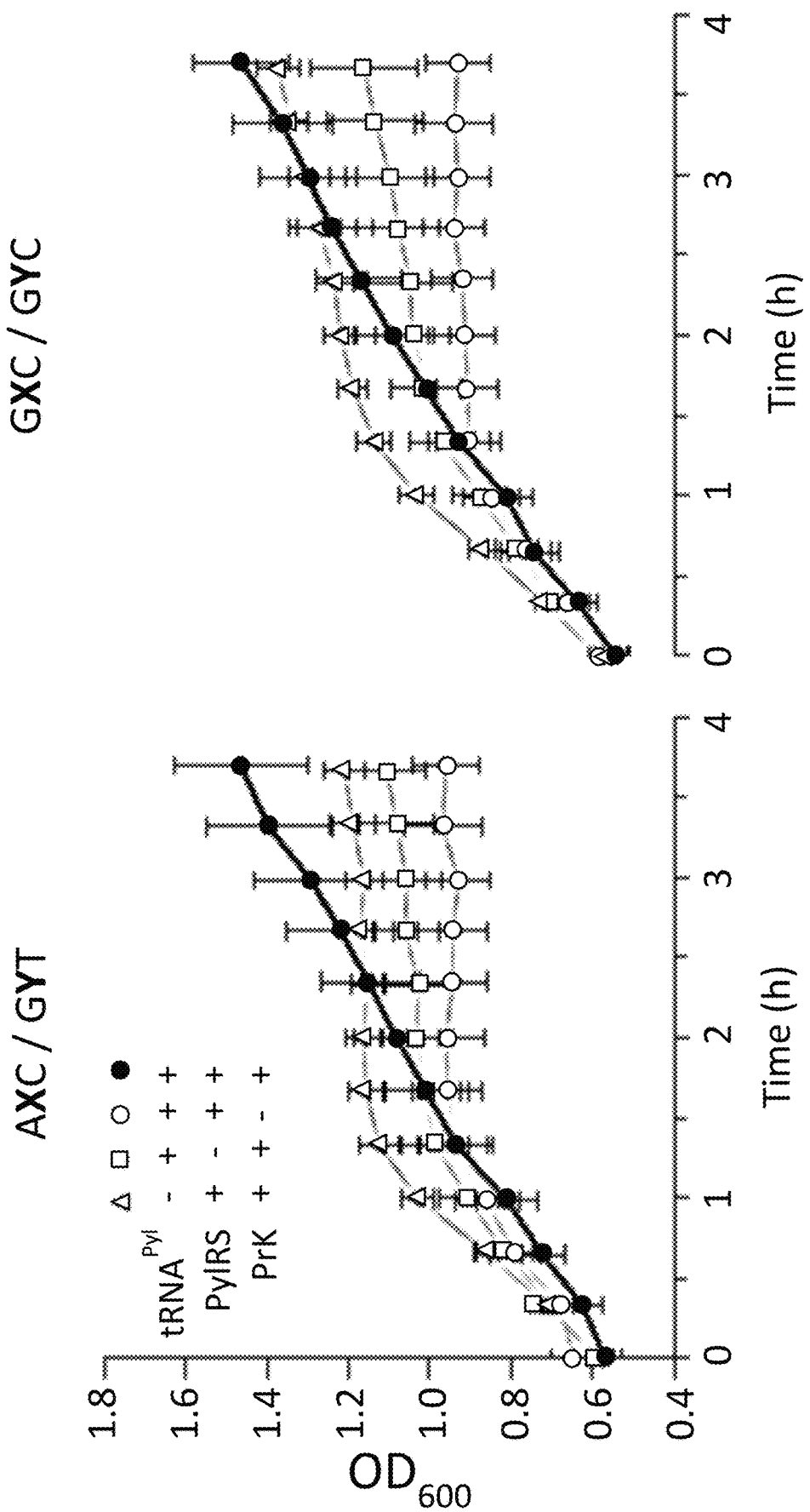
FIG. 6B illustrates growth of cultures analyzed in FIG. 6A. The fold change in OD$_{600}$ between induction of sfGFP (t=1 h) and the final time point is greatest when all components necessary for aminoacylating tRNA$^{Pyl}$ are present. Variations in the absolute value of OD$_{600}$ are due to small variations in cell density at the start of T7 RNAP (and if present tRNA$^{Pyl}$) induction (t=0). Data shown as mean±s.d., n=4 cultures, each propagated from an individual colony.

To demonstrate the encoding of ncAAs with UBPs, we constructed plasmids analogous to those used above, but with the tRNA$^{Ser}$ gene replaced with the *Methanosarcina mazei* tRNA$^{Pyl}$(GYT) gene. tRNA$^{Pyl}$ can be selectively charged by the *Methanosarcina barkeri* pyrrolysine aminoacyl tRNA synthetase (PylRS) with the ncAA N$^6$-[(2-propynyloxy)carbonyl]-L-lysine (PrK). In addition to the codon AXC, we also analyzed the codon GXC and the corresponding tRNA$^{Pyl}$(GYC). The SSO, carrying a separate plasmid encoding an IPTG-inducible PylRS, was transformed with the required plasmids and grown with or without added PrK. In control experiments with cells expressing either sfGFP (AXC)$^{151}$ or sfGFP(GXC)$^{151}$ in the absence of either PylRS, the cognate unnatural tRNA$^{Pyl}$, or PrK, we observed only low cellular fluorescence (FIG. 2A), truncation of sfGFP (FIGS. 6A and 6B), and a plateau in cell growth (FIG. 6B). In contrast, for either unnatural mRNA with its cognate unnatural tRNA, when PylRS was present and PrK was added, we observed high fluorescence (64% and 69% of sfGFP(TAC)$^{151}$ for AXC and GXC, respectively) (FIGS. 2A and 2B), robust production of full-length sfGFP (FIG. 6A), and normal growth (FIG. 6B).

Figure 2C:
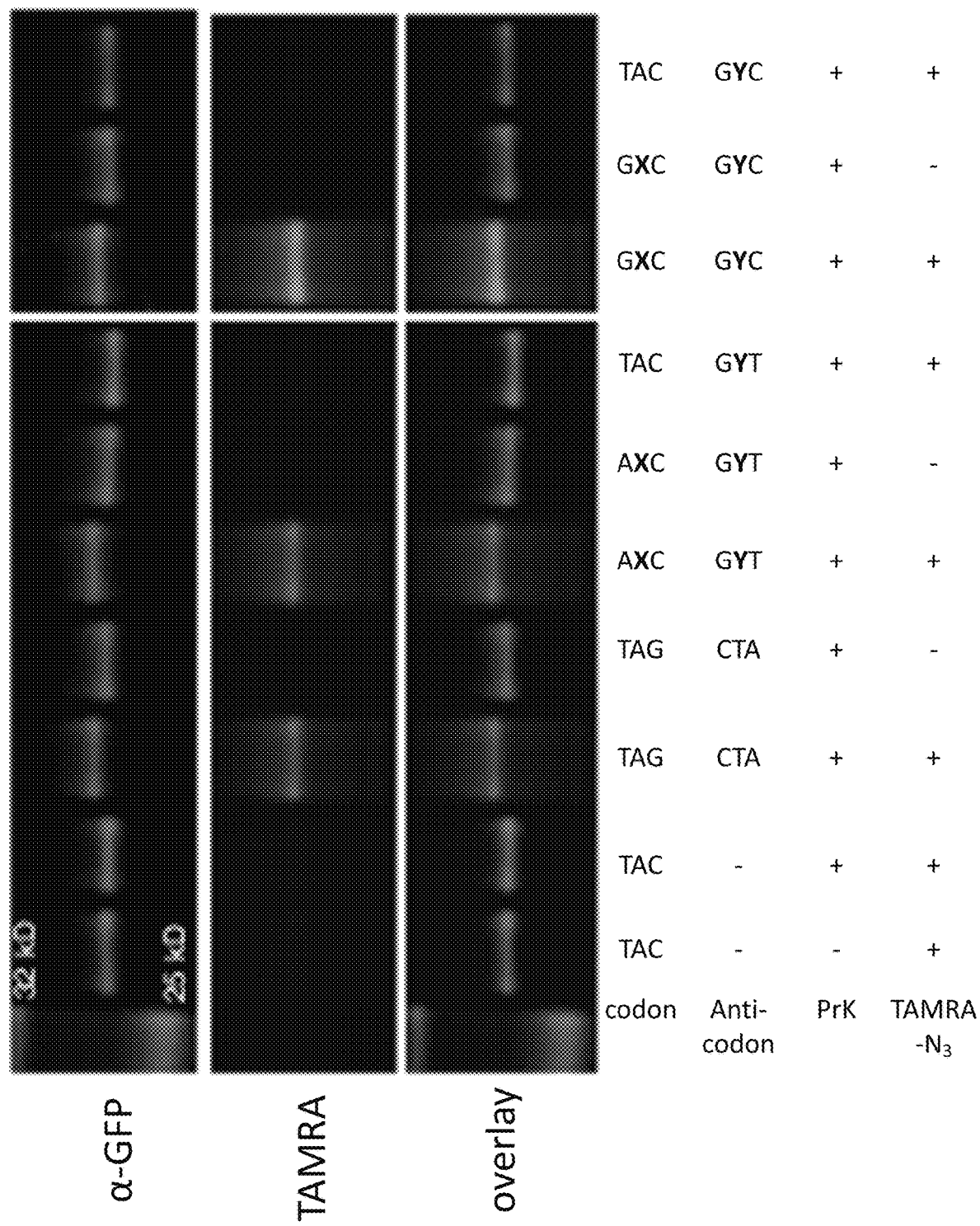
FIG. 2C illustrates Western blots of sfGFP purified from cells expressing sfGFP and tRNA$^{Pyl}$ with the indicated position-151 codon and anticodon, respectively, with or without click conjugation of TAMRA and/or addition of 20 mM PrK to the media. tRNA$^{Pyl}$ is absent (−) in cells expressing sfGFP(TAC)$^{151}$ sfGFP was purified from cultures collected at the last time point shown in FIG. 2B. Western blots were probed with an α-GFP antibody and imaged to detect both sfGFP and the conjugated TAMRA.
Figure 7A:
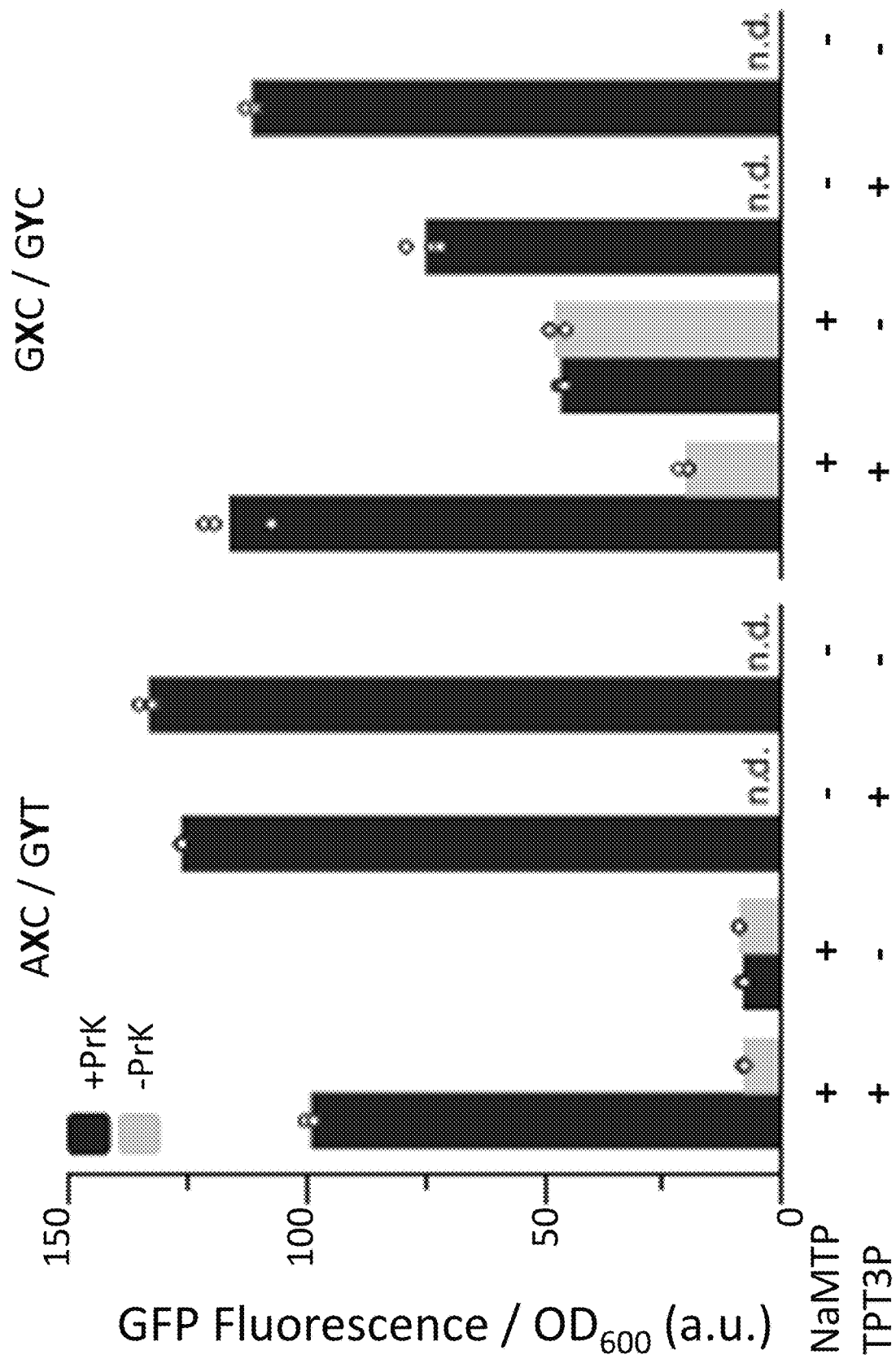
FIG. 7A illustrates decoding AXC and GXC codons with tRNA$^{Pyl}$ and cell growth as a function of added unnatural ribotriphosphates. Fluorescence of purified sfGFP (lower panel) from cells expressing sfGFP and tRNA$^{Pyl}$ with the position 151-codon/anticodon indicated, in the presence (+) or absence (−) of each unnatural ribotriphosphate in the media, and with or without 20 mM PrK. Cells were induced as described in FIG. 2B and fluorescence measurements were taken at the end of induction (~3.5 h), prior to collecting the cells and purifying the sfGFP protein for click conjugation of TAMRA and western blotting.
Figure 7B:
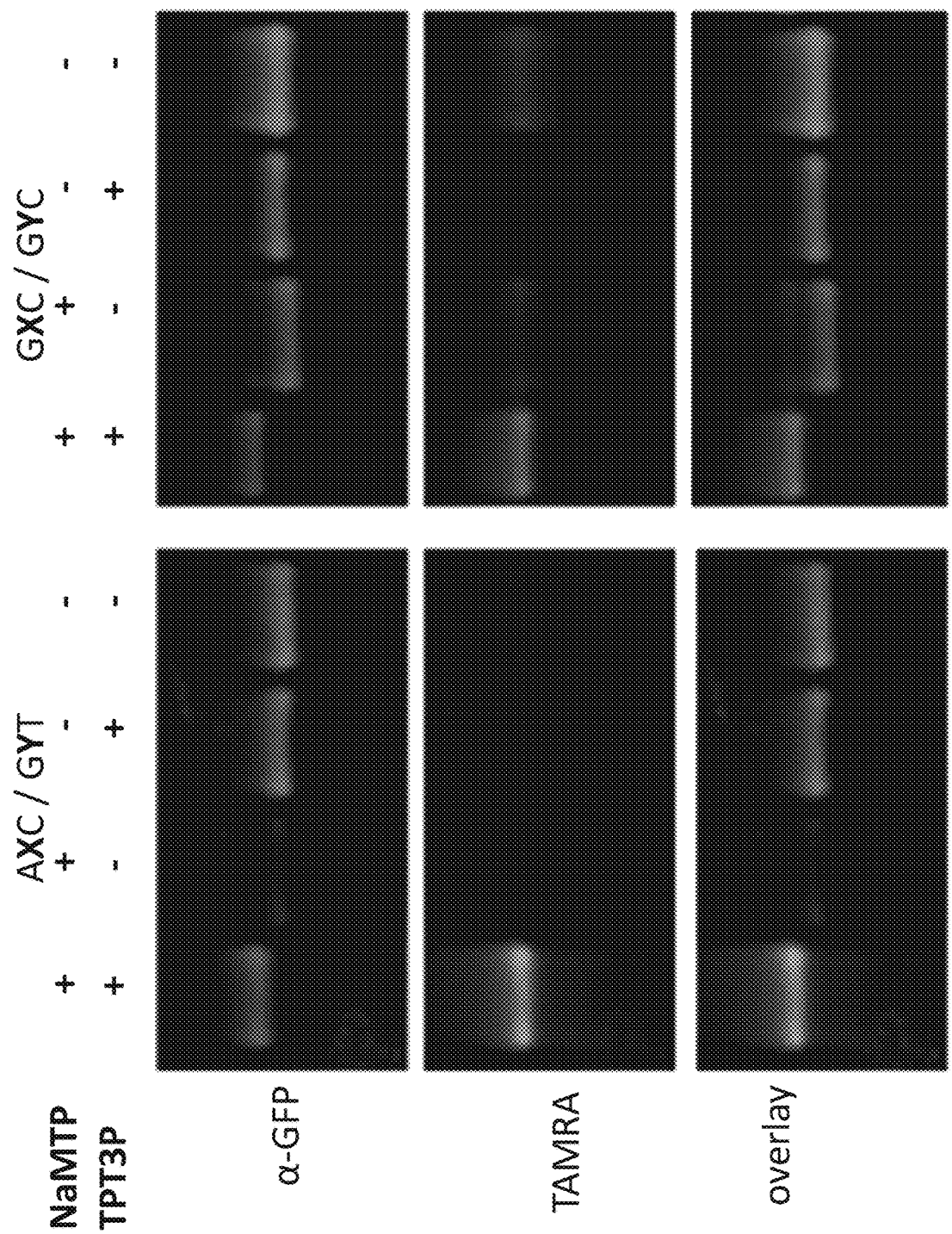
FIG. 7B illustrates a gel of decoding AXC and GXC codons with tRNA$^{Pyl}$ as a function of added unnatural ribotriphosphates. Western blots were probed with an α-GFP antibody and imaged to detect both sfGFP and the conjugated TAMRA; all lanes correspond to sfGFP purified from cells grown with added PrK. Data shown as mean with individual data points, n=3 cultures, each propagated from an individual colony; n.d., not determined.
Figure 7C:
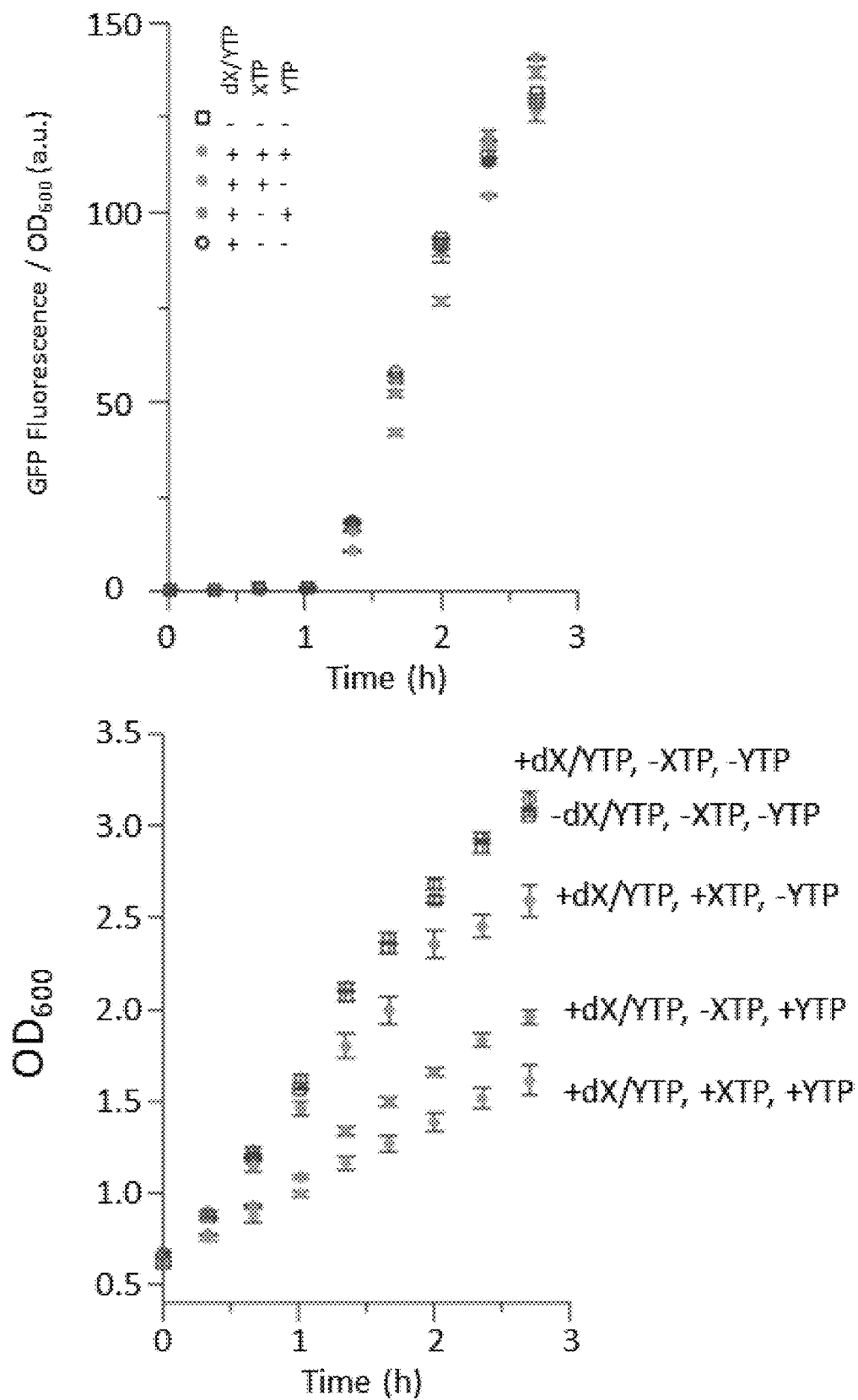
FIG. 7C, illustrates graphs of fluorescence and growth of cells expressing sfGFP(TAC)$^{151}$ in the presence (+) or absence (−) of both unnatural deoxyribotriphosphates and each unnatural ribotriphosphate. t=0 corresponds to the addition of IPTG to induce expression of T7 RNAP; aTc was added at t=1 h to induce expression of sfGFP. Data shown as mean±s.d., n=3 cultures, each propagated from an individual colony. At the concentrations used (see Methods), dNaMTP and dTPT3TP do not inhibit cell growth, whereas both unnatural ribotriphosphates, particularly TPT3TP, show some inhibition of growth.
Figure 7D:
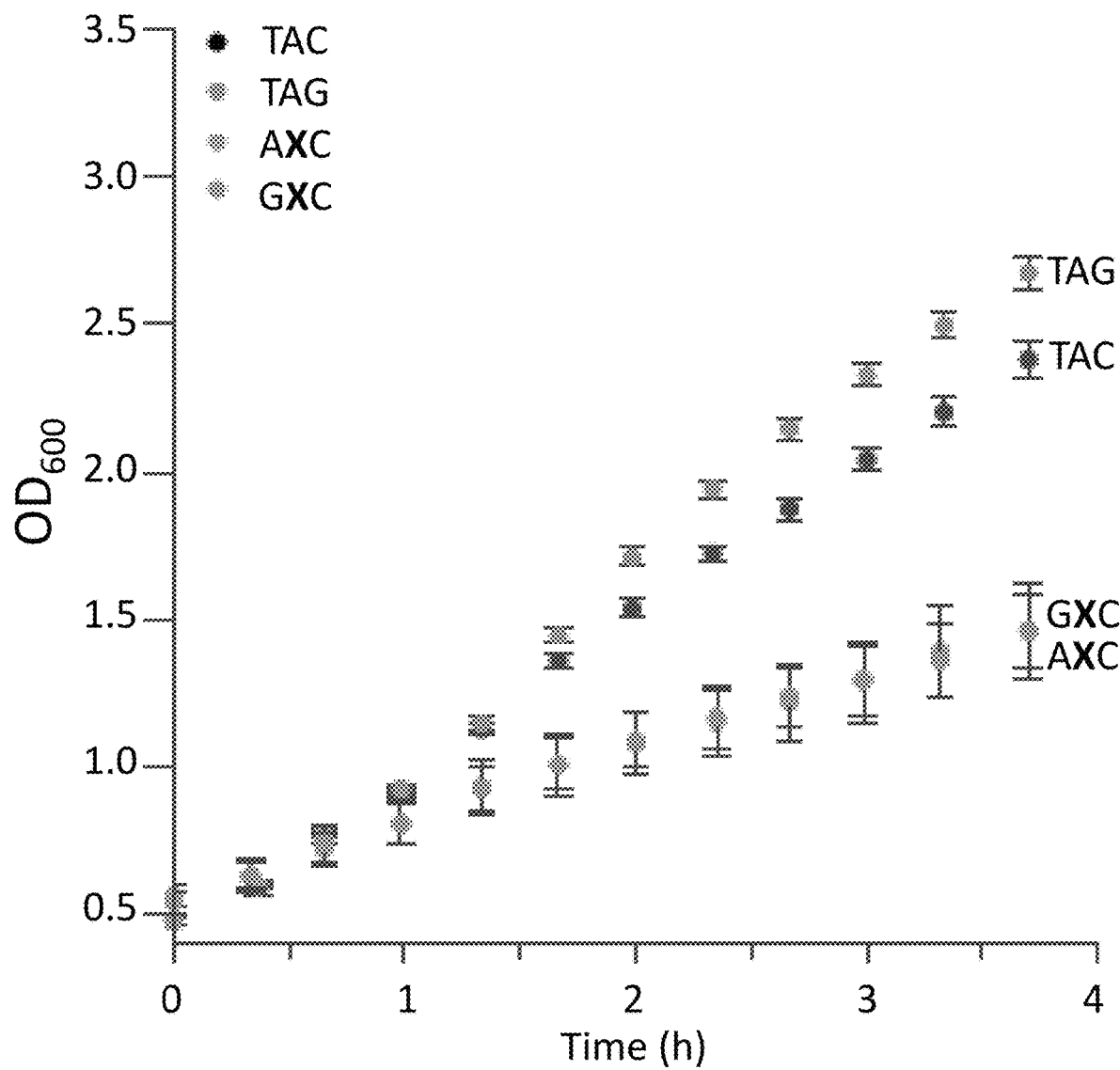
FIG. 7D illustrates a graph of cell growth corresponding to the cultures with added PrK (20 mM) whose fluorescence is shown in FIG. 2B. Cells expressing sfGFP with natural codons were grown without any unnatural triphosphates, whereas cells expressing sfGFP with unnatural codons were grown with both unnatural deoxy- and ribotriphosphates. Data shown as mean±s.d., n=4 cultures, each propagated from an individual colony.
Figure 8A:
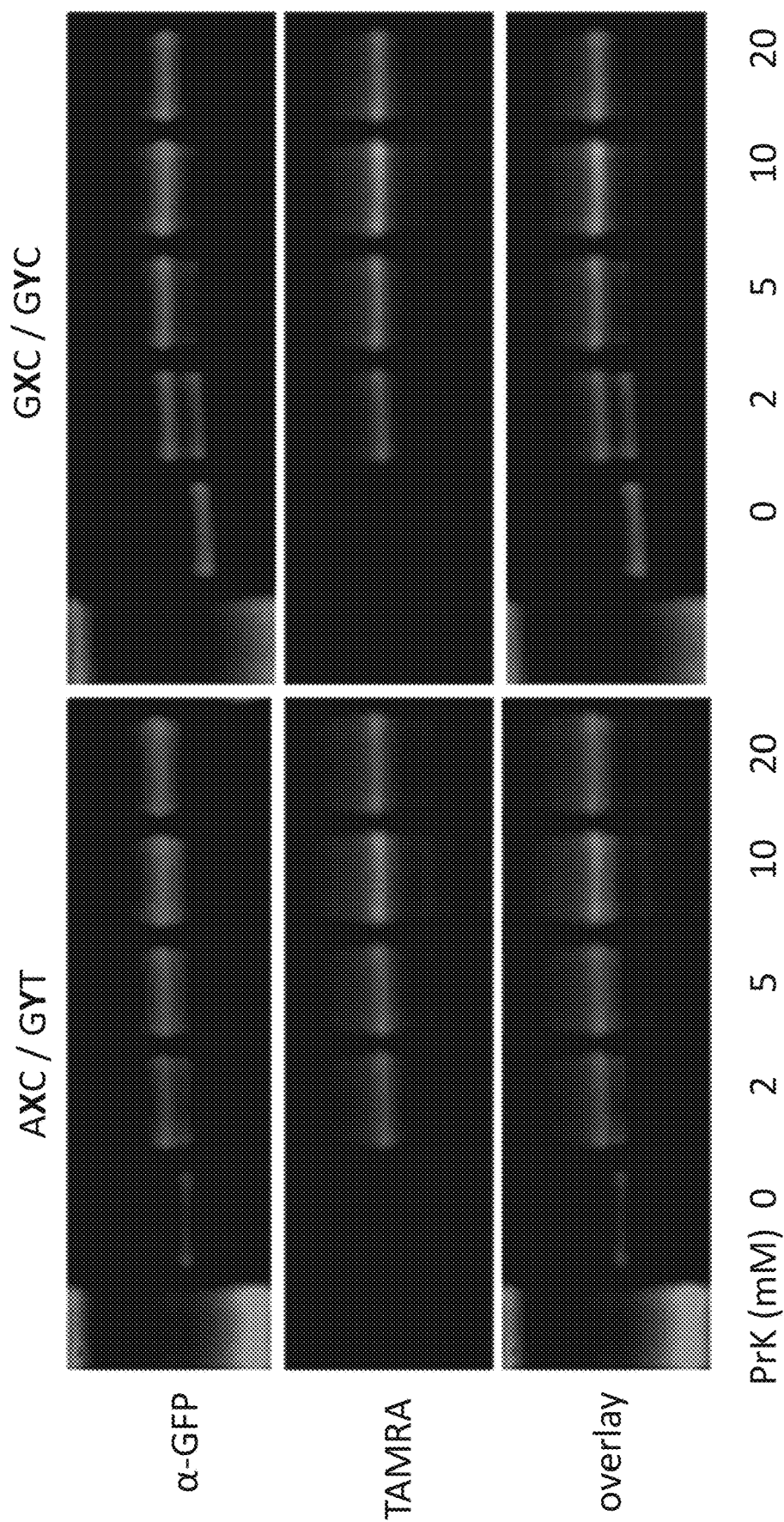
FIG. 8A illustrates a gel of decoding AXC and GXC codons with tRNA$^{Pyl}$ as a function of PrK concentration in the media. Western blots of sfGFP purified from cells expressing sfGFP and tRNA$^{Pyl}$ with the indicated position-151 codon/anticodon, with click conjugation of TAMRA and the addition of PrK to the media at the indicated concentrations. sfGFP was induced and purified from cells collected as described in FIG. 2B. Western blots were probed with an α-GFP antibody and imaged to detect both sfGFP and the conjugated TAMRA.
Figure 8B:
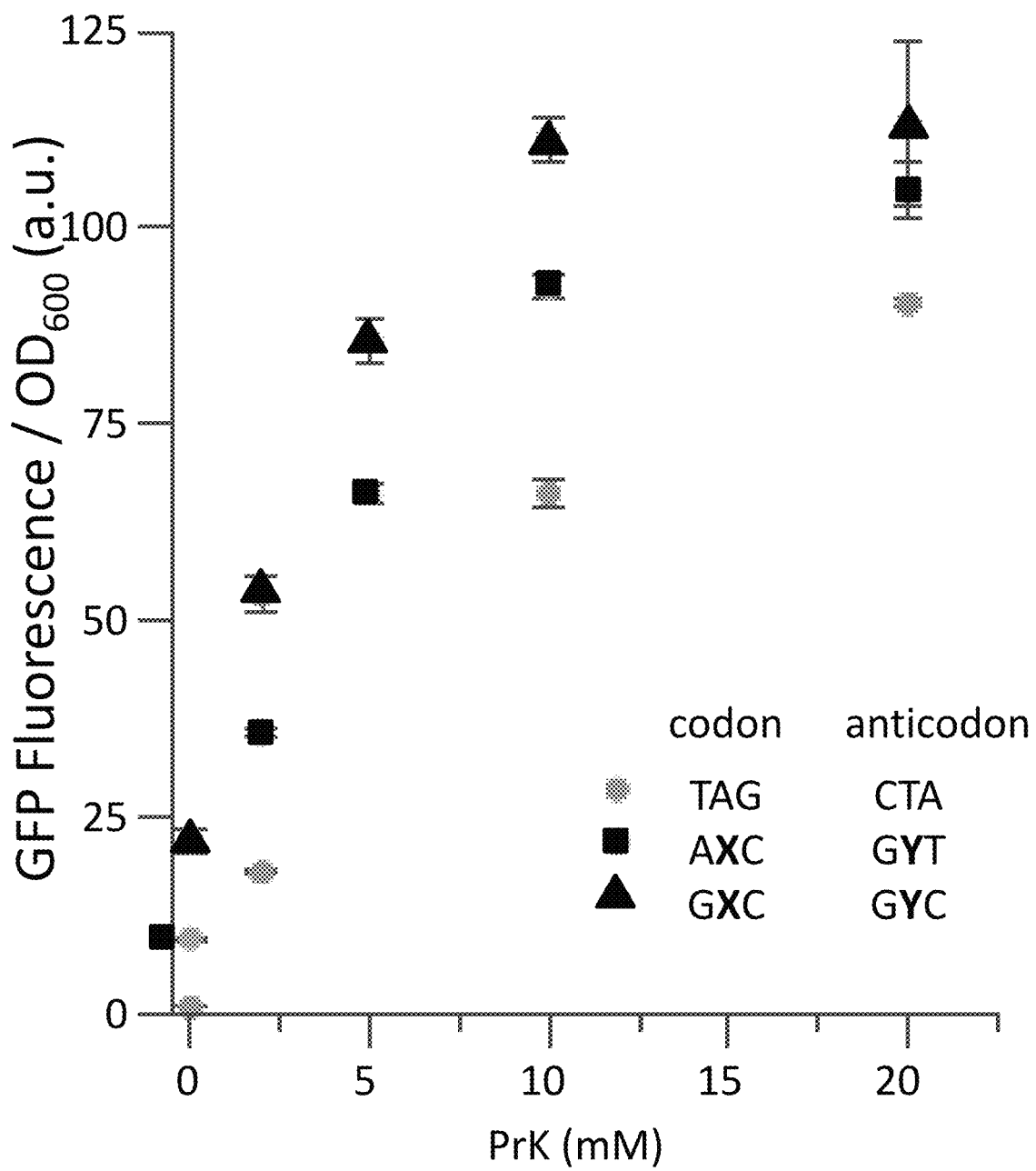
FIG. 8B illustrates a graph of decoding AXC and GXC codons with tRNA$^{Pyl}$ as a function of PrK concentration in the media. Fluorescence of cells (measured at the last time point shown in c) expressing sfGFP and tRNA$^{Pyl}$ with the indicated position-151 codon and anticodon, respectively, as a function of PrK concentration in the media. Fluorescence values for 0 and 20 mM PrK are the same as the (−) and (+) PrK values, respectively, shown in FIG. 2B. Data shown as mean±s.d., n=4 cultures, each propagated from an individual colony.
Figure 8C:
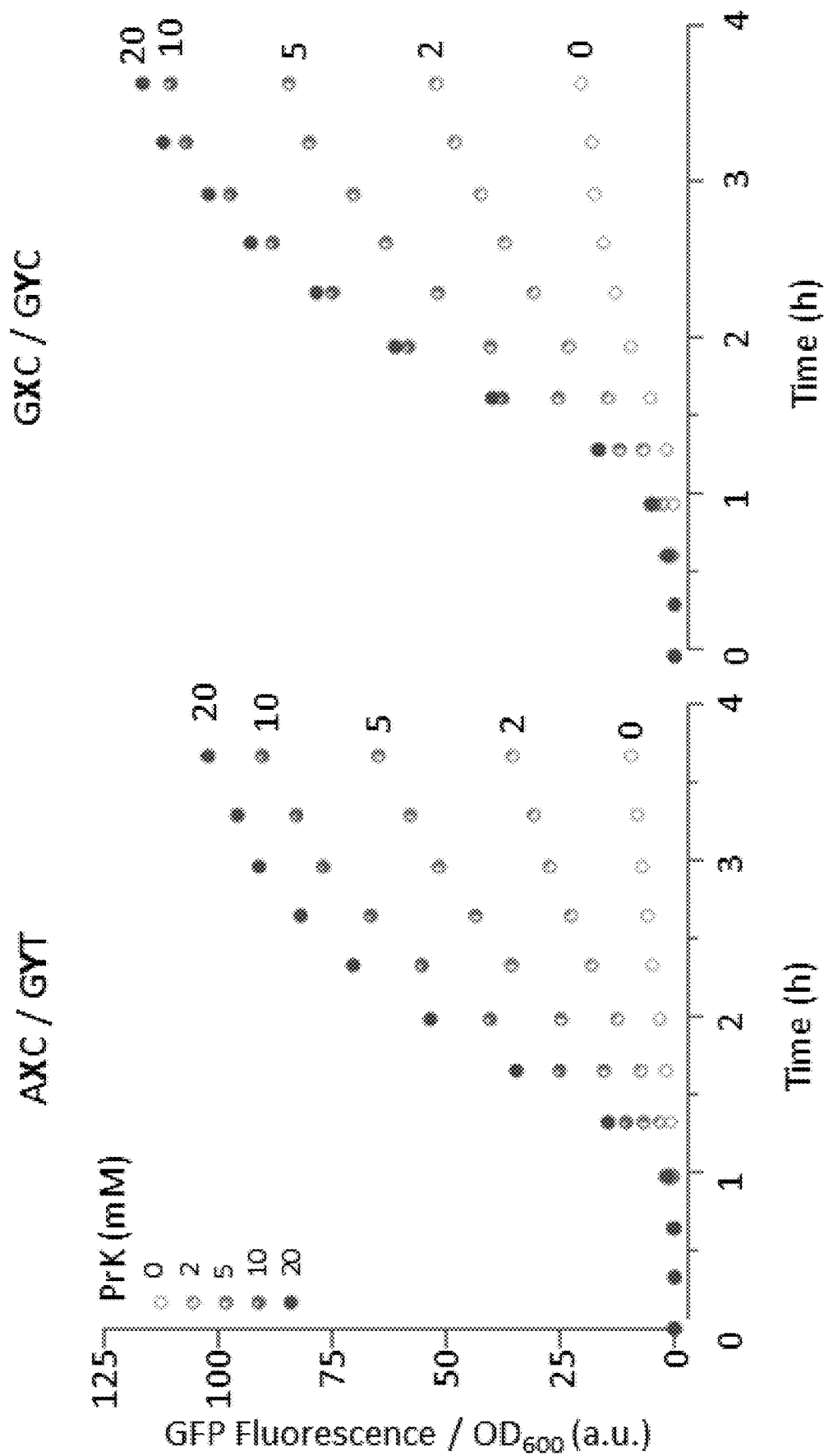
FIG. 8C illustrates a timecourse analysis of fluorescence. For clarity, only one representative culture is shown for each codon/anticodon pair and PrK concentration. Without being bound by theory, we attribute the low level of sfGFP produced in the absence of PrK to decoding by endogenous tRNAs and loss of UBP retention in sfGFP (Table 5). However, the relative amount of sfGFP that contains PrK (FIG. 8A) and absolute amount of sfGFP expressed (FIG. 8B and FIG. 8C) increased in a dose-dependent manner with increasing PrK in the media, ultimately resulting in nearly full incorporation of PrK, suggesting that endogenous readthrough of the AXC and GXC codons can be efficiently suppressed with sufficient concentrations of charged PrK-tRNA$^{Pyl}$(GYT) or PrK-tRNA$^{Pyl}$(GYC).
Figure 8D:
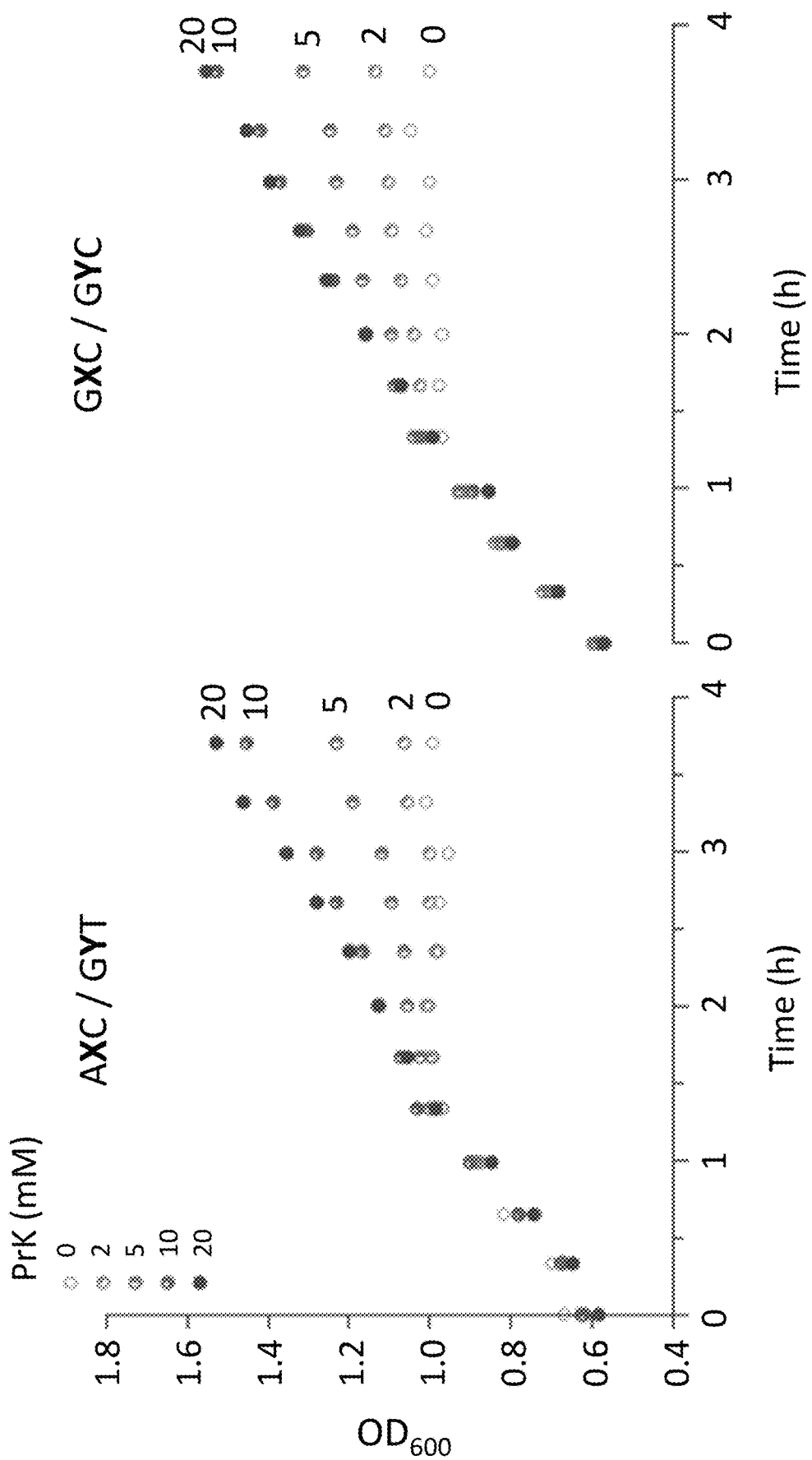
FIG. 8D illustrates a timecourse analysis of cell growth at various concentrations of PrK for the experiment shown in FIG. 8C.

To verify the incorporation of PrK, sfGFP was affinity purified from cell lysates using a C-terminal Strep-tag II and subjected to copper-catalyzed click chemistry to attach a carboxytetramethylrhodamine (TAMRA) dye (TAMRA-PEG$_4$-N$_3$), which was found to shift the electrophoretic mobility of sfGFP during SDS-PAGE, thus allowing us to assess the fidelity of PrK incorporation by western blotting (FIG. 2C). We observed strong TAMRA signal and that virtually all of the sfGFP was shifted when purified from cells expressing sfGFP(AXC)$^{151}$ and tRNA$^{Pyl}$(GYT) or sfGFP(GXC)$^{151}$ and tRNA$^{Pyl}$(GYC), and which had been cultured in media supplemented with PrK (FIG. 2C). In contrast, little to no TAMRA signal or shifted sfGFP was observed when NaMTP, TPT3TP, or both were absent (FIGS. 7A and 7B). Finally, no TAMRA signal or shifted sfGFP was observed in protein purified from cells expressing sfGFP(TAC)$^{151}$ with either unnatural tRNA (FIG. 2C). This data demonstrates that PrK is specifically incorporated into sfGFP via decoding of the unnatural codons by tRNAs with an unnatural anticodon.

Figure 2D:
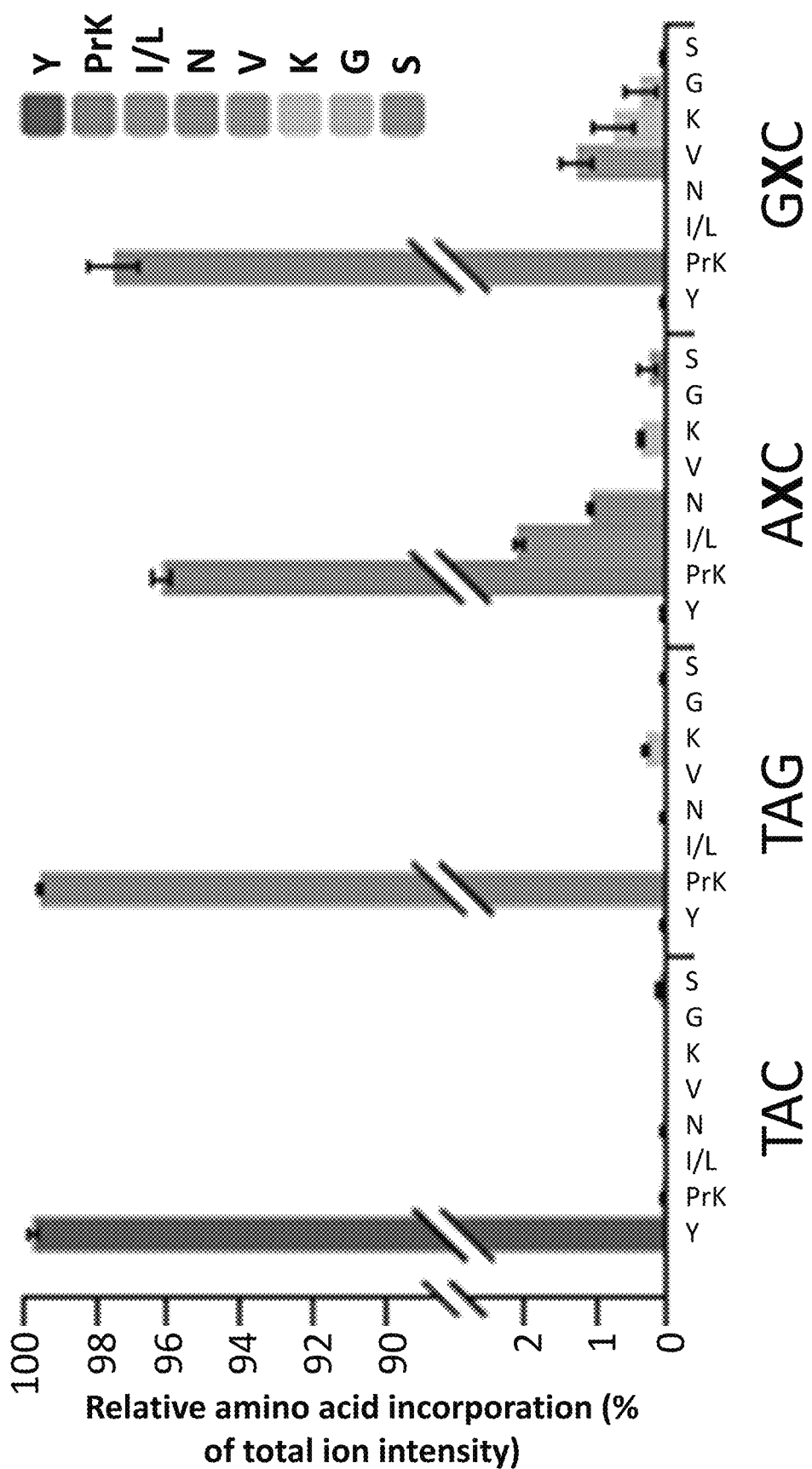
FIG. 2D illustrates a graph of the relative abundance of amino acids (indicated by their single letter codes in the figure legend) at position 151 of sfGFP purified from cells (collected at the last time point shown in FIG. 2B) expressing sfGFP(TAC)$^{151}$ or sfGFP and tRNA$^{Pyl}$ with the indicated position-151 codon and a cognate anticodon, respectively, as determined by LC-MS/MS and precursor ion intensity based quantitation (amino acids detected at <0.1% (on average, for all codons) are not shown; see Methods for details and Table 4 for a complete list of amino acids detected). Data shown as mean with individual data points, n=4 purified sfGFP samples, each from a culture propagated from an individual colony.

With optimal PrK concentrations (FIGS. 8A-8D), we purified 54±4 and 55±6 μg/mL of sfGFP (s.d., n=4, ~40% of the sfGFP(TAC)$^{151}$ control (Table 6) for the AXC and GXC codons, respectively. Moreover, based on mass spectrometry analysis, the purity of sfGFP with PrK was 96.2±0.3% (95% CI, n=4) for the AXC codon and 97.5±0.7% (95% CI, n=4) for the GXC codon (FIG. 2D). Although the yield of sfGFP protein purified was slightly lower than with amber suppression (87±6 μg/mL, s.d., n=4 (Table 6)), due to a moderate reduction in growth with addition of the unnatural ribotriphosphates (FIGS. 7C and 7D), decoding of both unnatural codons resulted in higher fluorescence than amber suppression when normalized to cell density (FIGS. 2A and 2B), implying that decoding with the unnatural codons is more efficient than amber suppression.

Figure 3A:
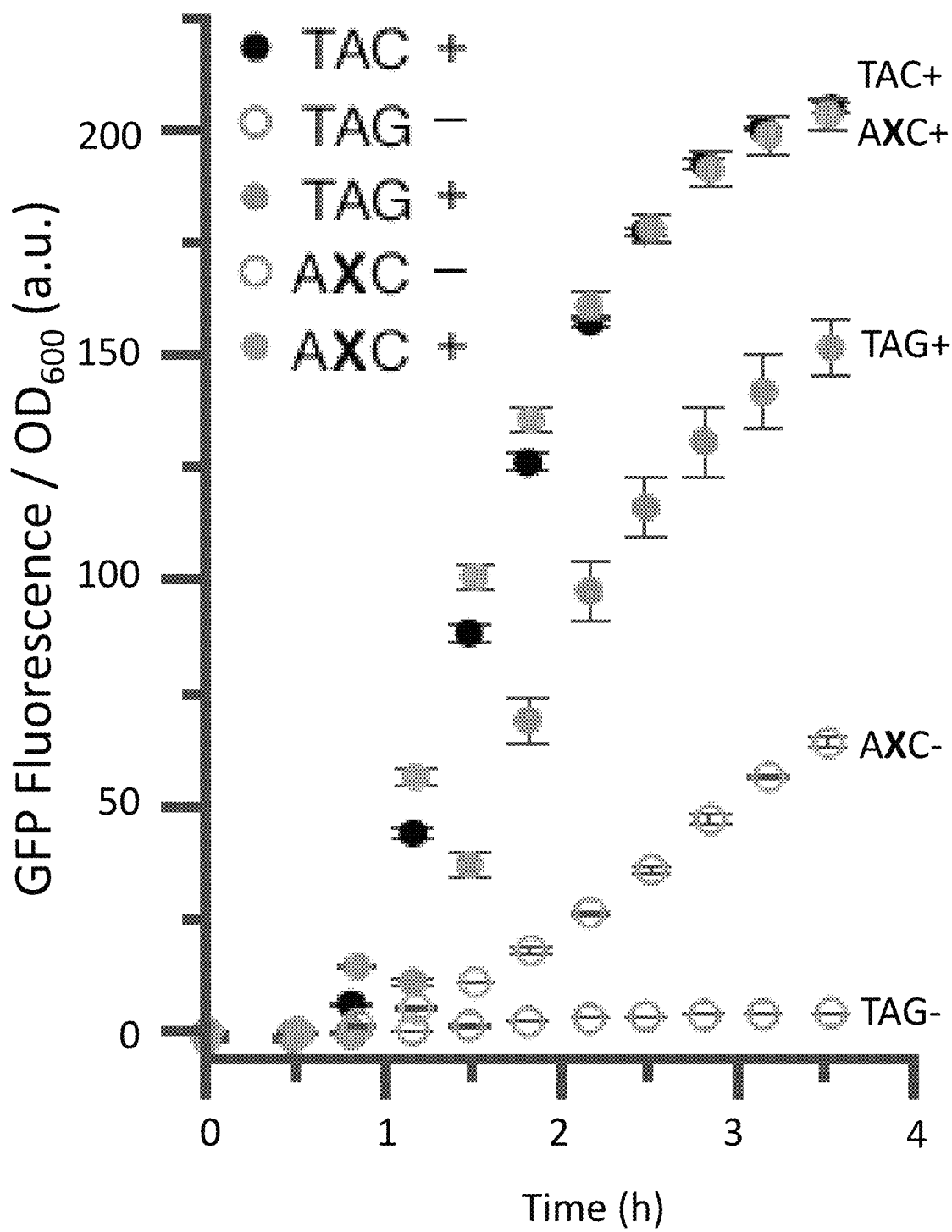
FIG. 3A illustrates a graph of fluorescence of cells expressing sfGFP(TAC)$^{151}$ or sfGFP and tRNA$^{pAzF}$ with the indicated position-151 codon and a cognate anticodon, respectively, in the presence (+) or absence (−) of 5 mMpAzF in the media. t=0 corresponds to the addition of IPTG to induce expression of pAzFRS, T7 RNAP, and tRNA$^{pAzF}$; aTc was added at t=0.5 h to induce expression of sfGFP. TAC, natural Tyr codon; TAG, amber stop codon. Data shown as mean±s.d., n=4 cultures, each propagated from an individual colony. The fluorescence observed with sfGFP(AXC)$^{151}$ in the absence of pAzF is attributed to charging of tRNA$^{pAzF}$(GYT) with a natural amino acid (likely Tyr).
Figure 3B:
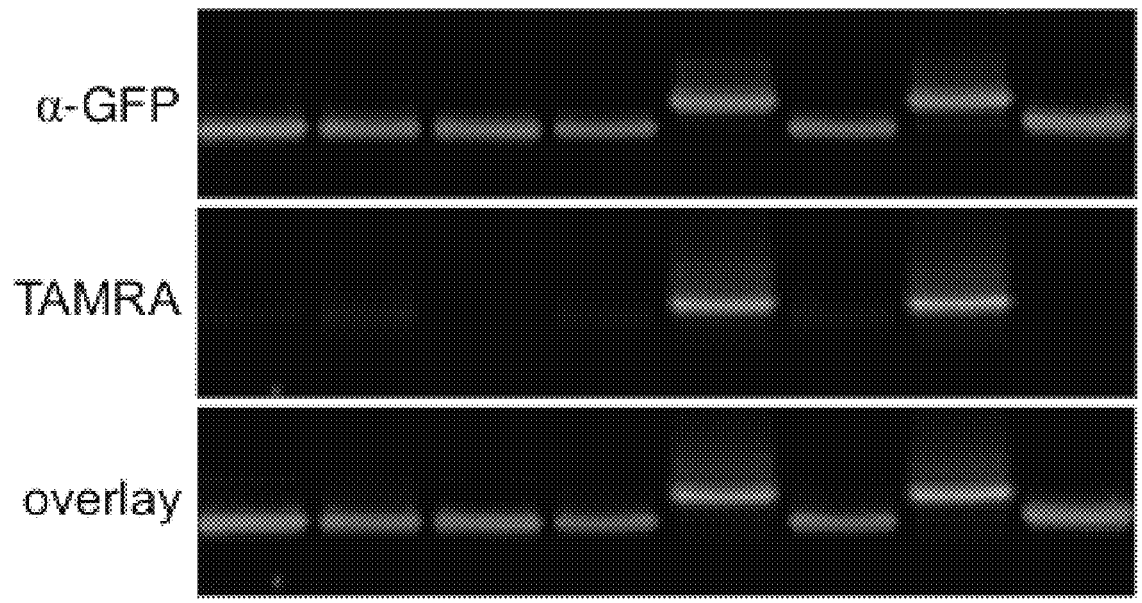
FIG. 3B illustrates a Western blot of sfGFP purified from cells expressing sfGFP and tRNA$^{pAzF}$ with the indicated position-151 codon and anticodon, respectively, with or without click conjugation of TAMRA and/or addition of 5 mMpAzF to the media. Where indicated, the minus sign denotes the absence of tRNA$^{pAzF}$ in cells expressing sfGFP (TAC)$^{151}$ sfGFP was purified from cultures collected at the last time point shown in FIG. 3A. Western blots were probed with an α-GFP antibody and imaged to detect both sfGFP and the conjugated TAMRA.
Figure 9:
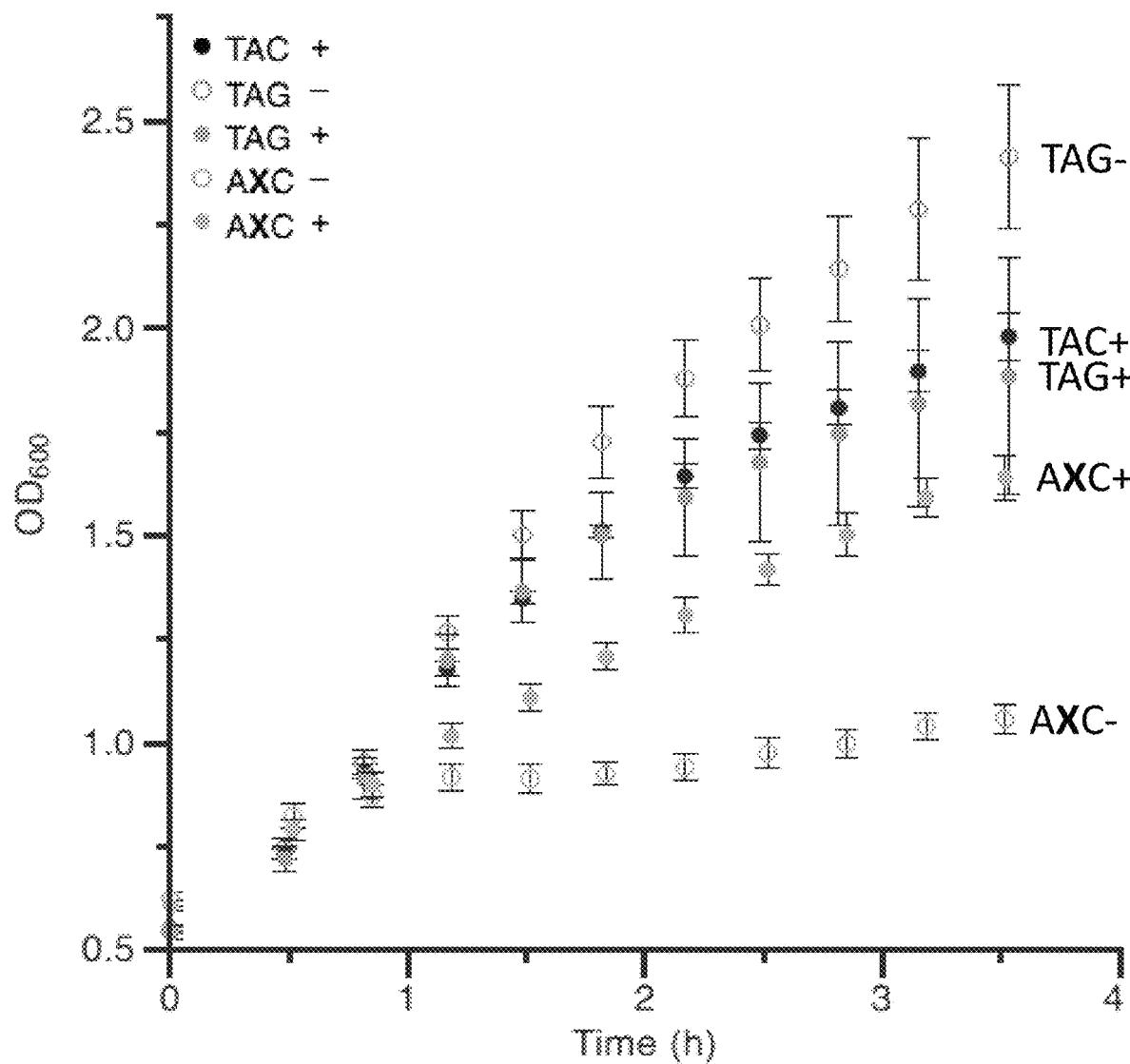
FIG. 9 illustrates cell growth of the cultures whose fluorescence is shown in FIG. 3A. Data shown as mean±s.d., n=4 cultures, each propagated from an individual colony Table 4|Relative abundance of amino acids at position 151 in sfGFP for experiments described in FIG. 1F and FIG. 2D. sfGFP purified from cells expressing sfGFP with or without tRNAs with the indicated position-151 codon and anticodon, respectively, were analyzed by LC-MS/MS. The extracted MS1 ion intensities for the reporter peptides LEYNFNSHNVX$^{151}$ITADK (X=PrK or any identified natural amino acid except K or R) and LEYNFNSHNVX$^{151}$ (if X=K or R) are expressed as a percentage of the sum of ion intensities for all observable reporter peptides. The table of values corresponds to the mean relative abundances and 95% CIs of all amino acids detected at position 151 of sfGFP, n=4 purified sfGFP samples, each from a culture propagated from an individual colony. Values<0.1% (on average, for the codons indicated in the respective figures) are excluded from the data presented in FIG. 1F and FIG. 2D.

To explore the encoding of other ncAAs with UBPs, we examined the encoding of p-azido-phenylalanine (pAzF) with the AXC codon and an evolved *Methanococcus jannaschii* TyrRS/tRNA$^{Tyr}$ pair (pAzFRS/tRNA$^{pAzF}$). With induction of the synthetase and the addition of pAzF to the growth media, we observed robust fluorescence equivalent to that of cells expressing natural sfGFP(TAC)$^{151}$ and normal growth with sfGFP(AXC)$^{151}$ and tRNA$^{pAzF}$(GYT) (FIG. 3A, FIG. 9). Full-length sfGFP was purified (86±6 μg/mL, s.d., n=4; 68% of the sfGFP(TAC)$^{151}$ control, Table 6) and subjected to copper-free click chemistry using a dibenzocyclooctyl (DBCO) group to attach TAMRA (TAMRA-PEG$_4$-DBCO). We observed robust TAMRA conjugation to sfGFP isolated from cells expressing sfGFP (AXC)$^{151}$ and tRNA$^{pAzF}$(GYT) and cultured in the presence of pAzF (FIG. 3B). Although we were unable to accurately assess the fidelity of pAzF incorporation due to decomposition of the azido moiety, ~93% of the sfGFP protein was shifted, which compares favorably to the ~95% shifted sfGFP produced via amber suppression (FIG. 3B).

TABLE 6

| Sample | aaRS | Yield (μg/mL) | Relative to control (%) | Total Fluor (a.u.) | Relative to control (%) |
|---|---|---|---|---|---|
| sfGFP(AGT)$^{151}$ | SerRS | 100 ± 8 | 100 | 269 | 100 |
| sfGFP(AXC)$^{151}$/tRNA$^{Ser}$(GYT) | (endogenous) | 97 ± 9 | 96 | 259 | 96 |
| sfGFP(TAC)$^{151}$ | PylRS | 135 ± 17 | 100 | 400 | 100 |
| sfGFP(TAG)$^{151}$/tRNA$^{Pyl}$(CTA) | | 87 ± 6 | 65 | 242 | 60 |
| sfGFP(AXC)$^{151}$/tRNA$^{Pyl}$(GYT) | | 54 ± 4 | 40 | 153 | 38 |
| sfGFP(GXC)$^{151}$/tRNA$^{Pyl}$(GYC) | | 55 ± 6 | 41 | 166 | 41 |
| sfGFP(TAC)$^{151}$ | pAzFRS | 127 ± 15 | 100 | 405 | 100 |
| sfGFP(TAG)$^{151}$/tRNA$^{pAzF}$(CTA) | | 75 ± 9 | 59 | 287 | 71 |
| sfGFP(AXC)$^{151}$/tRNA$^{pAzF}$(GYT) | | 86 ± 6 | 68 | 333 | 82 |

Since at least the last common ancestor of all life on earth, proteins have been produced via the decoding of codons written solely with the four-nucleotide genetic alphabet. We have now demonstrated the decoding of two new codons, written with an expanded genetic alphabet, and used the new codons to site-specifically incorporate ncAAs into proteins. We find that for every step of information storage and retrieval, hydrogen bonds, so obviously central to the natural base pairs, may at least in part be replaced with complementary packing and hydrophobic forces. Despite their novel mechanism of decoding, the unnatural codons can be decoded as efficiently as their fully natural counterparts. While we have only examined the decoding of two unnatural codons, the UBP is unlikely to be limited to these, and when combined with a recently reported Cas9 editing system that reinforces UBP retention, it will likely make available more codons than can ever be used. Thus, the reported SSO may be just the first of a new form of semi-synthetic life that is able to access a broad range of forms and functions not available to natural organisms.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A cell comprising:
   a. a nucleoside triphosphate transporter from *Phaeodactylum tricornutum*;
   b. a tRNA from *Methanosarcina mazei* or *Methanococcus jannaschii* comprising an anticodon, wherein the anticodon comprises a sequence selected from GGY, GYG, YGG, GAY, GYA, YGA, GCY, GYC, YGC, GUY, GYU, YGU, CAY, CYA, YCA, CGY, CYG, YCG, CUY, CYU, YCU, CCY, CYC, YCC, AAY, AYA, YAA, AGY, AYG, YAG, ACY, AYC, YAC, AUY, AYU, YAU, UUY, UYU, YUU, UAY, UYA, YUA, UGY, UYG, YUG, UCY, UYC, YUC, GYY, YGY, YYG, CYY, YCY, YYC, AYY, YAY, YYA, UYY, YUY, YYU, YYY, GGX, GXG, XGG, GAX, GXA, XGA, GCX, GXC, XGC, GUX, GXU, XGU, CAX, CXA, XCA, CGX, CXG, XCG, CUX, CXU, XCU, CCX, CXC, XCC, AAX, AXA, XAA, AGX, AXG, XAG, ACX, AXC, XAC, AUX, AXU, XAU, UUX, UXU, XUU, UAX, UXA, XUA, UGX, UXG, XUG, UCX, UXC, XUC, GXX, XGX, XXG, CXX, XCX, XXC, AXX, XAX, XXA, UXX, XUX, XXU, or XXX, and wherein each of Y and X are an unnatural nucleotide comprising an unnatural nucleobase selected from

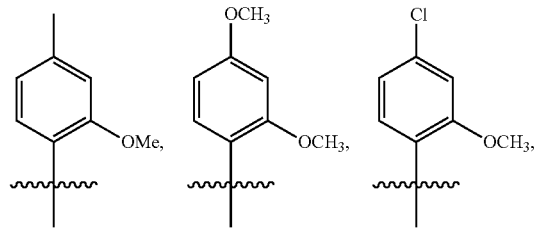

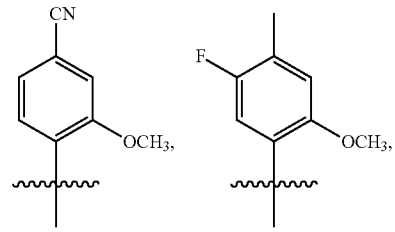

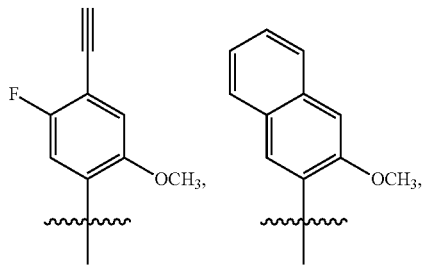

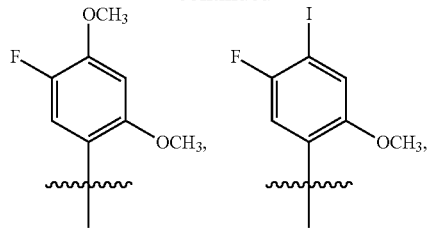

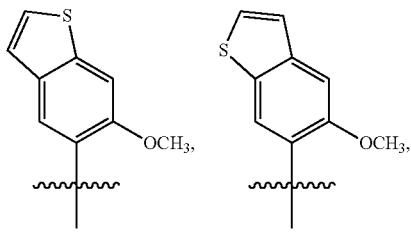

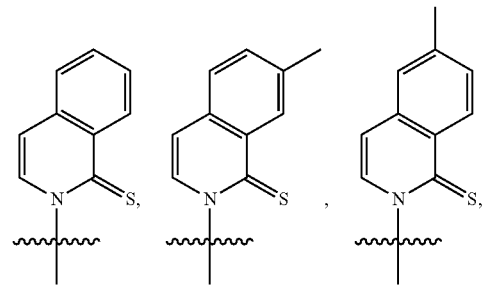

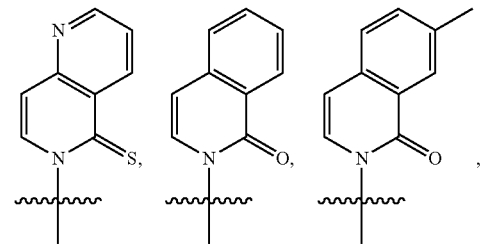

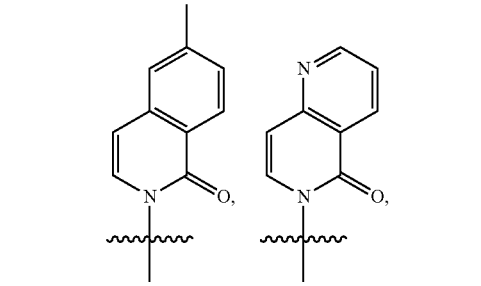

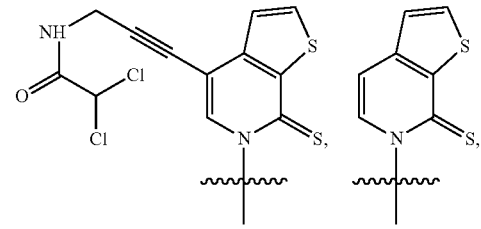

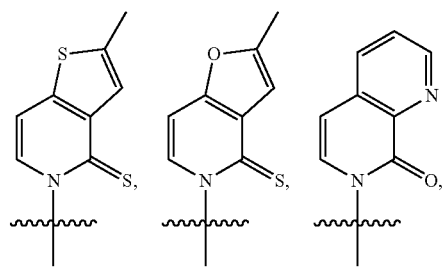

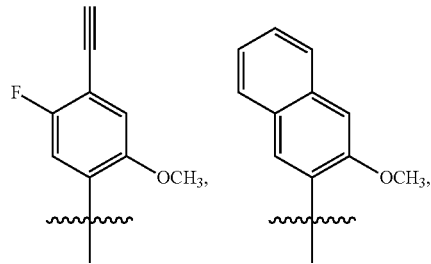

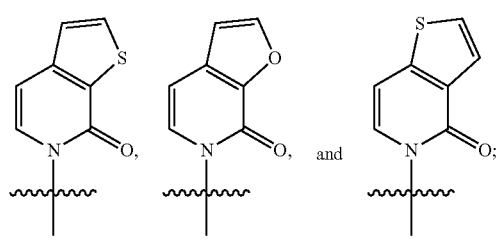

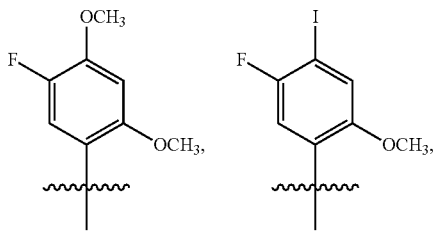

c. an aminoacyl tRNA synthetase from *Methanosarcina* or *Methanococcus jannaschii*; and d. an mRNA comprising a codon, wherein the codon comprises a sequence selected from GGY, GYG, YGG, GAY, GYA, YGA, GCY, GYC, YGC, GUY, GYU, YGU, CAY, CYA, YCA, CGY, CYG, YCG, CUY, CYU, YCU, CCY, CYC, YCC, AAY, AYA, YAA, AGY, AYG, YAG, ACY, AYC, YAC, AUY, AYU, YAU, UUY, UYU, YUU, UAY, UYA, YUA, UGY, UYG, YUG, UCY, UYC, YUC, GYY, YGY, YYG, CYY, YCY, YYC, AYY, YAY, YYA, UYY, YUY, YYU, YYY, GGX, GXG, XGG, GAX, GXA, XGA, GCX, GXC, XGC, GUX, GXU, XGU, CAX, CXA, XCA, CGX, CXG, XCG, CUX, CXU, XCU, CCX, CXC, XCC, AAX, AXA, XAA, AGX, AXG, XAG, ACX, AXC, XAC, AUX, AXU, XAU, UUX, UXU, XUU, UAX, UXA, XUA, UGX, UXG, XUG, UCX, UXC, XUC, GXX, XGX, XXG, CXX, XCX, XXC, AXX, XAX, XXA, UXX, XUX, XXU, or XXX, and wherein each of Y and X are an unnatural nucleotide comprising an unnatural nucleobase selected from

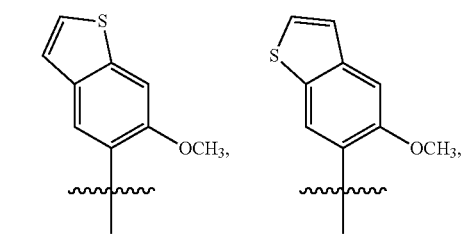

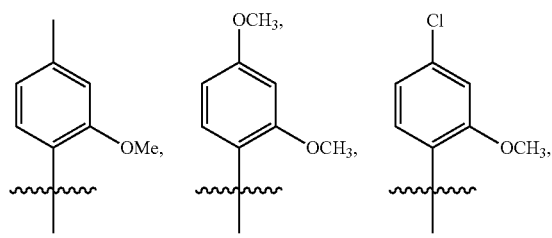

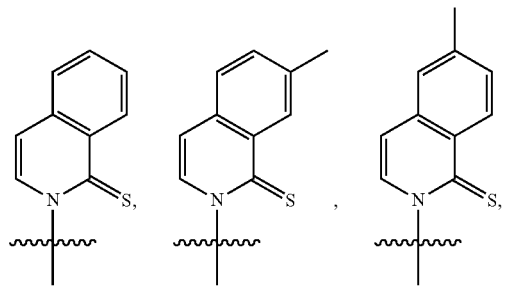

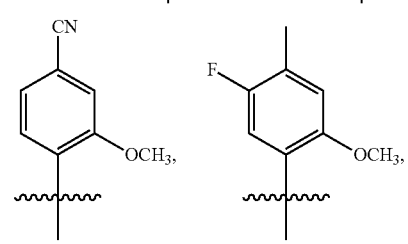

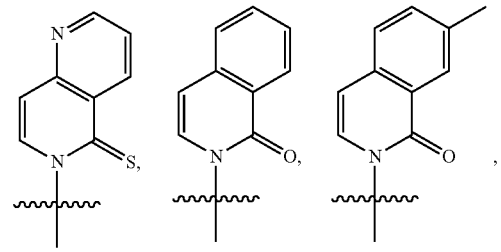

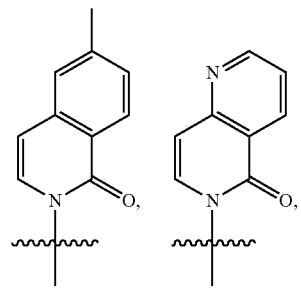

-continued

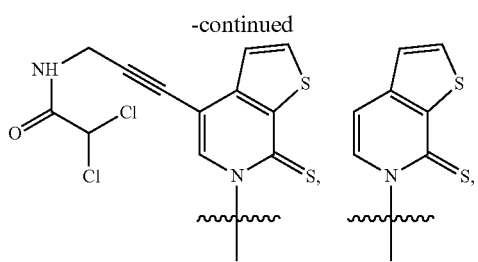

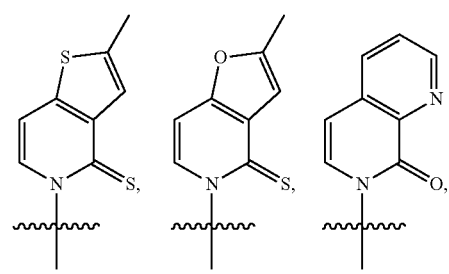

and wherein the anticodon of the tRNA pairs with the codon of the mRNA.

2. The cell of claim 1, wherein the cell further comprises an oligonucleotide encoding the tRNA.

3. The cell of claim 1, wherein the cell further comprises an oligonucleotide encoding the aminoacyl tRNA synthetase.

4. The cell of claim 1, wherein the cell further comprises an oligonucleotide encoding the mRNA.

5. The cell of claim 1, wherein the cell further comprises an oligonucleotide that encodes the tRNA and the mRNA.

6. The cell of claim 1, wherein the cell further comprises an oligonucleotide that encodes the tRNA, the mRNA, and the aminoacyl tRNA synthetase.

7. The cell of claim 1, wherein the unnatural nucleobase in the anticodon is

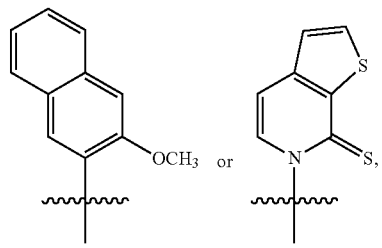 [SMILES: *c1cc2ccccc2cc1OC ; *n1ccc2ccsc2c1=S]

and the unnatural nucleobase in the codon is

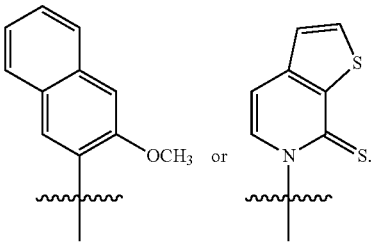 [SMILES: *c1cc2ccccc2cc1OC ; *n1ccc2ccsc2c1=S]

8. The cell of claim 7, wherein the unnatural nucleobase in the codon is

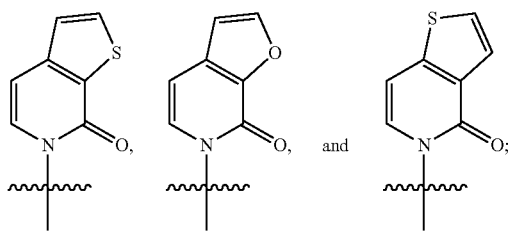

and the unnatural nucleobase in the anticodon is

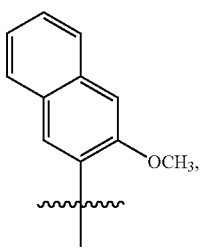 [SMILES: *c1cc2ccccc2cc1OC]

9. The cell of claim 1, wherein the anticodon comprises the sequence GYT or GYC, wherein Y comprises the unnatural nucleobase.

10. The cell of claim 9, wherein the unnatural nucleobase of Y is

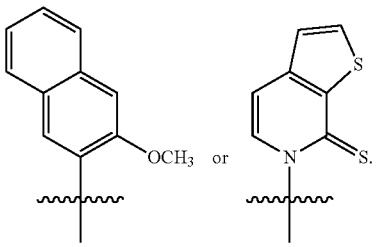 [SMILES: *c1cc2ccccc2cc1OC ; *n1ccc2ccsc2c1=S]

11. The cell of claim 10, wherein the unnatural nucleobase of Y is

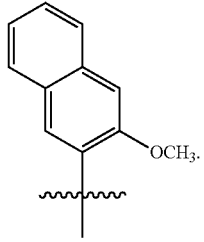 [SMILES: *c1cc2ccccc2cc1OC]

12. The cell of claim 10, wherein the unnatural nucleobase of Y is

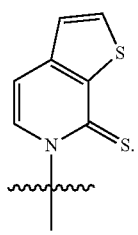 [SMILES: *n1ccc2ccsc2c1=S]

13. The cell of claim 1, wherein the codon comprises the sequence AXC or GXC, wherein X comprises the unnatural nucleobase.

14. The cell of claim 13, wherein the codon comprises the sequence AXC.

15. The cell of claim 14, wherein the unnatural nucleobase of X is

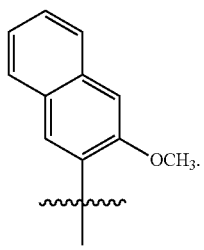 [SMILES: *c1cc2ccccc2cc1OC]

16. The cell of claim 14, wherein the unnatural nucleobase of X is

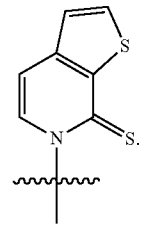

17. The cell of claim 13, wherein the codon comprises the sequence GXC.

18. The cell of claim 17, wherein the unnatural nucleobase of X is

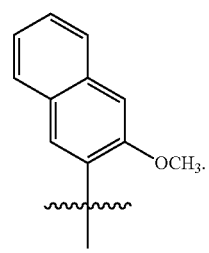 [SMILES: *c1cc2ccccc2cc1OC]

19. The cell of claim 17, wherein the unnatural nucleobase of X is

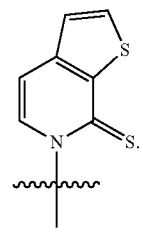

20. The cell of claim 1, wherein the aminoacyl tRNA synthetase is from *Methanosarcina barkeri*.

21. The cell of claim 1, wherein the aminoacyl tRNA synthetase is from *Methanococcus jannaschii*.

22. The cell of claim 1, wherein the aminoacyl tRNA synthetase is a pyrrolysyl tRNA synthetase.

23. The cell of claim 1, wherein the aminoacyl tRNA synthetase is a tyrosyl tRNA synthetase.

24. The cell of claim 1, wherein the cell is a microorganism or bacterium.

25. The cell of claim 1, wherein the cell is an *E. coli* cell.

* * * * *